(12) United States Patent
Shoshtaev

(10) Patent No.: US 11,076,888 B2
(45) Date of Patent: Aug. 3, 2021

(54) SPINAL STABILIZATION SYSTEM INCLUDING BOTTOM LOADING WIDE ANGULATION POLYAXIAL ROD ANCHOR ASSEMBLIES

(71) Applicant: Anza Innovations Inc., Del Mar, CA (US)

(72) Inventor: Eugene Shoshtaev, Del Mar, CA (US)

(73) Assignee: Anza Innovations, Inc., Del Mar, CA (US)

( * ) Notice: Subject to any disclaimer, the term of this patent is extended or adjusted under 35 U.S.C. 154(b) by 0 days.

(21) Appl. No.: 16/049,674

(22) Filed: Jul. 30, 2018

(65) Prior Publication Data

US 2019/0029731 A1    Jan. 31, 2019

Related U.S. Application Data

(60) Provisional application No. 62/538,372, filed on Jul. 28, 2017.

(51) Int. Cl.
*A61B 17/70* (2006.01)
*A61B 17/86* (2006.01)
*A61B 17/68* (2006.01)

(52) U.S. Cl.
CPC ...... *A61B 17/7035* (2013.01); *A61B 17/7034* (2013.01); *A61B 17/7038* (2013.01); *A61B 17/861* (2013.01); *A61B 17/8605* (2013.01); *A61B 2017/681* (2013.01)

(58) Field of Classification Search
CPC .... A61B 17/7032–704; A61B 17/7005; A61B 17/7085; A61B 17/7091; A61B 17/8888; A61B 17/888
See application file for complete search history.

(56) References Cited

U.S. PATENT DOCUMENTS

| | | |
|---|---|---|
| 5,549,608 A | 8/1996 | Errico et al. |
| 8,974,507 B2 | 3/2015 | Eisermann et al. |
| 9,084,634 B1 | 7/2015 | Lab et al. |
| 9,707,014 B1 | 7/2017 | Lab et al. |
| 2005/0187548 A1 | 8/2005 | Butler et al. |
| 2006/0235389 A1 | 10/2006 | Albert et al. |
| 2010/0211114 A1 | 8/2010 | Jackson et al. |
| 2012/0046699 A1* | 2/2012 | Jones ............... A61B 17/7037 606/305 |
| 2012/0089150 A1 | 4/2012 | Smith et al. |
| 2012/0136395 A1* | 5/2012 | Biedermann ...... A61B 17/7037 606/279 |
| 2013/0072991 A1 | 3/2013 | Rathbun et al. |

OTHER PUBLICATIONS

International Application No. PCT/US2018044448 International Search Report and Written Opinion dated Oct. 30, 2018.

* cited by examiner

*Primary Examiner* — Nicholas J Plionis
(74) *Attorney, Agent, or Firm* — Jay B. Bell

(57) ABSTRACT

The disclosure provides a spinal implant having spinal anchors comprising a bone anchor and a receiver configured to securely and polyaxially receive the bone anchor. Further, provided herein are methods for using the spinal implant.

32 Claims, 44 Drawing Sheets

SPINAL STABILIZATION SYSTEM INCLUDING BOTTOM LOADING WIDE ANGULATION POLYAXIAL ROD ANCHOR ASSEMBLIES

CROSS-REFERENCE

This application claims the benefit of U.S. Provisional Application No. 62/538,372, filed Jul. 28, 2017, which application is incorporated herein by reference.

BACKGROUND OF THE INVENTION

Spinal deformities, injuries, and diseases involving the spine have been treated surgically using anchor assembly spinal implants comprising a plurality of anchors assemblies and a rod, whereby the substantially rigid rod connects the anchor assemblies to form a structure that supports, realigns, and/or repositions certain vertebrae for the purpose of stabilizing, immobilizing, and/or adjusting spinal alignment.

SUMMARY OF THE INVENTION

Provided herein is a polyaxial spinal anchor assembly comprising a bone anchor and a receiver. The bone anchor has a first end comprising a head, a second end, a longitudinal axis from the first end to the second end, and a neck between the first end and the second end. An outer surface of the head comprises a drive feature and at least one head recess. At least a portion of the second end comprises a bone engagement. The receiver has first receiver end, a second receiver end, and a receiver axis from the first receiver end to the second receiver end. The first receiver ends comprises a socket cavity comprising a socket aperture configured to releasably receive the head, and a socket cavity slot extending from the socket cavity and configured to receive the neck. The socket aperture and the socket cavity slot are configured to releasably engage with the bone anchor upon rotation of the bone anchor with respect to the socket cavity, translation of the bone anchor with respect to the socket cavity, or both.

In some embodiments, the head recess comprises a channel. In some embodiments, the channel is generally perpendicular to the longitudinal axis. In some embodiments, the assembly further comprises a rod. In some embodiments, the receiver further comprises a rod slot configured to accept the rod. In some embodiments, the rod slot is generally perpendicular to the receiver axis. In some embodiments, the receiver further comprises a compression element between the first receiver end and the second receiver end. In some embodiments, the compression element is configured to transfer a force between the rod and the head. In some embodiments, the assembly further comprises a set screw. In some embodiments, the receiver further comprises a threaded bore configured to threadably receive the set screw. In some embodiments, the threaded bore is generally parallel to the receiver axis. In some embodiments, the socket cavity releasably constrains the head to rotate about the longitudinal axis, a rotational axis perpendicular to the longitudinal axis, or both. In some embodiments, wherein the socket cavity releasably constrains the head to rotate 360 degrees about the longitudinal axis. In some embodiments, wherein the socket cavity releasably constrains the head to rotate within a range of about 5 degrees to about 90 degrees from the rotational axis.

Also provided herein is a method of engaging a screw with a receiver. A polyaxial anchor assembly is provided. The polyaxial anchor assembly comprises a bone anchor and a receiver. The bone anchor has: a first end comprising a head, wherein an outer surface of the head comprises at least one head recess; a second end, wherein at least a portion of the second end comprises a bone engagement; and a neck between the first end and the second end. The receiver has: a first receiver end comprising a socket cavity comprising a socket aperture configured to releasably receive the head, and a socket cavity slot extending from the socket cavity and configured to receive the neck; a second receiver end. The receiver is advanced toward the screw. The head is inserted into the socket cavity. The head is releasably engaged with the socket cavity by rotating the bone anchor with respect to the socket cavity, translating the bone anchor with respect to the socket cavity, or both.

In some embodiments, rotating the bone anchor with respect to the socket cavity comprises rotating the bone anchor with respect to the socket cavity in a first rotational direction, and rotating the bone anchor with respect to the socket cavity in a second rotational direction different than the first rotational direction. In some embodiments, translating the bone anchor with respect to the socket cavity comprises translating the bone anchor with respect to the socket cavity in a first translational direction, and translating the bone anchor with respect to the socket cavity in a second translational direction different than the first translational direction. In some embodiments, translating the bone anchor with respect to the socket cavity comprises translating the bone anchor with respect to the socket cavity in a first translational direction, and translating the bone anchor with respect to the socket cavity in a second translational direction different than the first translational direction. In some embodiments, the method further comprises inserting the neck into the socket cavity. In some embodiments, the method further comprises employing a driver feature surface of the head to attach the bone anchor to a target work surface. In some embodiments, the method further comprises providing a rod and inserting the rod into a rod slot within the receiver. In some embodiments, the method further comprises providing a set screw and inserting the set screw over the rod and into a threaded bore within the receiver. In some embodiments, the method further comprises tightening the set screw within the threaded bore to compress a compression element between the rod and the head.

Another aspect provided herein is a polyaxial spinal anchor assembly comprising: a bone anchor having: a head comprising a first keyed contour in at least one plane; and a neck extending from the head having a diameter less than a diameter of the head; and a receiver having: a base having an outer surface and an inner surface defining a volume for configured to receive and articulate the head; a first opening having a second keyed contour configured to engage and disengage with the head of the bone anchor; and a second opening extending from the first opening and the volume, wherein the second opening is generally perpendicular to the first opening and configured to engage and disengage with the neck of the bone anchor, and wherein the second opening permits insertion of the head into the volume upon translation, rotation, or both of the first keyed contour with respect to the second keyed contour.

In some embodiments, the assembly further comprises a rod. In some embodiments, the receiver further comprises a rod slot configured to accept the rod. In some embodiments, the receiver further comprises a compression element between the first receiver end and the second receiver end. In some embodiments, the compression element is configured to transfer a force between the rod and the head. In some embodiments, the assembly further comprises a set screw. In some embodiments, the receiver further comprises a threaded bore configured to threadably receive the set screw.

Another aspect provided herein is a spinal stabilization system comprising: a stabilizer comprising a rod, and at least one bone anchor assembly comprising a fixator comprising a screw having a threaded shaft joined by a neck to a head with a rounded contour, which cooperates with a rod receiver. In some embodiments, the rod receiver includes an inner surface defining a recess for receiving the screw head, the contour of the head may be a complementary shape such that the receiver is able to articulate about the head in a cone of articulation defined about an axis of the recess. In some embodiments, the recess includes a first opening and a second opening. In some embodiments, the first opening is sized and shaped to permit the neck to extend from the fixator head to articulate there-within and exit the recess through the first opening. The first opening may comprise a circular portion of a slightly larger diameter than that of the screw head. In some embodiments, the second opening has a central axis extending through the receiver at an angle with respect to the first opening (i.e. a "terminal opening"), wherein the angle is 90°±20° or "transverse"

In some embodiments, the screw angulates with respect to the first opening to define a bottom-loading profile permitting insertion of the neck and head into a second opening (i.e. an "entry opening") and the first opening of the receiver respectively at a first angular orientation (i.e. the "entry position") with respect to the profile and further where the relationship between the neck, head and first and second recesses are such that the receiver is subsequently rotated about the head and neck to engage the head and neck in a position (i.e. the "operable position") from which the fixator cannot be removed from the receiver through the second opening. In some embodiments, the screw can also be top loaded into the receiver through the receiver central bore; this method would typically be used at factory assembly and would be followed by inserting the compression member into the receiver to capture the screw.

Another aspect provided herein is a bone screw comprising: a head with a contour for engagement with a receiver; and at least one keyed surface on the contour of the head such that the head can be inserted through an opening (or openings) of the receiver and can be subsequently moved into a position relative to the receiver (or alternatively the receiver can be moved about the fixator head) whereby a screw can be captured in a volume of the receiver spaced below a rod channel in the receiver which is constrained by a member that partially closes or occludes the otherwise circular opening.

Provided herein, in some embodiments, is a bone anchor for engagement with a bone stabilization rod includes: a fixator, such as a screw, hook, or nail or other means to hold an implant relative to a bone, which is integral to or assembled during use with a rod receiver. In some embodiments, the rod receiver has a base having an outer surface including a surface, which opposes a bone in use, and an inner surface defining a contoured volume. In some embodiments, the contoured volume is at least some portion of a sphere and receives a rounded head of the bone fixator. In some embodiments, the rounded contour of the head, also preferably at least some portion of a sphere is of a substantially complementary size and shape to the contoured volume such that the receiver may articulate about the head or alternatively the head may articulate in this recess or contoured volume in the rod receiver. In some embodiments, this contoured volume has a terminal (relative to the depth of the receiver) opening through which the bone fixator shaft passes in an operable position, i.e., for attachment to the bone in use. In some embodiments, the terminal opening is generally circular and slightly larger in diameter than the circumference of the head of the bone fixator. In some embodiments, one portion of the terminal opening is occluded by keyed area which is for example, a shoulder or flange member extends across a portion of the circular opening so as to restrain the rounded fixator head in the contoured volume when the head is oriented in an operable orientation, e.g., when the fixator shaft extends through the terminal opening. In some embodiments, this interference constrains the fixator within the volume of the receiver but allows the rotation that gives rise to polyaxial fixation.

In some embodiments, the keyed contour of the terminal opening allows the complementary keyed contour of the screw head to pass into the internal volume of the receiver when the keyed portion of the head is aligned with the keyed contour of the terminal opening. In some embodiments, the terminal opening has a circular portion mating with the "uninterrupted or un-keyed" portions of the spherical head, and a keyed portion mating with the keyed portion of the head. In some embodiments, at a complementary mating orientation of the head contour relative to the terminal opening contour, the projection of the screw head keyed geometry is aligned with the mating geometry of the terminal opening of receiver to allow for assembly, while the keyed geometry also provides for interference with the circular cross-section of the head when the "uninterrupted or un-keyed" portion of the head encounters the keyed portion of the terminal opening both when the screw head is inside (assembled) or outside (un-assembled) of the internal volume of the receiver. In some embodiments, in addition to the assembly and retention functionality, the keyed contour of the terminal opening results in only a relatively small section (or a circular sector) of the terminal opening interfering with the spherical diameter of the screw (percent head coverage) thereby retaining it in the receiver. In some embodiments, this low percent head coverage results in the ability to achieve relatively high angulation of the screw relative to the receiver central axis without increasing risk of disassembly. In some embodiments, the circular sector responsible for interference between the screw head diameter and the receiver (as observed on a view along the central axis of the receiver) is defined as a central angle of the sector occupied by the keyed portion of the terminal opening and expressed as a percentage of 360 degrees. This percentage may be referred to as percent head coverage (i.e. if the keyed portion occupies exactly a half of the opening, then the central angle is 180 degrees and % coverage is 50%). In some embodiments, the percent head coverage is less than about 50%, and less than about 45%, less than about 40%, less than about 30%, less than about 20% or smaller. %). In some embodiments, the percent head coverage is from about 10 to about 50%. In some embodiments, the percent head coverage is from about 20 to about 40%

In some embodiments, the terminal opening in the receiver is joined with at least one entry opening in the base, which is operable to permit a neck extending from the head to be received in the opening at an entry position in which the head is located within the contoured volume at an entry orientation and the neck extends through the entry opening. In some embodiments, in this position, the center of the spherical portion of screw head is substantially concentric with the center of the spherical portion of the receiver contoured volume allowing the screw to be pivoted from the entry position to an operable position in the contoured recess.

In some embodiments, the keyed portion of the terminal opening may also include a concavity or recess that accommodates the neck of the screw that joins the screw head to the threaded shaft. In some embodiments, the keyed portion extends across from 25% to 50% of the circumference of the terminal opening (as defined by an angle from the center of a cross-section of the screw head at the diameter and extending to the edges of the keyed portion adjacent the screw head, but preferably from about 30% to about 40% of the circumference +/−about 10% and preferably about 5%). In some embodiments, in the operable position, an interference relationship is provided between the keyed portion of the terminal opening and the exterior spherical surface of the screw head, which interference is at least about 10% of the circumference of the screw head, and more preferably at least about 20%, and most preferably from about 25 to about 50% total percent head coverage must be subject to the interference In some embodiments, the keyed portion of the head is a planar area that is external to a central drive feature in the top portion of the head, and in another embodiment, the fixator head has a first area that is planar opposing a second planar surface that define a single plane, preferably, orthogonal to the long axis of the screw shaft and transverse to that, the top portion of the fixator head includes a rounded portion where the head continues to extend upwards in the rounded (or preferably spherical configuration) and opposing portions of the head terminate in arched configurations. In some embodiments, radially internal to the flats and to the rounded arches, the head includes a drive feature, which is a hexagonal recess (or other appropriate shape, such as a hexalobe). Alternatively, the head may include another keyway, such as a pair of flats that are parallel and located equidistant on either side of the equator of the rounded head in planes transverse to the long axis of the fixator.

Another aspect provided herein is a method of forming a stabilization system. A fixator and preferably a bone screw are provided. The fixator and bone screw are joined by a neck to a contoured head, which preferably forms a portion of a sphere, and includes at its top portion, a keyed surface which is an edge or flat transverse to the screw long axis. A receiver is provided. The receiver has a base with an inner surface defining a contoured volume for receiving the head of the bone screw, and an entry opening extending through the base into the contoured volume and defining a profile that permits insertion of the head into the contoured volume of the base at an entry position of the screw relative to the receiver. The head includes a key and the contoured volume including a keyway where the head can be moved into a second position where the head is captured in the contoured volume by the keyway that defines a portion of the opening and which extends less than about 50% circumferentially (i.e., occupies a circular sector with a central angle of less than about 180 degrees) of the opening.

In some embodiments, the polyaxial fixator assembly is supplied as factory assembled including receiver, compression member, and fixator (screw), or may be supplied to be assembled intraoperatively, in which case the receiver and the compression member come factory assembled, and the fixator screw is supplied separately for intraoperative assembly. In some embodiments, during assembly, a compression insert is loaded into the receiver, for example, by sliding, forcing, ratcheting, or threading the compression insert into the central bore of the receiver and securing in a recess in the receiver in a position in which the screw head is held in position whereby the screw head may enter the receiver contoured volume. In some embodiments, when the screw fixator is in the operable second position, the compression member makes light contact with the spherical surfaces of the screw head, preferably generating light friction allowing the screw to be angulated inside the receiver but keeping its set angle when not moved around. In some embodiments, the rod is then urged into position in a cradle formed on the compression insert and further is held on the compression insert and in a rod slot formed between two opposing arms of the rod receiver. In some embodiments, a top loading closure structure (fastener) is threaded down on the receiver, either externally or internally, which forces the rod against the compression member, which in turn forces the spherical screw head against the lower surfaces of the receiver contoured volume, thereby locking the assembly into fixed frictional contact where all of the above components are rigidly locked with respect to each other.

As such the aspects herein provide an anchor assembly for supporting and installing bone attachment structures which may provide a bottom loading feature in which a fixator is loaded in one position into a receiver and moved or pivoted to a second position where it is held for use. In the second position, the fixator may be moved through a wide range of angulation in a terminal opening and cannot be removed from the receiver as a result of a limited but sufficient interference between the fixator head and an occluded portion of the terminal opening. The screw may angulate substantially equally in every direction around the central axis of the receiver except in the direction of the occluded portion of the opening, where the angulation of the screw is more limited.

Another aspect provided herein is a polyaxial spinal anchor comprising a receiver having a pair of opposed arms defining an open channel sized and shaped to receive a longitudinal connecting member. In some embodiments, the receiver further has a central bore and a lower opening, the bore communicating with both the U-shaped channel and the lower opening.

Another aspect provided herein is a dynamic vertebral support connecting member implantation kit adapted for use with a plurality of vertebrae and comprising a plurality of bone anchors as described and a stabilizer being adapted for implantation in or on a vertebra or vertebrae (including, a cervical vertebra, a thoracic vertebra, or a lumber vertebra or the sacrum), each of the implants having structure for attachment to an insertion tool. In some embodiments, the kit also includes a plurality of insertion tools, at least one driver, at least one anchor-holding tool and at least one reduction instrument configured for urging the rod into the receiver U-shaped channel. Other tools may be included in the kit.

Another aspect provided herein is a method comprising the steps of: providing a fixator, affixing it to a vertebrae, then attaching a receiver subassembly (receiver with a compression member detained inside) by feeding it onto the head of the fixator in a first position, moving the receiver into a second position, then feeding a stabilizer into the receiver, and locking the construct into a desired position by threading a fastener (closure structure) onto or into the receiver on top of the stabilizer.

Another aspect provided herein is a spinal anchor assembly comprising a receiver defining a rod axis and a bone screw having a threaded portion defining a screw long axis, which is joined by a neck to a head member, which forms a portion of a sphere having a diameter, and the head member including a keyed surface which has an aspect transverse to the screw long axis. The receiver has a base defining an inner surface defining a volume for receiving the head member, and a first opening extending through the base into the volume. The first opening defines a contour that permits insertion of the head into the volume of the base at a first position of the screw relative to the receiver. The volume includes a keyway having an interference with a portion of the first opening and which cooperates with the keyed surface of the head such that the head can be moved into a second position whereby the head is retained in the volume due to the interference with the portion of the first opening.

In some embodiments, the sector is a circular sector responsible for interference between the screw head diameter and the receiver includes a central axis of the receiver and the circular sector is defined relative to a central angle of the sector occupied by the keyway at the first opening and expressed as a percentage of 360 degrees. In some embodiments, the central angle is 180 degrees and % head coverage is 50% or less. In some embodiments, the percent head coverage is less than 45%. In some embodiments, the percent head coverage is less than 40%. In some embodiments, the percent head coverage 10-50%. In some embodiments, wherein the percent head coverage 20-40%. In some embodiments, the keyed surface is a flat that extends across the head of the screw. In some embodiments, the spinal anchor assembly further comprises a rod and the receiver further has a channel that defines the rod axis. In some embodiments, the keyed surface is a flat that extends at 90°+/−5° to the screw long axis. In some embodiments, the keyed surface includes a segment cut from a top portion of the screw head member on a first side of the long screw axis that includes a flat at 90°+/−5° to the screw long axis. In some embodiments, the keyed surface includes radially symmetric opposed keyed surfaces which are two segments removed from the screw head member. In some embodiments, the screw head member is captured in the receiver volume by a shoulder that defines a portion of the opening from the base into the volume and which extends less than 50% circumferentially of the opening. In some embodiments, the rod receiver volume has an axis transverse to the rod axis and the screw long axis is capable of at least 120° of conical rotation with respect to the rod receiver volume axis. In some embodiments, the first opening extends across the base of the rod receiver to open from a first position and from a position radially at 180°+/−15° from the first position.

Another aspect provided herein is a spinal anchor assembly comprising a spinal anchor including a rod receiver and a bone screw defining a screw long axis, which is joined by a neck to a contoured head, which forms a portion of a sphere. The rod receiver has a channel that defines a rod axis and a base with an inner surface defining a volume for receiving the head of the bone screw, and a terminal opening extending through the base into the volume. The screw head is captured in the receiver volume by a flange that defines a portion of the opening into the volume and which extends less than 50% circumferentially of the opening.

In some embodiments, wherein the flange extends less than 40% circumferentially of the opening. In some embodiments, the screw neck has a diameter of a size n and the flange has a recess that forms a portion of a circle having a diameter that is from 90-110% of n. In some embodiments, the recess forms from 15-40% of the area of a circle. In some embodiments, from 50-80% of the volume of the head of the screw is within the volume of the rod receiver. In some embodiments, the spinal anchor assembly further comprises a rod and wherein the rod is held in the rod channel by a compression member that threads into or unto the rod receiver. In some embodiments, the receiver volume includes a pair of recesses, the rod is held in the rod channel by a compression member, and the compression member has a pair of wing members that flex into the recesses in the volume to hold the compression member in position in the volume.

Another aspect provided herein is a method of assembly of a spinal implant assembly which includes a rod and at least two spinal anchors each having a bone screw and a rod receiver. The method comprises steps of: attaching a bone screw having a threaded shaft along a screw axis and joined at a neck to a head having at least a portion of a sphere and a keyway transverse to the screw axis by screwing the shaft into a vertebrae, and joining a the bone screw at a first position to a rod receiver which has a base with an inner surface defining a volume for receiving the head of the bone screw, and a first opening extending through the base into the volume and defining a profile that permits insertion of the head into the volume of the base at the first position of the screw relative to the receiver; and moving the head to a second position in the volume.

Another aspect provided herein is a method of treatment of a spine comprising steps of: (i) providing spinal rod and anchor assembly comprising a spinal implant having a rod and at least two spinal anchors, the spinal anchors each including a rod receiver and a bone screw defining a screw long axis, which is joined by a neck to a contoured head, which forms a portion of a sphere, and the head including a crown having a keyed surface which is a flat transverse to the screw long axis; the rod receiver having a channel that defines a rod axis for the rod and a base with an inner surface defining a volume for receiving the head of the bone screw, and a first opening extending through the base into the volume and defining a profile that permits insertion of the head into the volume of the base at a first position of the screw relative to the receiver and the volume including a keyway which cooperates with the keyed surface of the head where the head can be moved into a second position such that the screw long axis is not parallel to the rod axis and a terminal opening extending through the base into the volume and the screw head is captured in the receiver volume by a flange that defines a portion of the opening into the volume and which extends less than 50% circumferentially of the opening; (ii) attaching a bone screw having a threaded shaft along a screw axis and joined at a neck to a head having at least a portion of a sphere and a keyway transverse to the screw axis by screwing the shaft into a vertebrae, joining a the bone screw at a first position to a rod receiver which has a base with an inner surface defining a volume for receiving the head of the bone screw, and a first opening extending through the base into the volume and defining a profile that permits insertion of the head into the volume of the base at the first position of the screw relative to the receiver; and moving the head to a second position in the volume.

Another aspect provided herein is a spinal rod and anchor assembly comprising a spinal implant having a rod and at least two spinal anchors, the spinal anchors each including a rod receiver and a bone screw defining a screw long axis, which is joined by a neck to a contoured head, which forms a portion of a sphere; the rod receiver having a channel that defines a rod axis for the rod and a base with an inner surface defining a volume for receiving the head of the bone screw, and a terminal opening extending through the base into the volume and the screw head is captured in the receiver volume by a flange having an amount of material that retains the screw head in the volume and the amount of material that keeps the screw head inside the volume and preventing it from pulling through the terminal opening is dependent exclusively on a two dimensional characteristic of the percentage coverage.

Another aspect provided herein is a spinal anchor assembly comprising a screw having a head that is at least a portion of a first sphere and a receiver having a volume with a recess that is at least a portion of a second sphere which opens in a screw opening that receives the screw in an operable position and which has a compound outline that forms at least a portion of a circle and an interference portion, and the diameter of the first sphere and the second sphere and the circle being the same and the interference opening of the screw opening forms a interference with the head of the screw in the operable position.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION OF THE INVENTION

Figure 1A:
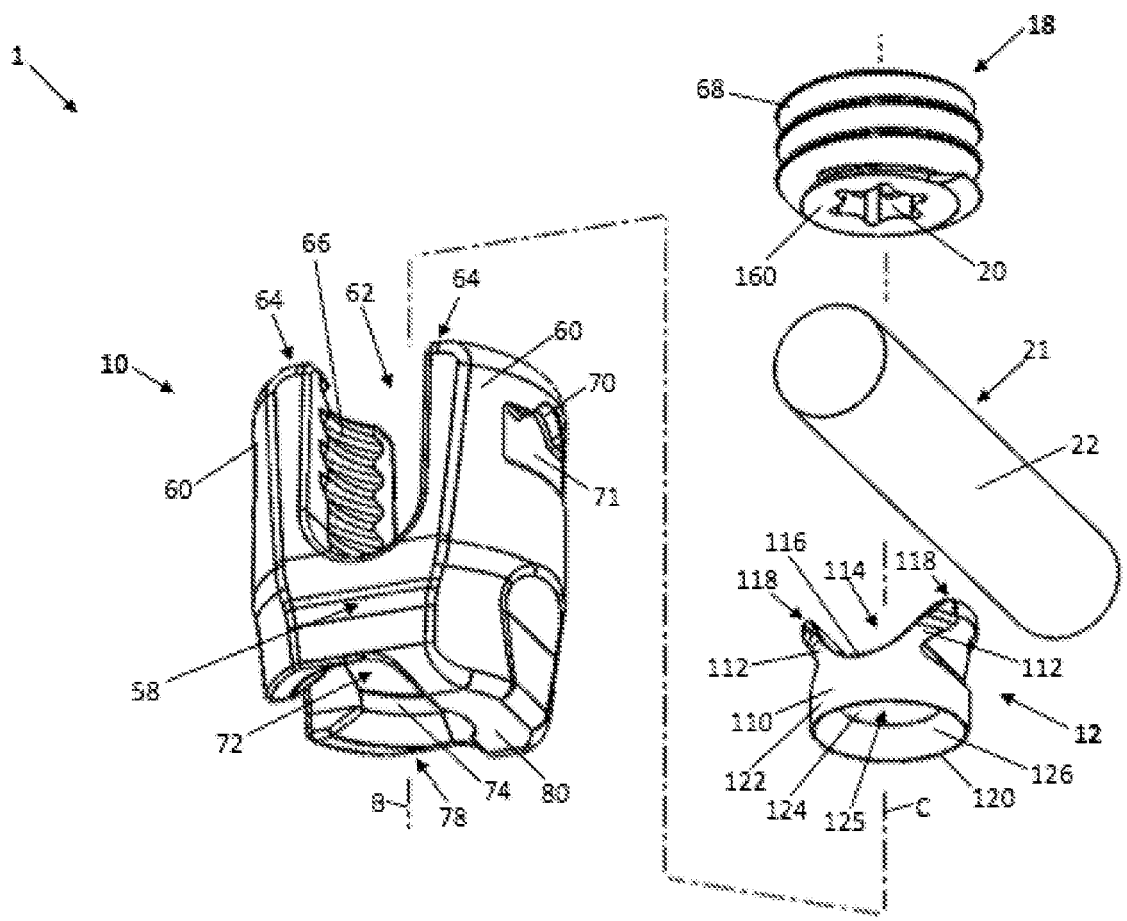
FIG. 1A shows a side exploded view of an exemplary spine stabilizer receiver assembly of the present invention.

While closed-ended and open-ended anchor assemblies are known, open-ended anchor assemblies are particularly advantageous as they hasten surgery by removing the requirement to pass the rod a closed anchor bore. Such open-ended bone anchor assemblies may be laid or urged into an open channel within a receiver or head of such an anchor.

In a fixed bone anchor, the bone anchor may not able to rotate relative to the threaded shaft. As such, the anchor must be positioned precisely to enable rod insertion without bending and additional stress. As such, polyaxial bone screws are commonly preferred.

Open-ended polyaxial anchors allow rotation and often angulation, of the rod receiver about a threaded shaft of a fixator until a desired rotational and angle position of the rod receiver may achieved relative to the fixator shaft. Thereafter, a rod can be inserted into the rod receiver and subsequently the fixator head may locked or fixed in a particular position relative to the shaft. However, in certain instances, a surgeon may desire to set and fix the angular position of the rod receiver relative to the shaft independently of rod insertion or rod locking. Additionally, it may be desirable to reset and fix the angle of orientation of the rod receiver during the surgical procedure.

Open-ended anchor assemblies include a receiver, which has a vertical central bore or recess which includes a lower opening through which the hook portion or screw shaft of the fixator extends along its axis. The receiver bore further communicates at the outer end (relative to the vertebral surface from which it extends) with the U-shaped rod channel. In most cases, the implant includes a fixator comprising a screw that extends along its long axis through the lower opening of the central bore and in instances in which the assembly is polyaxial, the angle of the longitudinal axis relative to a central axis of the lower opening can be chosen from a range of angles which is often conical. This anchor assembly further includes a fixator head or receiver insert, including a top surface sized and shaped for frictional engagement with the longitudinal member. If assembled and not implanted, the screw head may generally form a ball and socket relationship with the receiver when the threaded shaft extends through the central bore, articulating in an angulation cone about the long axis of the central bore. The amount of articulation about that axis may be generally defined by the interference of the screw shaft below the screw head at a screw neck in the opening of the central bore. Because of the possibility of relatively high loads at the screw neck, it generally has to meet certain dimensional specifications in order to avoid shearing of the screw at this location. Thus, the amount of angulation may be constrained in part by this requirement for the screws.

The anchoring of bone screws, hooks, and other types of anchors directly to a vertebra can result in significant forces being placed on the vertebra, and such forces may ultimately result in the over-loading, fracture, or loosening of the bone screw or other anchor from the vertebra. Consequently, the art attempts to achieve, so much as possible, a balanced alignment and loading pattern between the vertebrae in flexion, extension, compression, distraction, side bending, and torsion. The dynamic conditions associated with spinal movement therefore provide a challenge not only for the design of elongate elastic longitudinal connecting members, but also for the design of cooperating bone attachment structure and tooling.

In some cases, it may be desirable to use an anchor that provides a relatively large amount of angulation (i.e., the angle at which the bone screw may be tilted with respect to a longitudinal axis of the anchor housing) over a continuous range of angles around the longitudinal axis of the central bore of the anchor. This larger amount of angulation allows for a wider variety of placement of an anchor screw relative to the vertebrae, which also provides for easier alignment of the rod in each of the anchors.

In addition to the foregoing considerations, anchor assemblies often require the assembly of the anchor during surgery in order to provide for flexibility and decisions made during the surgery. This requires that the assembly of the anchor assembly is easy and swift.

Polyaxial Anchor Assemblies

The present embodiments relate to apparatuses and methods for use in performing spinal surgery and, in particular, to polyaxial bone attachment implants (i.e., anchor assemblies) which capture stabilization members for spinal support and alignment. The embodiments accepts an elongate stabilizer (i.e. a rod) into a stabilizer anchor assembly having a fixator (e.g., a screw, hook, nail, staple, etc.), which forms a multi-axial locked relationship in a stabilizer receiving anchor assembly. The fixator may be advantageously capable of being either top loaded or bottom loaded into the stabilizer receiver of the anchor assembly and the stabilizer receiver may be rotated into a position for holding the stabilizer member with a compression member that captures a spherical-shaped head of the fixator at an angle chosen from a very wide angle of possibility. The anchor includes a keyed relationship to permit the assembly and which, in a different orientation, causes the capture of the fixator. The stabilizer may be loaded into the anchor assembly and unto the compression member and held in that position by a locking member that threads into or onto the stabilizer receiver and secures the construct in the desired position.

Provided herein, per FIGS. 1-6, is a first embodiment of a polyaxial bone screw assembly 1 comprising a fixator, and a bone screw 4 that includes a screw shaft body 6 integral with a screw head member 8, a receiver 10, a compression structure 12, and a fastener 18. The polyaxial bone screw assembly 1 may employ other means of fixation. The receiver 10 and compression structure 12 may be factory assembled and the screw 4 may either be factory assembled or intraoperatively assembled before or after implantation of the screw into bone with the receiver 10.

Figure 1B:
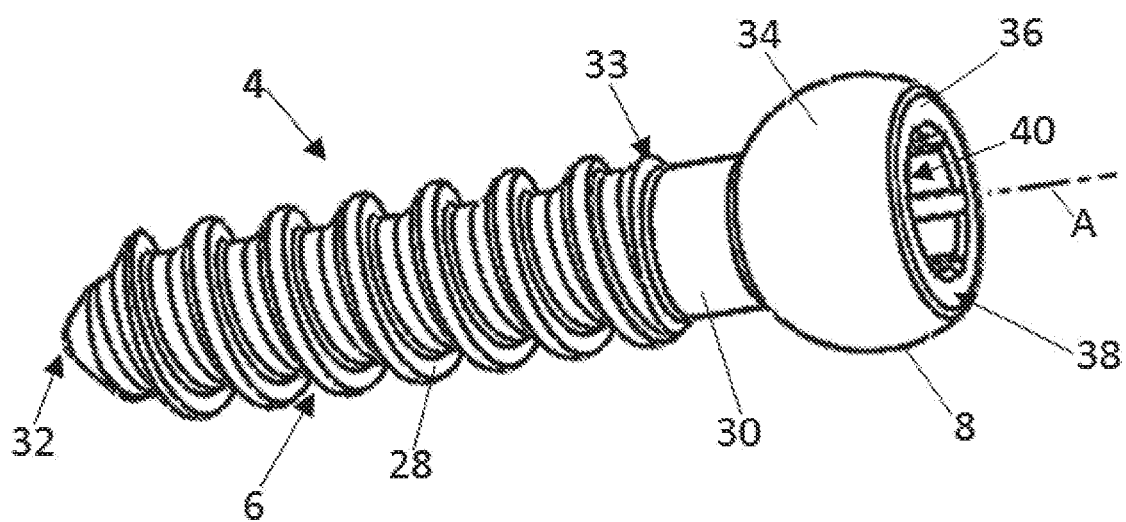
FIG. 1B shows a side exploded view of the exemplary spine stabilizer screw of the present invention.

Per FIGS. 1A and 1B, the screw 4 comprises an elongate bone screw with the screw shaft body 6 having a helically wound bone implantable thread 28 extending from near a neck 30 located adjacent to the head member 8 to an insertion tip 32 of the screw shaft body 6 and extending radially outwardly therefrom. During use, the screw shaft body 6 may utilize a thread 28 for gripping and advancement may be implanted into the vertebra leading with the tip 32 and driven down into the vertebra with an installation or driving tool, so as to be implanted in the vertebra to near the neck 30. The neck 30 may extend axially upwardly and away from the screw shaft body 6. The neck 30 may be of a reduced radius as compared to an adjacent top 33 at the thread run out of the screw shaft body 6 as well as to the major diameter of the thread 28 of the screw shaft body 6. The screw head member 8 may extend axially upwardly and away from the neck 30 to provide a retention and articulation apparatus disposed at a distance from the threaded body top 33, and thus at a distance from the vertebra when the body 6 is implanted in the vertebra. The screw head member 8 may be configured for a pivotable connection between the screw 4 and the receiver 10 prior to fixing of the screw in a desired position with respect to the receiver 10.

Figure 2:
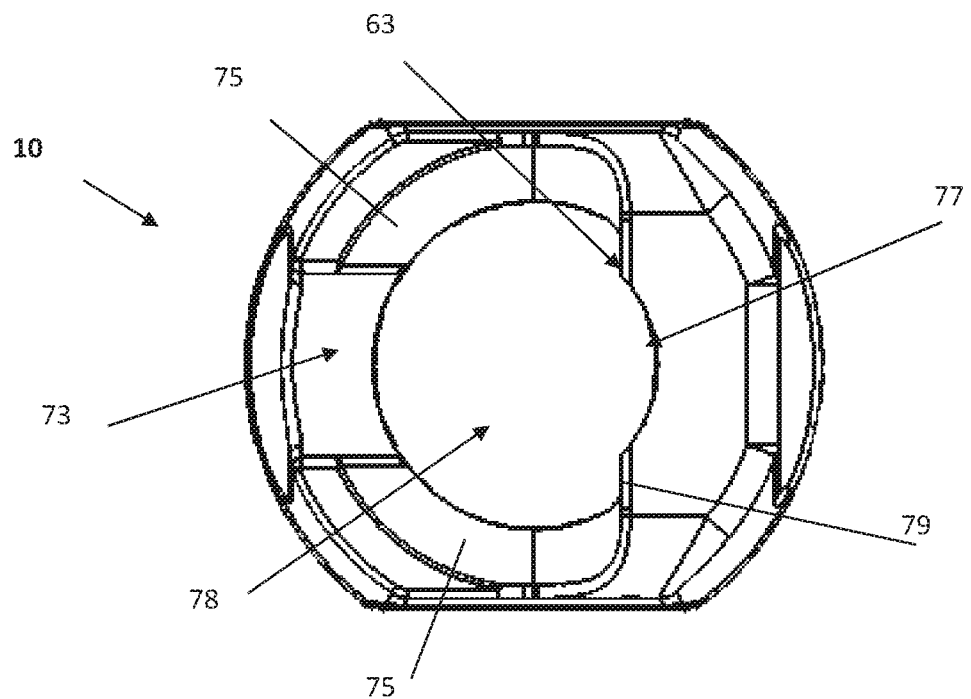
FIG. 2 shows a bottom up view of the exemplary receiver of FIG. 1A.

The head member 8 may comprise at least a portion of a substantially spherical body 34 having a keyed portion 38. In the illustrated embodiment the keyed portion 38 may comprise only a planar upper surface 36, which extends in a plane transverse (i.e., at 90°+/−15°, and preferably at 90°+/−5°) and which truncates a portion of the sphere of spherical body 34. As seen in FIG. 2, the receiver 10 may comprise a terminal opening 78 which in part generally forms a circle that may be sized to be slightly larger than the circumference of the spherical body 34 of the screw head member in FIG. 1B. In some embodiments, a keyed feature 63 may be contiguous to the terminal opening 78 and formed at the lateral edge of a shoulder 79 that partially closes the circular shape of the opening at an angle which may be 90°+/−10° to a bottom surface 80 of the base of the receiver 10, as in FIG. 1A. The shoulder 79 may extend inward toward the center of the circular opening from the projected area to complete the outline of the circle of the opening, and to provide a mating engagement with the keyed portion 38 of the screw head member 8 as the screw 4 is assembled in the receiver 10.

In some embodiments, the relationship between the configuration of the terminal opening allows the head member to be inserted in a first position, and the mating keyed feature 63 in the terminal opening 78 and in the head member 8 of the screw 4 may be a unique in a sufficient way, to allow the screw 4 to be captured within the receiver 10 while permitting a wide angulation in the receiver 10. In some embodiments, the terminal opening 78 extends through the base of the receiver 10 into the volume and the screw head may be captured in the receiver 10 volume by a flange having an amount of material that retains the screw head in the volume and the amount of material that keeps the screw head inside the volume and preventing it from pulling through the terminal opening 78 may be dependent on the amount of interference between the spherical portion of the screw head and the keyed portion 38 of the receiver terminal opening 78 viewed as a projection along the long axis of the receiver, since the material of the keyed portion 38 closes or occludes the terminal opening 78 to the removal of the screw in a operable position that may be different from the entry position of the screw which the keyed relationship permits. In some embodiments, the keyed portion 38 of the head and of the opening 78 could include a surface or surfaces that is/are not flat, but rather perhaps curved, elliptical, or v-shaped and which cooperates together to permit an acceptance of the screw head 8 into the receiver volume 72.

Figure 7:
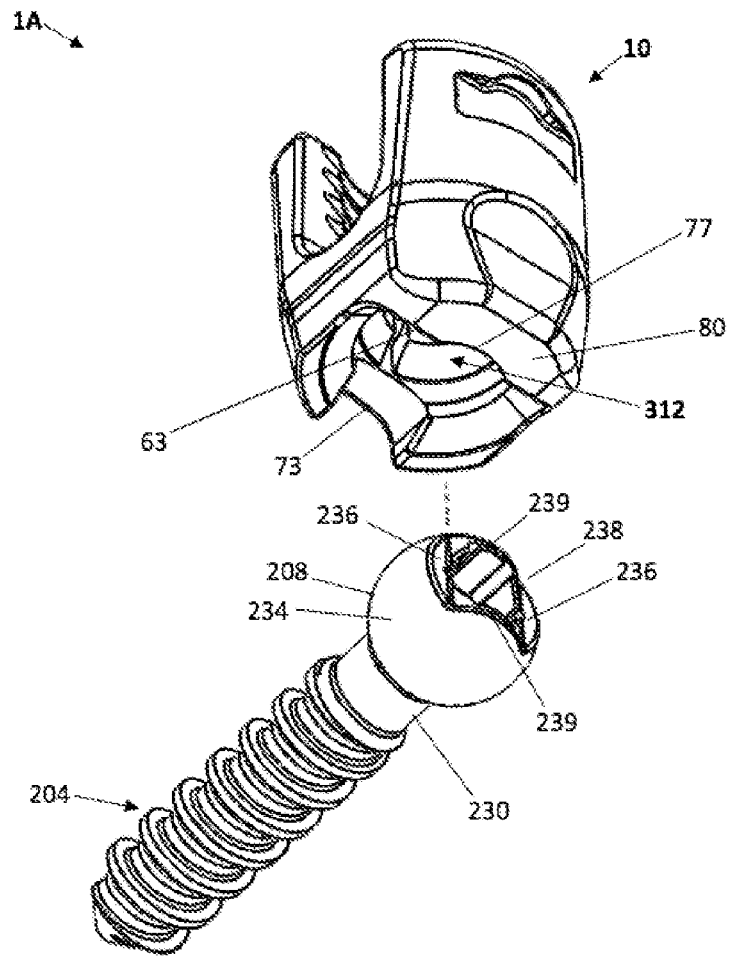
FIG. 7 shows another embodiment of an exemplary spinal insert anchor assembly in with the screw in an entry position for insertion.
Figure 9:
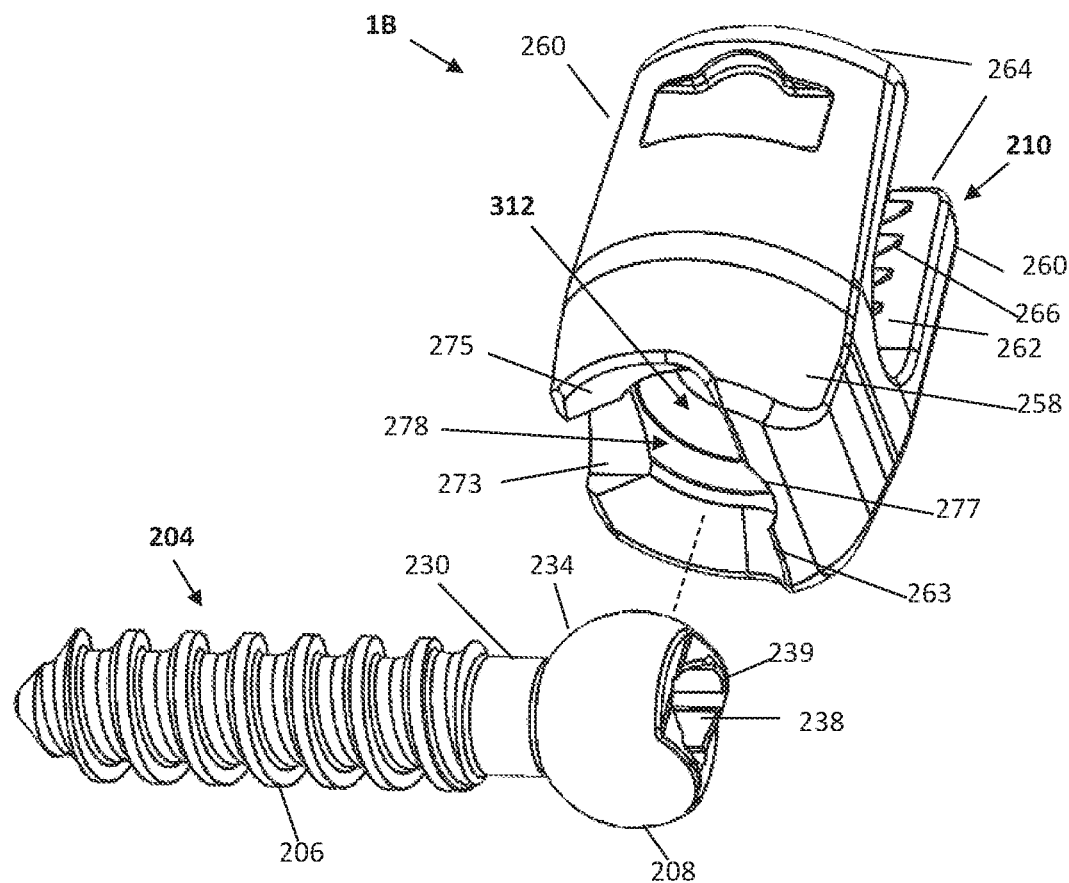
FIG. 9 shows an alternative embodiment of an exemplary spinal anchor assembly of FIG. 7 in which the entry opening is located in the plane defined by the rod receiving channel and 90° to the location in FIG. 7.

In other embodiments, the keyed portion 38 may also include additional surfaces that may further interrupt the spherical surface of the spherical body 34 by removing material from the spherical body 34. In some embodiments, at least some of the additional surfaces are transverse to the long axis of the screw as previously described. Exemplary embodiments of the screw keyed portions are shown in FIGS. 7, 9, 10, and 11, wherein FIGS. 7 and 9 show two different embodiments of the receiver. In some embodiments, the screws include a compound keyed portion 238, which includes opposing co-planar flats 236 cut across the head member 208 of the screw 204. Spaced 90° from the center of the flats 236, the screw head member 208 also include a pair of arched areas 239 which has a profile that corresponds to the relief 77 of the receiver 10. This embodiment may preserve more of the spherical surface of the screw head member which resides in the spherical volume in the receiver.

FIG. 10 and FIGS. 11A-11D illustrate another exemplary screw 404, 504 comprising an alternative keyed feature. In these embodiments, the keyed portion 438, 538 may comprise a pair of flat surfaces 436, 536 which are both perpendicular to the long axis of the screws, 404, 504 but which are parallel and spaced apart rather than being coplanar. In some embodiments, these flat surfaces mate with a keyed feature that may not be radially opposed to but illustrated as 90° radially from the entry opening in the receiver. In some embodiments, the screw head 508 includes a truncated top portion that has a planar aspect surrounding the drive feature 440, 540 of the screws 404, 504. The screw 504 varies from the screw 404 in that may include a thread relief 509 which allows the screw 504 to clear the bottom edge of the terminal opening of the receiver 710 so that the screw can be pivoted from the entry position (transverse with axis of receiver 710) to an operable position. In some embodiments, the process of assembly of the screw 504 with receiver 710 involves aligning the keyed portion 538 of the screw and keyed feature 763 of the receiver in the entry orientation of the screw relative to the receiver (shown in FIG. 11A) and then inserting the screw head into the inner volume of the receiver while the neck of the screw is inserted into the entry opening 773 of receiver (shown in FIG. 11B). In this state, the screw may not be able to pivot down from the entry state into operable state due to interference between the screw thread near neck and the outer lower lip of the receiver adjacent to the entry opening 773 (shown in FIG. 11C). In some embodiments, if the screw is now rotated 90 degrees around its long axis, the reliefs 509 now allow the screw threads to clear the lower lip of the receiver and the screw to be pivoted down into operable position. This two-step assembly process may ensure that accidental disassociation of screw from receiver does not occur since the keyed features of the screw and the receiver are misaligned such that the screw head cannot leave the receiver inner volume when the reliefs 509 are aligned such that the pivoting of the screw from entry position to operable position is permitted.

As shown in FIG. 1B, an internal tool engagement drive feature 40 may extend downwardly and axially into the upper surface 36 of the screw head member 8. The screw head member 8 may comprise hex-shape or hexalobe-shape structure sized and shaped to mate with a driving tool (not shown) having an external drive configured to fit into the tool engagement drive feature 40 for both driving and rotating the screw shaft body 6 into the vertebra.

Figure 13:
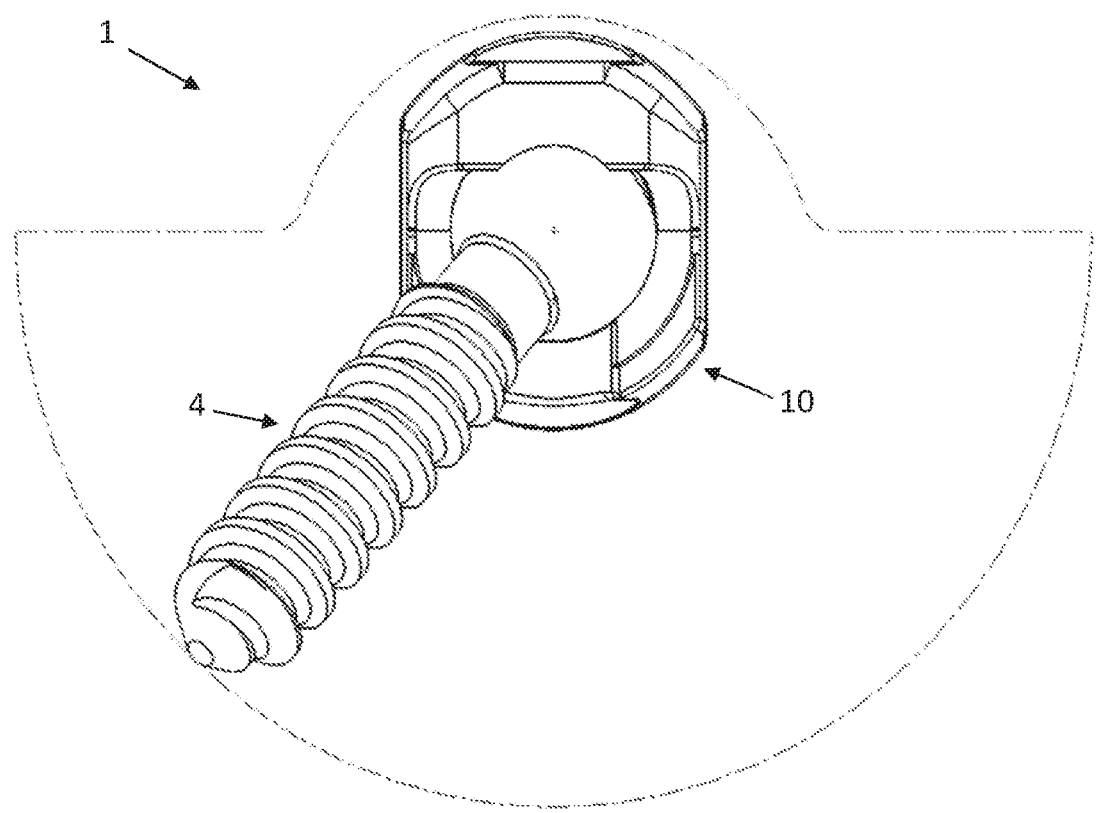
FIG. 13 shows the possible degrees of angulation of the exemplary screw relative to the receiver for the embodiment of FIG. 1.
Figure 14:
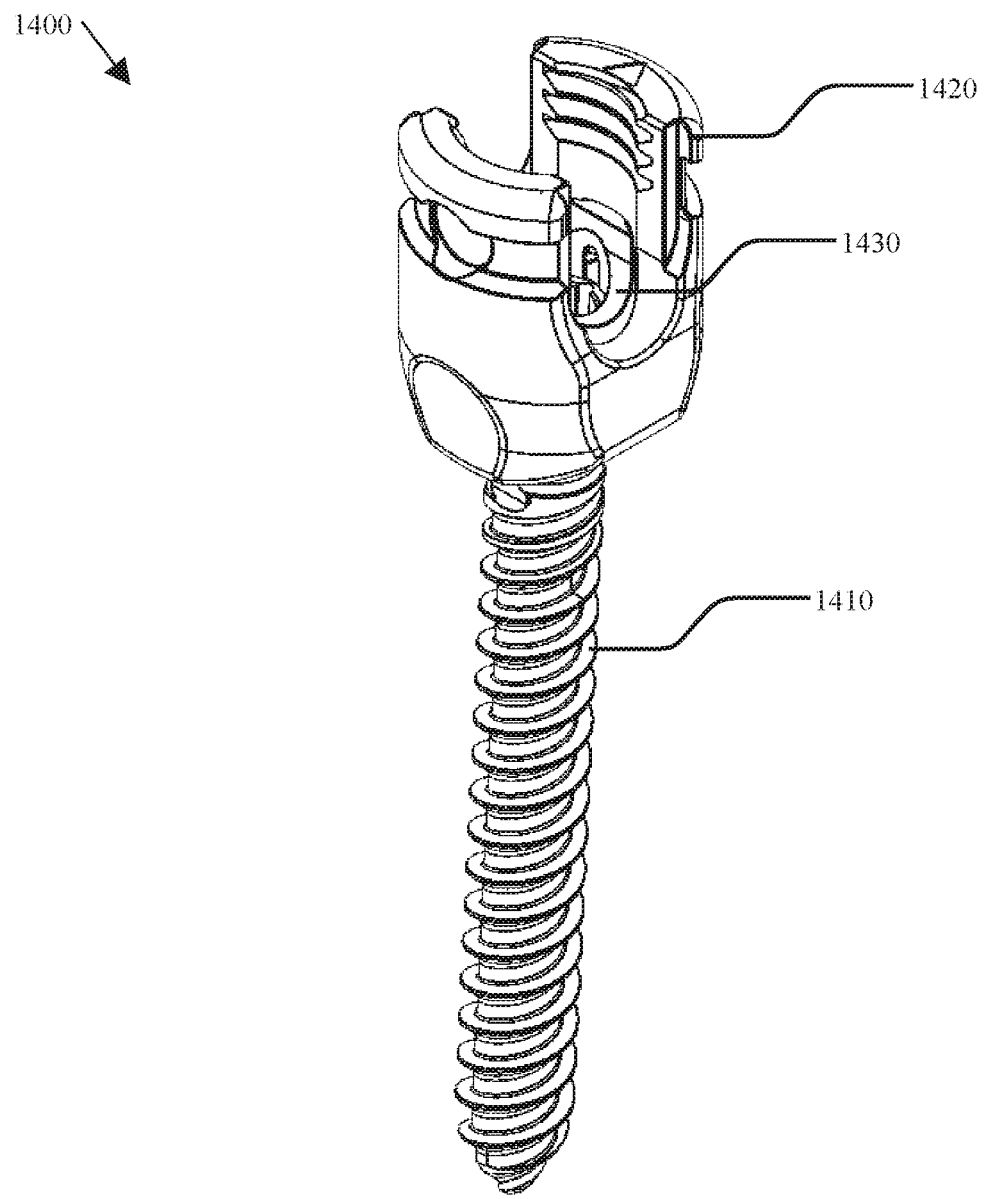
FIG. 14 shows a perspective view of an embodiment of an exemplary spine stabilizer assembly described herein.
Figure 15A:
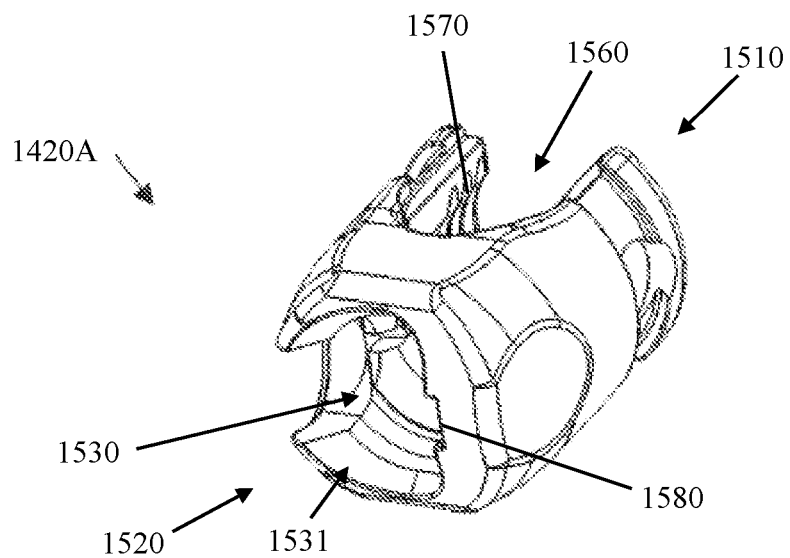
FIG. 15A shows a perspective view of an exemplary first receiver, per embodiments herein.
Figure 15B:
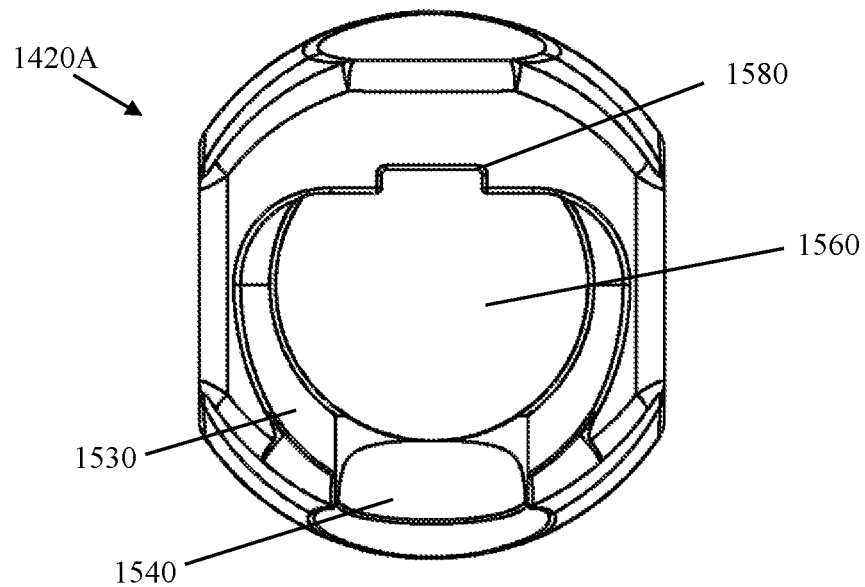
FIG. 15B shows a top view of an exemplary first receiver, per embodiments herein.
Figure 15C:
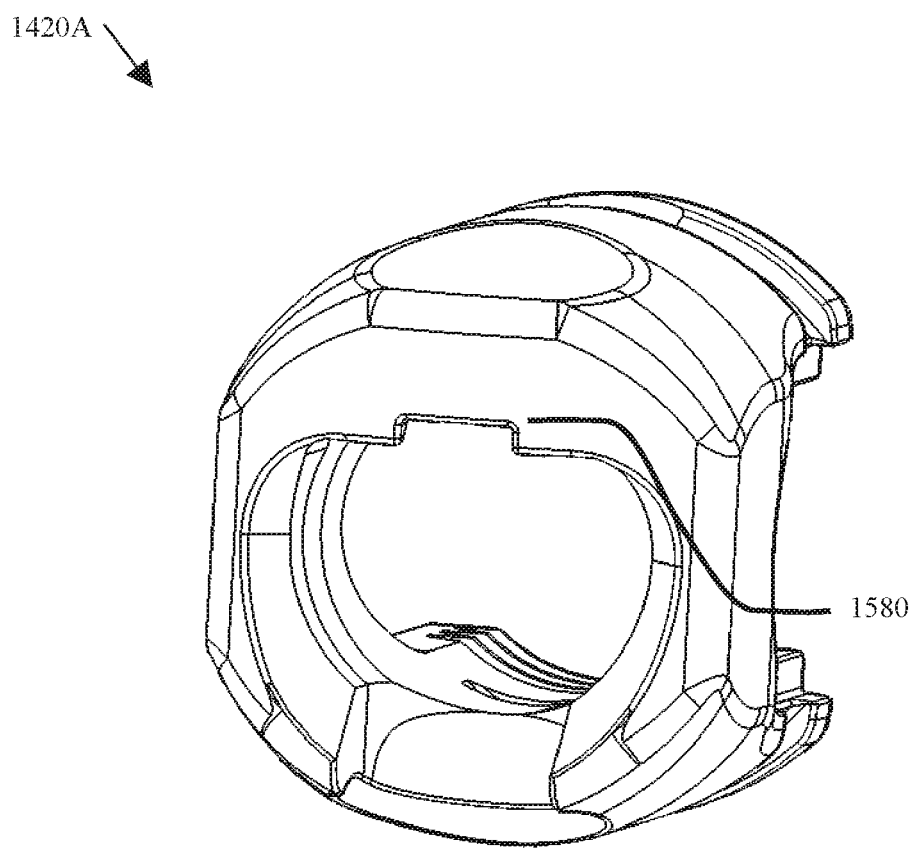
FIG. 15C shows another perspective view of an exemplary first receiver, per embodiments herein.
Figure 15D:
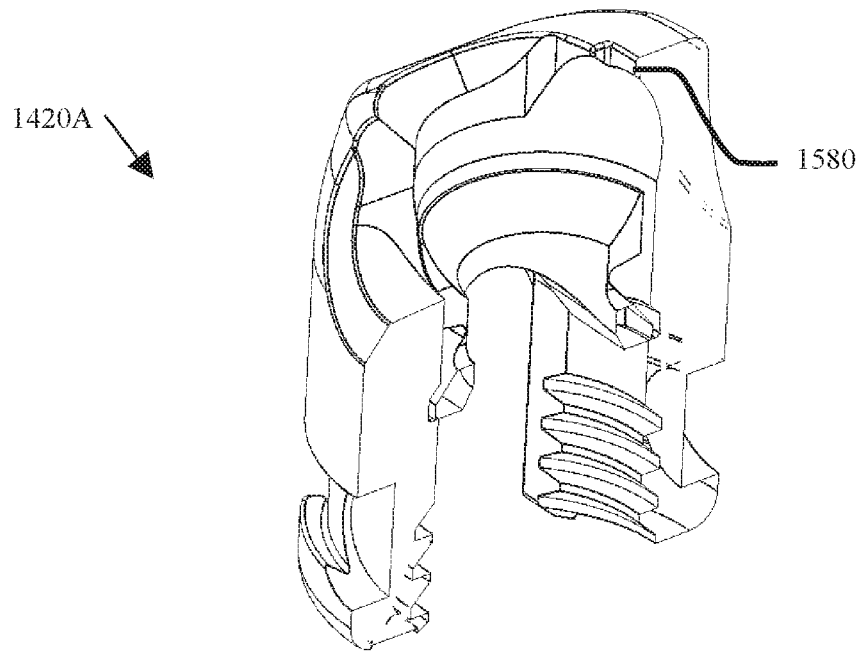
FIG. 15D shows a perspective cross sectioned view of an exemplary first receiver, per embodiments herein.
Figure 15E:
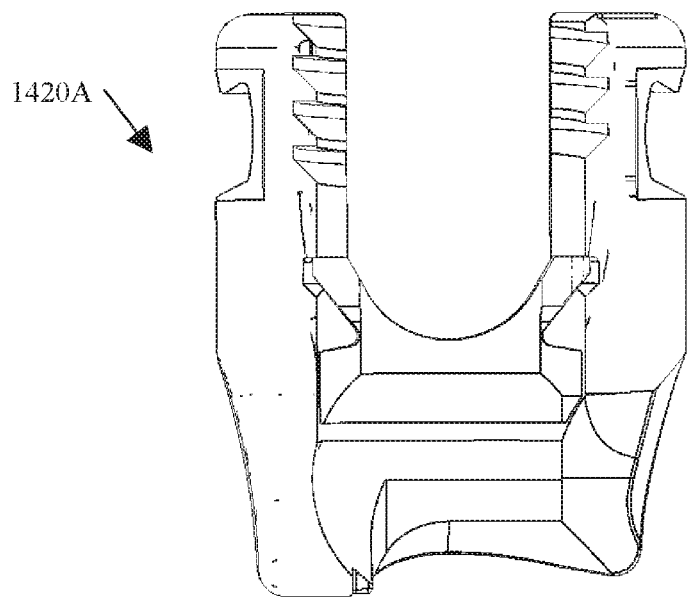
FIG. 15E shows a side cross sectioned view of an exemplary first receiver, per embodiments herein.
Figure 16A:
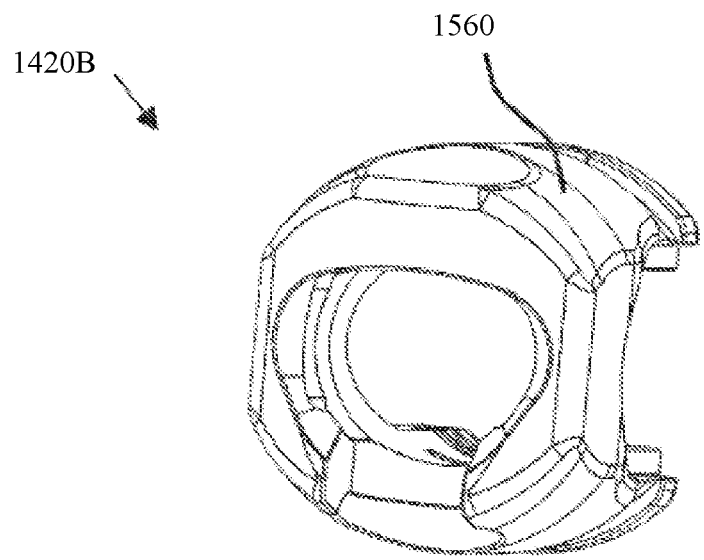
FIG. 16A shows a perspective view of an exemplary second receiver, per embodiments herein.
Figure 16B:
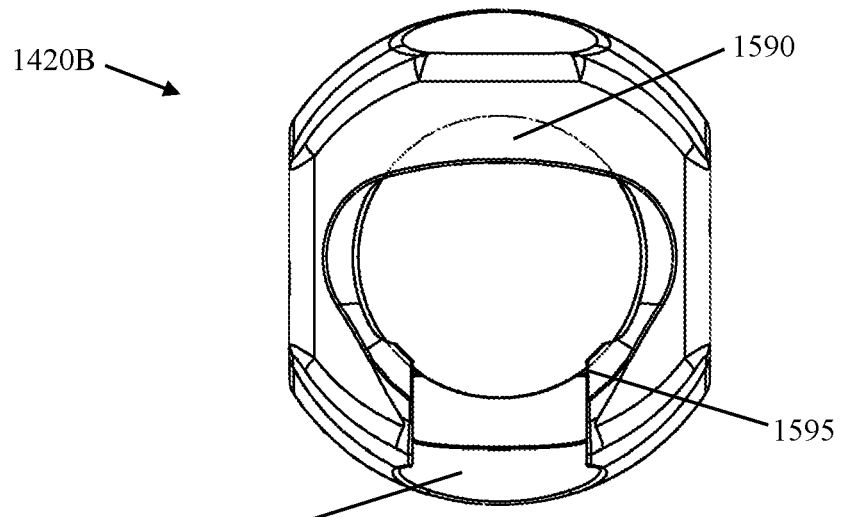
FIG. 16B shows a top view of an exemplary second receiver, per embodiments herein.
Figure 16C:
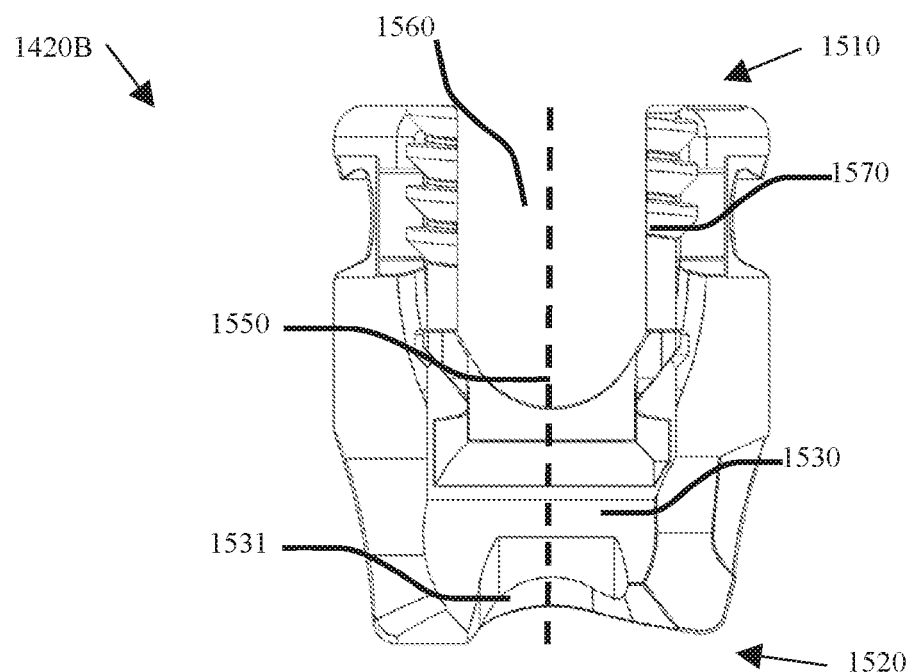
FIG. 16C shows a cross sectioned view of an exemplary second receiver, per embodiments herein.
Figure 16D:
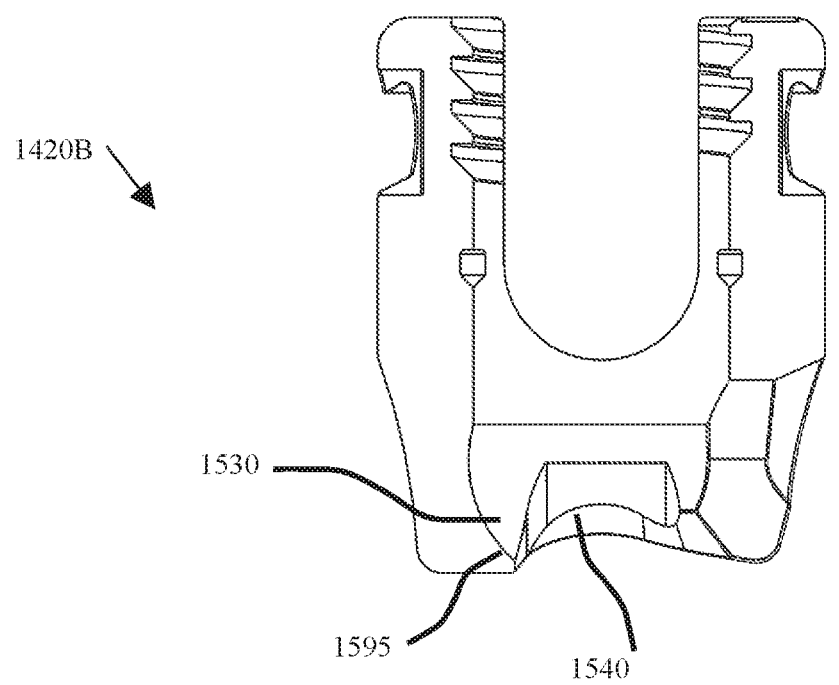
FIG. 16D shows a cross sectioned view of an exemplary second receiver, per embodiments herein.
Figure 16E:
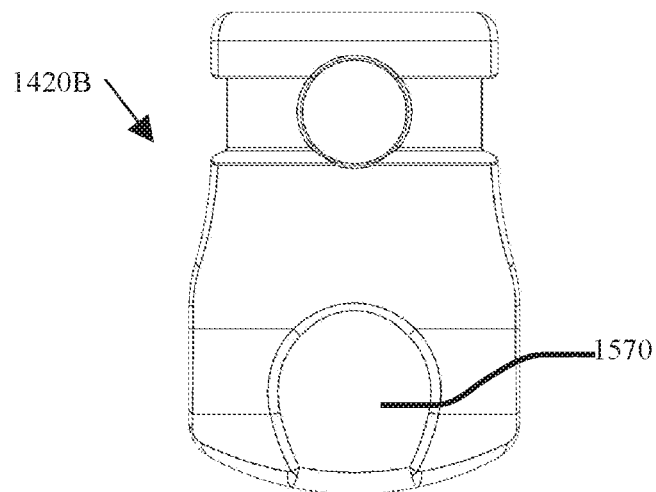
FIG. 16E shows a side view of an exemplary second receiver, per embodiments herein.
Figure 16F:
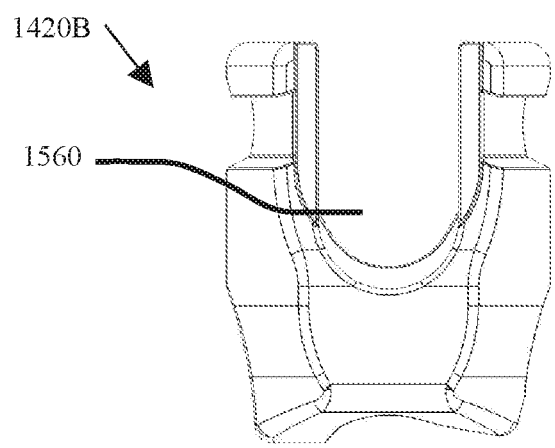
FIG. 16F shows a side view of an exemplary receiver, per embodiments herein.
Figure 16G:
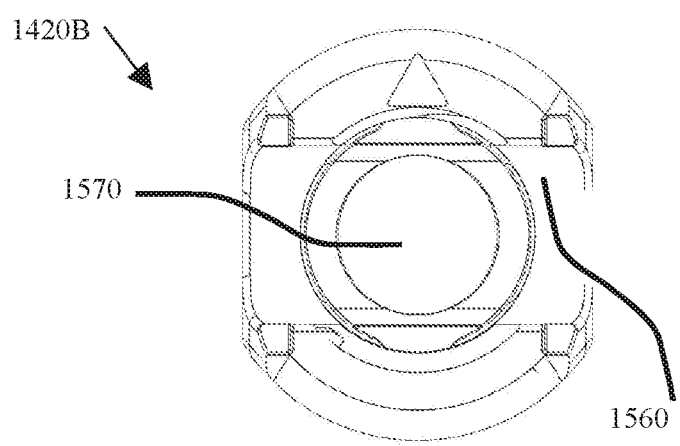
FIG. 16G shows a top view of an exemplary receiver, per embodiments herein.

With further reference to FIG. 1A, the assembly fastener 18 may further include at least a threaded surface 68 and a compression drive feature 20. In some embodiments, the compression drive feature 20 extends completely through the fastener 18, but in other embodiments, the compression drive feature 20 may comprise a blind recess in upper surface of the fastener 18. The fastener 18 may engage a longitudinal connecting member 21, such as a rod having a cylindrical surface 22 shown in FIGS. 1A, 5, and 6. In some embodiments, the fastener 18 includes a compression bottom surface 160 that presses against the connecting member 21 that in turn presses upon the compression structure 12 that in turn presses the screw head member 8 into fixed frictional contact with the receiver 10, so as to lock or fix the connecting member 21 relative to the vertebra (not shown). In some embodiments, the receiver 10 and the screw 4 cooperate in such a manner that the receiver 10 and the screw 4 can be secured at any of a plurality of angles, articulations, or rotational alignments relative to one another and within a selected range of angles both from side to side and from front to rear, to enable flexible or articulated engagement of the receiver 10 with respect to the screw 4 until both are locked or fixed relative to each other near the end of an implantation procedure. The enabled profile of articulation is shown in FIG. 13.

Figure 4:
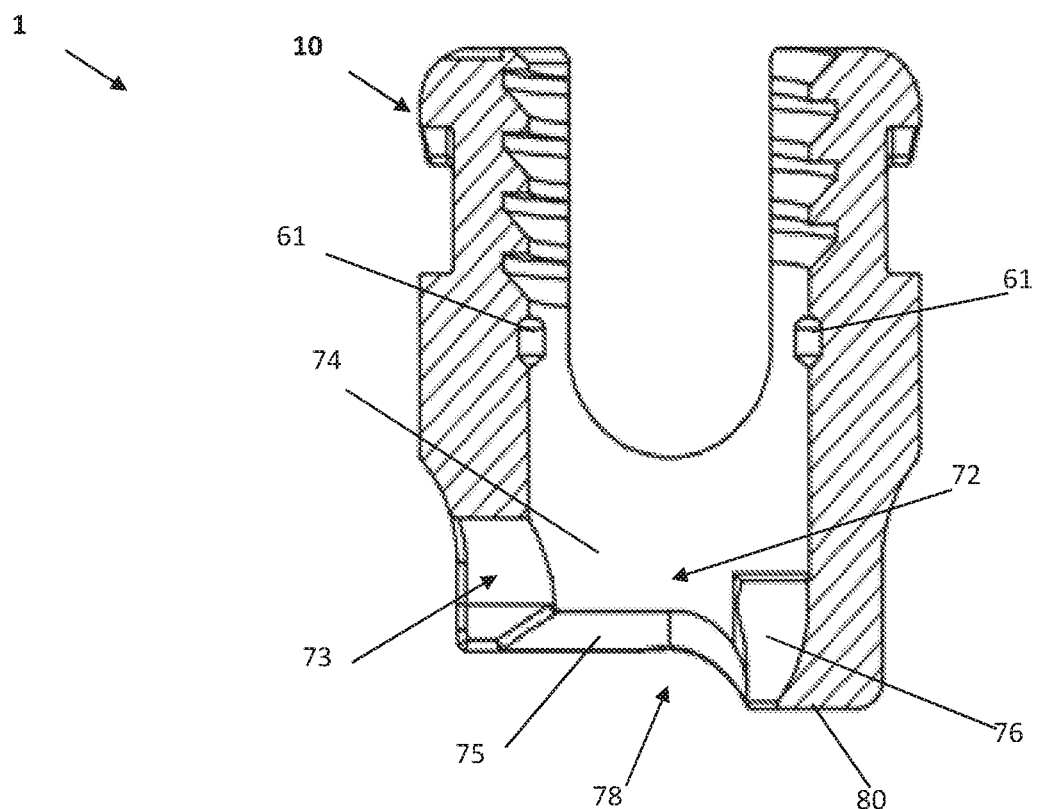
FIG. 4 shows a cross section of the exemplary receiver of FIG. 1A taken along the long axis of the receiver.

In some embodiments, per FIGS. 1A, 2, and 4, the receiver 10 may have a generally squared-off U-shaped profile with a partially cylindrical inner profile and a substantially faceted cylindrical outer profile. Alternatively, the outer profile could also be of another configuration, for example, curved, faceted, or rectilinear. screw head member 8 shows the screw 4 in an orientation that corresponds to an entry position relative to the receiver 10 where the head member 8 is aligned for insertion into a contoured volume within the receiver and the neck 30 of the screw will be received in an entry opening at the bottom of the receiver. In this view a receiver axis of rotation B (defined in the central bore of the receiver), as shown in FIG. 1A, may be generally perpendicular to the long axis of rotation A of the screw 4, as shown in FIG. 1B during assembly of the receiver 10 with the set screw 4, and the assembly 1 may be implanted in a vertebra (not shown), the axis B may be typically disposed at an angle of less than 90° with respect to the axis A of the screw 4.

In some embodiments, per FIG. 1A and FIG. 1B, the receiver 10 includes a base 58 and pair of spaced and generally parallel arms 60 that form an open generally U-shaped channel 62 there between that may be open at distal ends 64 of the arms. In some embodiments, the receiver arms 60 each include radially inward or interior surfaces that have a discontinuous guide and advancement structure 66 mateable with threaded surface 68 on the fastener 18. The guide and advancement structure 66 is shown as interrupted internal threads which mate with external threads on the fastener, but, more particularly may act as a buttress thread, a square thread, a reverse angle thread, a partial helically wound flange form configured to mate under rotation with a similar structure on the fastener 18 or other thread like or non-thread like helically wound advancement structure for operably guiding under rotation and advancing the fastener 18 downward between the receiver arms and having such a nature as to resist (or at least not to contribute to) splaying of the receiver arms 60 when the fastener 18 is advanced there between. In some embodiments, the base 58 and the arms 60 forming the U-channel 62 may be comprised of one or more components. For example, while in the illustrated embodiments, the base 58 and the arms 60 comprise a single component, in other embodiments, the base 58 may be a separate component in rotational or translational articulation with the arms 60 and the U-shaped channel 62. In some embodiments, the receiver arms 60 include opposed tool engaging divots 70 formed on or through outer surfaces of such arms as well as opposed tool engaging grooves 71. The divots 70 and/or grooves 71 may be used for holding the receiver 10 during assembly with the screw 4, during the implantation of the screw shaft body 6 into a vertebra and assembly with the rod 21 and the fastener 18. In some embodiments, the tool-receiving grooves or apertures may be configured in a variety of shapes and sizes and be disposed at other locations on the receiver arms 60.

With further reference to FIGS. 1A, 1B, 2, and 4, a chamber or cavity, 72, defined in part by an inner substantially cylindrical surface 74 and including a substantially spherical seating surface portion 76 may communicate with and located beneath the U-shaped channel 62 of the receiver 10 at the base portion 58 thereof. In some embodiments, the cylindrical surface 74 that defines a portion of the cavity 72 opens upwardly into the U-shaped channel 62 and includes opposing compression structure retention features 61 (shown in FIG. 4). In the illustrated embodiment, the compression structure retention features 61 may include partial radial grooves one on each side of the channel 62, but in other embodiments, the retention features are may comprise grooves, holes, fins, bosses, projections or other structures that may be utilized for the purpose of preventing disassembly of a compression structure from the receiver 10.

The seating surface portion 76 that is located below the inner cylindrical surface 74 is sized and shaped for mating with the spherical body 34, which is a portion of the head member 8 of the screw 4 as will be described in greater detail below. The seating surface portion 76 communicates with a lower opening (i.e. a terminal opening) 78 that communicates with both the cavity 72 and a receiver lower exterior or bottom surface 80 of the base 58. The terminal opening 78 is substantially coaxially aligned with respect to the rotational axis B of the receiver 10. The opening 78 has a generally circular shape that is partially occluded by a keyed feature 63 (shown in FIG. 2), and is configured to pass the screw head member 8 into and out of the contoured volume of the cavity 72 only when the shaft keyed portion 38 is aligned with the receiver keyed feature 63. In this embodiment, the keyed feature 63 further includes a relief 77 which forms a portion of a circle coaxial with the long axis of the receiver to accommodate the screw neck 30. The presence or absence of the relief 77 depends in part on the distance that the shoulder forming the keyed feature 63 extends into the circular shape of the terminal opening 78. The bottom edge of the terminal opening 78 includes chamfers 75 that allow increased angulation of the screw shaft 4 in preferred directions when assembled into receiver 10. Chamfers 75 do not encroach on the keyed feature 63.

The surface portion 76 further communicates with an entry opening 73 (as shown in FIG. 2 and FIG. 4) that communicates with the contoured volume of the cavity 72, as well as the terminal opening 78 and a receiver side exterior. In the illustrated embodiment, the entry opening 73 is located opposite the receiver keyed feature 63 and is shaped to allow the screw neck 30 to reside therein to allow the screw 4 to assume the entry position in the assembly/disassembly orientation where the screw long axis is generally perpendicular to the receiver long axis and the screw keyed portion 38 and the receiver keyed feature 63 are aligned (and engaged with the other) allowing the screw head member 8 to pass into and out of the contoured volume of the cavity 72.

In the first illustrated embodiment, the receiver only has one entry opening 73 (i.e. on a single side) and the screw head member 8 can only enter the cavity 72 at substantially one entry angle of screw long axis with respect to the receiver axis, although at that entry angle, the screw head member 8 can enter the cavity 72 at any orientation rotated around the screw long axis. In other embodiments, for example shown in FIG. 10, the receiver may have more than one side opening and more than one entry angle between the screw shaft axis and the receiver axis, furthermore, the screw head 408 may need to be in a specific rotational orientation around the shaft long axis in order to enter or leave the cavity 672.

Figure 3A:
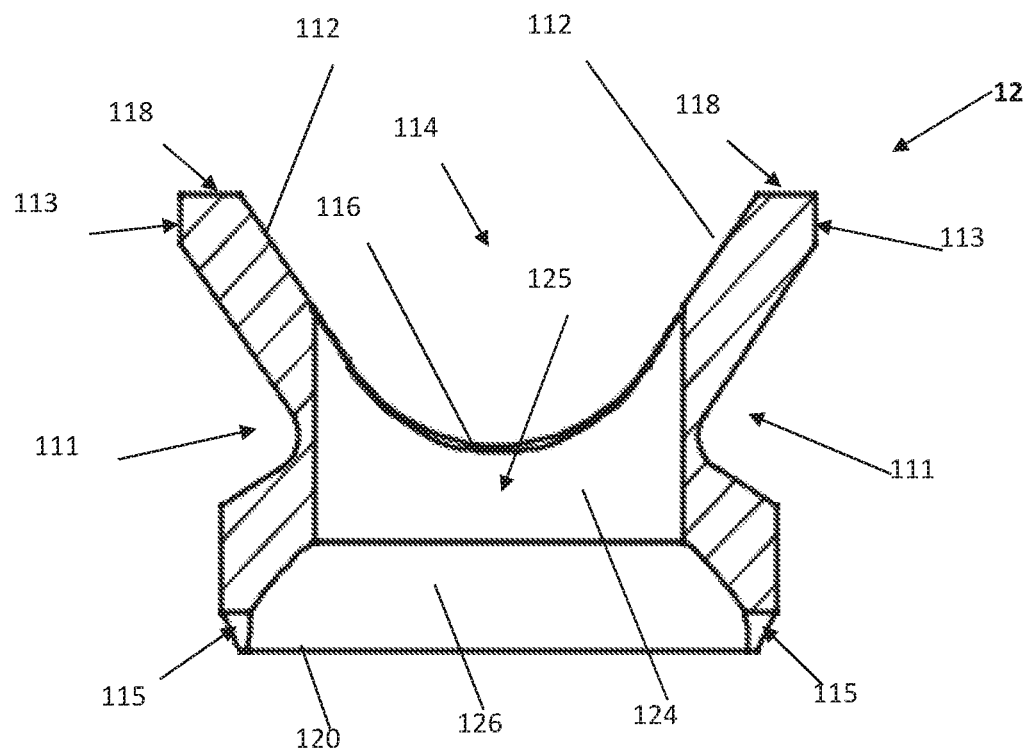
FIG. 3A shows a cross section of an exemplary compression insert of FIG. 1A.
Figure 3B:
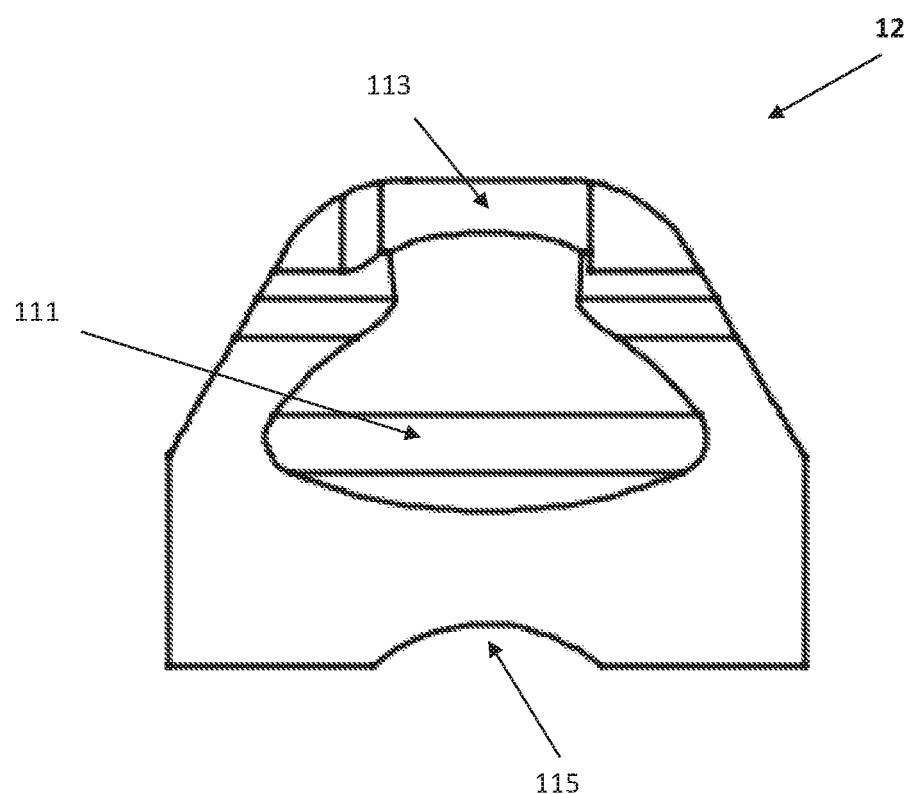
FIG. 3B shows a cross section of the exemplary compression insert of FIG. 3A at 90°.

The first embodiment of the compression structure 12 is best illustrated in FIGS. 1A, 3A, and 3B. In this embodiment, the compression structure 12 includes a body 110 of substantially circular cross section integral with a pair of upstanding arms 112. The body 110 and arms 112 form a generally U-shaped, open channel 114 having a substantially U-shaped bottom rod seating surface 116 having a radius substantially conforming or slightly undersized to a radius of the rod 21 and thus configured to operably snugly engage the rod 21. The arms 112 disposed on either side of the channel 114 each included a top surface 118 that is parallel to a bottom surface 120. Each upstanding arm 112 further includes a relief cut 111 (best seen in FIG. 3A and FIG. 3B) designed to thin the arms 112 and allow them to flex slightly during assembly of compression structure into the receiver 10. The compression structure 12 includes a substantially cylindrical outer surface 122 and an inner cylindrical wall 124 defining a central through-bore 125 extending along a central axis C of the compression structure 12. The outer surface 122 further includes protrusions 113 (best seen in FIG. 3A and FIG. 3B), one on each of the upstanding arms 112 and proximal to their top surfaces 118. The top surface 118 and the bottom surface 120 are disposed perpendicular to the axis C. Extending between the inner cylindrical wall 124 and the bottom surface 120 is a curved or spherical inner surface 126 sized and shaped to frictionally engage and mate with the outer spherical body 34 of the head member 8 of the screw 4.

Figure 5:
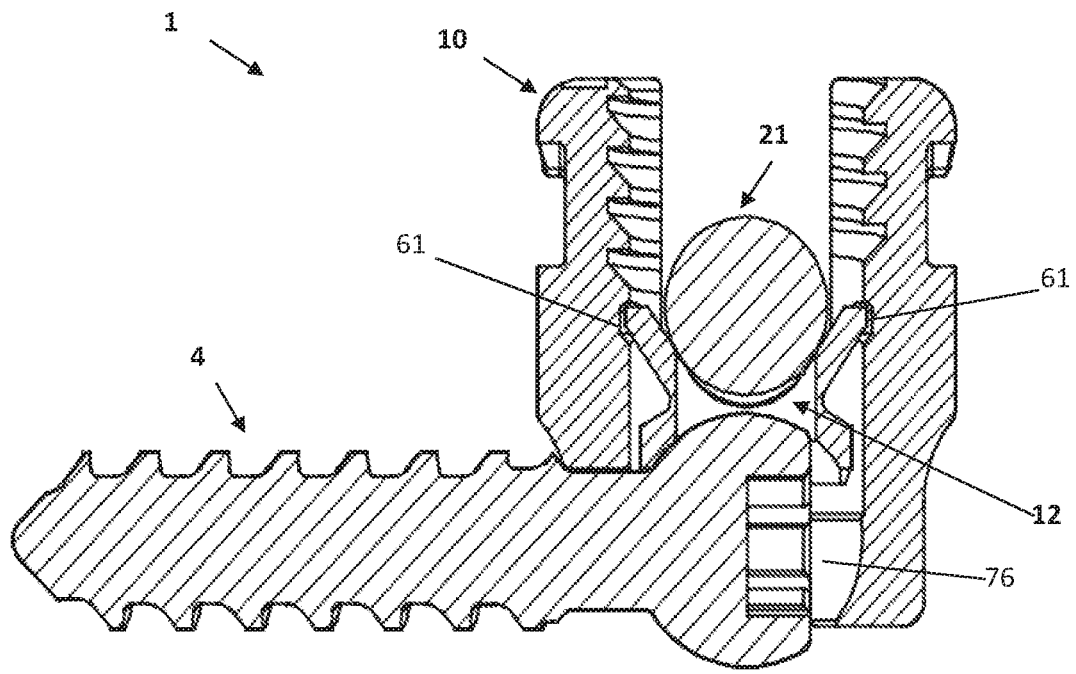
FIG. 5 shows a cross section of the exemplary spinal assembly of FIG. 1 taken along the long axis and with the screw in an entry position for insert in the receiver and with the compression insert in a closed position and including a compression structure.
Figure 6:
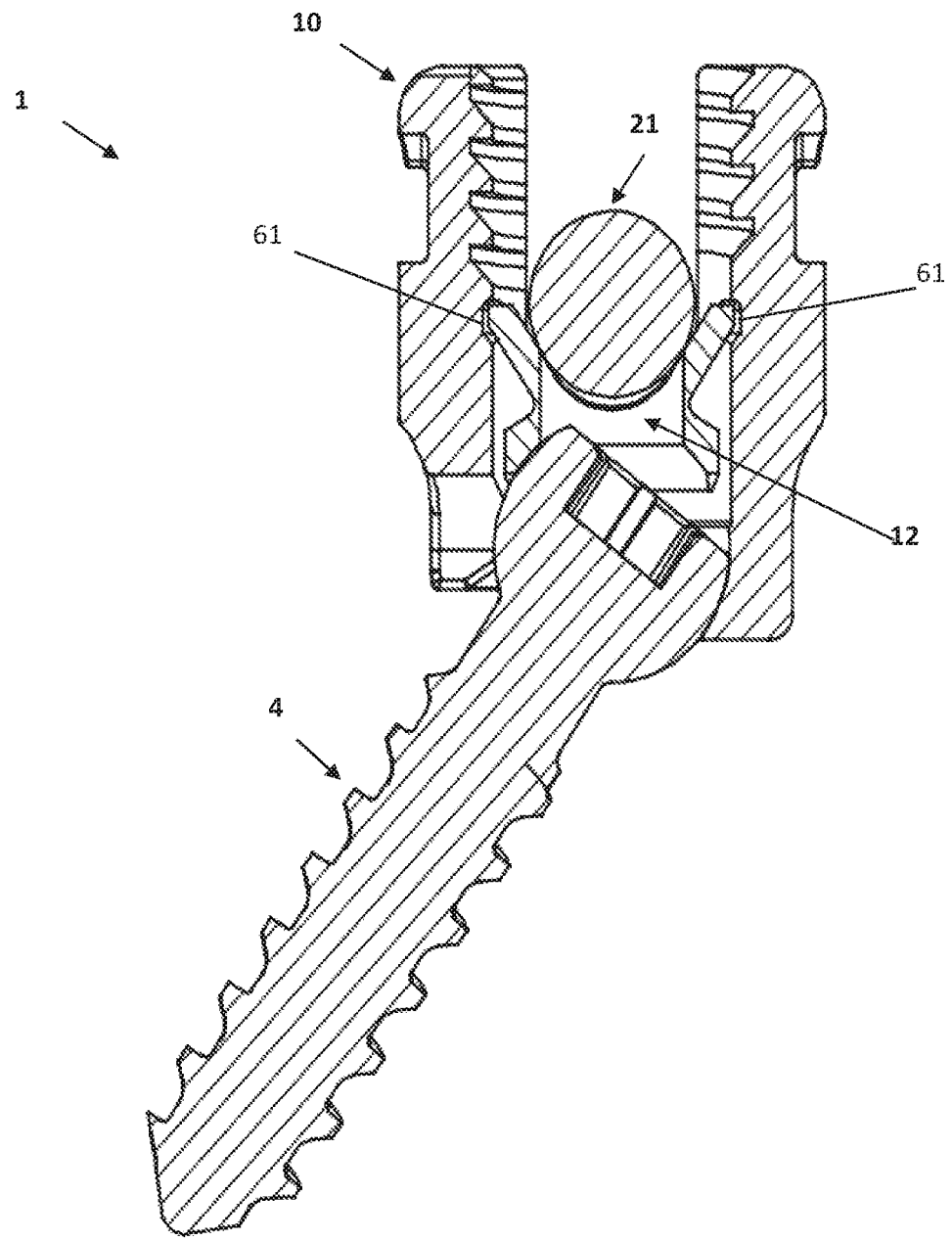
FIG. 6 shows a cross section of the exemplary spinal assembly of FIG. 5 with the screw in an operable position captured in the receiver.

The cylindrical outer surface 122 of the compression structure 12 has a diameter slightly smaller than a diameter between crests of the threads of the receiver guide and advancement structure 66, but the protrusions 113 form a diameter that is slightly larger than the diameter between crests of the threads of the guide and advancement structure 66 of the receiver 10. This allows the compression structure 12 to be top-loaded into the receiver 10 by means of the upstanding arms deflecting slightly inward during assembly as the compression structure is advanced into the receiver 10 until the protrusions 113 reach the retention features (i.e. recesses) 61 of the receiver 10 and are allowed to spring outward and engage the retention features 61 as seen in FIG. 5. At this stage, the compression structure 12 is detained inside the receiver 10 and prevented from coming back out through the top of the receiver 10, while also being allowed some ability to move downward under load in order to press upon the screw head, with or without deflection of the arms 112.

The cylindrical surface 122 of the compression structure 12 has a diameter and a height measured from the top surface 118 to the bottom surface 120 are sized such that the compression structure 12 is received within the cylindrical surface 74 of the receiver 10 below the guide and advancement structure 66, but the bottom surface 120 thereof does not engage the spherical seating surface 76 of the receiver 10. When fully installed, with the screw 4 assembled in the receiver 10, the inner surface 126 of the compression structure 12 is pressed upon by the connecting member 21, which causes it to frictionally engage the spherical body 34 of the head member 8 of the screw 4 which in turn presses upon the seating surface portion 76 of the receiver 10. It is foreseen that the compression structure 12 may take on a variety of different configurations and means of retention inside the receiver 10.

Figure 8:
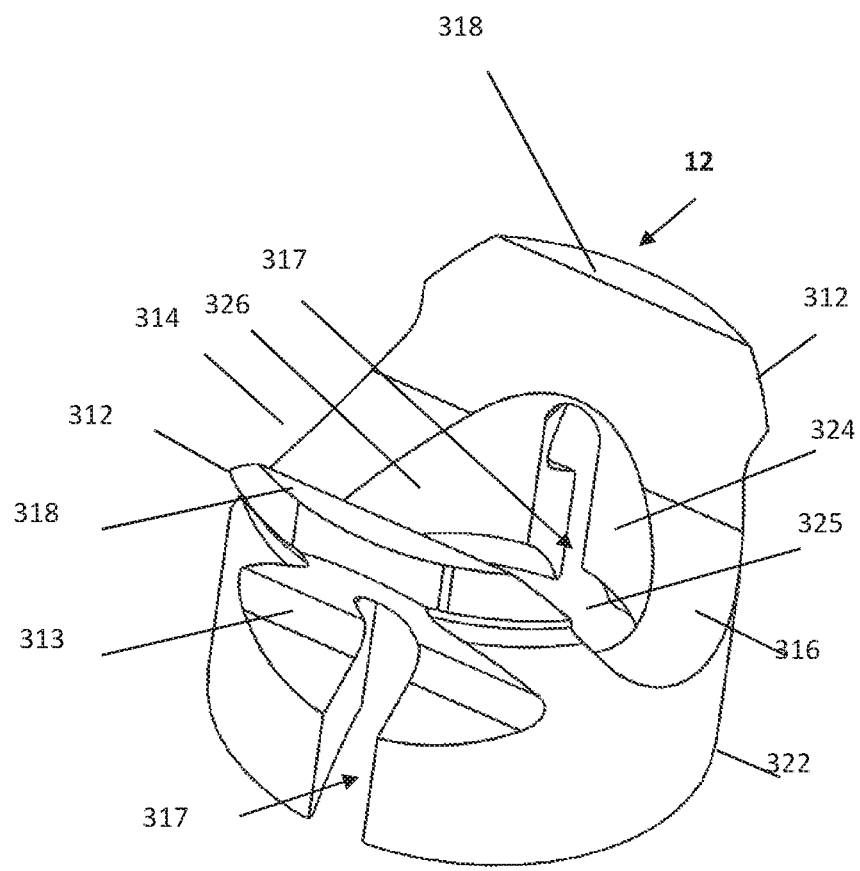
FIG. 8 shows another embodiment of an exemplary compression insert.

Additionally, other embodiments of the compression structure such as the compression structure 12 shown in FIG. 8 may include features designed to produce "drag" on the screw shaft producing slight resistance when the shaft is angulated within the receiver. This structure includes the same features as the first embodiment such as, for example, a body of substantially circular cross section integral with a pair of upstanding arms 312 which together form a generally U-shaped, open channel 314 having a substantially U-shaped bottom rod-seating surface 316 having a radius substantially conforming or slightly undersized to a radius of the connecting member 21 so as to engage the connecting member 21 and the arms 312 disposed on either side of the channel 314 each including a top surface 318 that is parallel to a bottom surface. The arms are configured to allow them to flex slightly during assembly of compression structure into the receiver 10 for the same assembly relationship with the receiver 10. The compression structure 12 includes a substantially cylindrical outer surface 322 and an inner cylindrical wall 324 defining a central through-bore 325 extending along a central axis C of the compression structure 12. The compression structure includes protrusions 313 on each of the upstanding arms 312. Extending between the inner cylindrical wall 324 and the bottom surface is a curved or spherical inner surface sized and shaped to frictionally engage and mate with the outer spherical body 34 of the head member 8 of the screw 4. In this instance, the compression structure includes one, or a pair, of opposing slots 317 which allow the curved inner surface to generate drag between the screw's spherical head and the rest of the assembly. his is accomplished the spherical diameters of the screw and compression structure being machined equal, but, prior to assembly, the compression structure is deformed slightly by collapsing the slot 317, which has the effect of making the surface 326 of the compression structure have slightly non-spherical shape. Thus, when it is forced against the true spherical shape of the screw head, it forces the slot 317 to open/flex outward again allowing for spherical contact and this flexing of the slot results in friction fit. It should be understood that the compression member may be shaped in ways other than the illustrated embodiments so long as it has a spherical surface for contacting the screw head, is able to be retained inside the receiver, and is capable of at least some downward translation in order to exert force onto the screw head to lock the screw angle relative to the receiver.

As shown in FIG. 1A, the stabilizer or longitudinal connecting member 21 that is utilized with the assembly 1 can be any of a variety of implants utilized in reconstructive spinal surgery, and is illustrated as a cylindrical elongate structure or rod having a cylindrical surface 22 of uniform diameter and having a generally smooth surface. The longitudinal connecting member 21 may be made from metal, metal alloys, or other suitable materials, including plastic polymers such as polyetheretherketone (PEEK), ultra-high-molecular weight polyethylene (UHMWP), polyurethanes, and composites. The illustrated longitudinal connecting member 21 is preferably sized and shaped to snugly seat near the bottom of the U-shaped channel 62 of the receiver 10 and, during normal operation, is positioned slightly above the bottom of the channel 62. In particular, the longitudinal connecting member 21 normally, directly or abuttingly, engages top seating surface 116 of the compression structure 12 and biases the compression structure 12 against the domed upper portion of the screw head member 8, consequently biasing the screw head member 8 downwardly and into fixed frictional contact with the internal spherical surface 76 of the receiver when the assembly 1 is fully assembled. The screw 4 is thereby locked or held in position relative to the receiver 10 by the longitudinal connecting member 21 firmly pushing downward on the top seating surface 116 of the compression structure 12 as illustrated, for example, in FIG. 6.

Stabilizers or longitudinal connecting members may take a variety of shapes, including, but not limited to, rods or bars of oval, rectangular, or other curved or polygonal cross-section. Furthermore, the stabilizer 21 may be a component of a longer overall dynamic stabilization connecting member, with cylindrical or bar-shaped portions sized and shaped for being received by the receiver 10 that may have a U- or rectangular-shaped channel for closely receiving the longitudinal connecting member. The connector 21 may be integral or otherwise fixed to a bendable or damping component that is sized and shaped to be located between adjacent pairs of bone screw assemblies 1, for example. Such a rod or bar component (as may the other components) may be made from a variety of materials including metal, metal alloys, or other suitable materials, including, but not limited to plastic polymers such as polyetheretherketone (PEEK), ultra-high-molecular weight-polyethylene (UHMWP), polyurethanes and composites, including composites containing carbon fiber, ceramics or metal alloys, as well as resorbable materials, such as polylactic acids.

With reference to FIG. 1A, the fastener 18 can be any of a variety of different types of closure structures for use in conjunction with the present invention with suitable mating structure on the upstanding arms 60 of the receiver 10. In the embodiment shown, the fastener 18 is threadably received between the spaced arms 60. The fastener 18 includes the helically wound threaded surface 68 that is sized, shaped and positioned so as to engage and interlock with the guide and advancement structure 66 on the arms 60 to provide for rotating advancement of the fastener 18 into the receiver 10 when rotated clockwise and, in particular, to cover the upwardly open portion of the U-shaped channel 62 near the arm ends 64 to capture the longitudinal connecting member 21 without splaying or minimizing the splaying of the arms 60. The threaded surface 68 utilized in accordance with the present invention may take a variety of forms, including the illustrated substantially buttress thread. Alternatively, the fastener may include an internal guide and advancement structure which mates with an external guide and advancement member on the receiver.

The fastener 18 includes a compression bottom surface 160 for engaging the surface 22 of the connecting member 21. The fastener 18 operably biases against the connecting member 21 by advancement and applies pressure to the stabilizer 21 under torqueing, so that the stabilizer 21 is urged downwardly against the compression structure top seating surface 116. In the illustrated embodiment, downward biasing of the compression structure 12 operably produces a frictional engagement between the stabilizer 21 and seating surface 116 of the compression structure 12 and also urges the compression structure 12 toward the base 58 of the receiver 10, so as to frictionally seat the compression structure spherical inner surface 126 fixedly against the spherical surface 34 of the screw head 8, also fixing the screw 4 in at a selected angle and in a rigid position relative to the axis B of the receiver 10.

FIG. 7 illustrates an alternative embodiment of the invention in which the receiver 10 is the same as the receiver of FIG. 1A, but the screw 204 varies by having a variation of the keyed portion 238 which has a more complex configuration than as previously described. In particular, in this configuration, opposing co-planar flat surfaces 236 are cut at a location nearer the circumference of the spherical head member 208 of the screw 204 and spaced radially equally from them, areas of the spherical head member are left, for example, to the place axially inward where the drive feature dictates that the spherical portion needs to be removed to allow this feature in the screw head member 208, The remaining arched areas 239 include a 2-dimensional profile that corresponds in shape to the relief 77 that is provided in the shoulder forming the keyed portion 238 of the receiver 10. The relationship between the screw head member 208 and the receiver 210 is the same in the embodiment shown in FIG. 9, and the receiver 210 is essentially the same as the receiver 10, except that the entry opening 273 and the keyed portion 238 formed in the terminal opening 278 are each located 90° radially from the axis of the U-shaped channel 262 relative to the orientation of the entry opening and keyed portion 238 in the receiver 210. Other aspects of the receiver 210 are the same as the receiver and relationship with the remaining components of the assembly. The receiver 210 includes a base 258 and pair of spaced and generally parallel arms 260 that form an open generally U-shaped channel 262 there between that is open at distal ends 264 of the arms. The receiver arms 260 each include radially inward or interior surfaces that have a discontinuous guide and advancement structure 266 mateable with threaded surface 68 on the fastener 18. In this embodiment, the receiver 210 includes a spherical recess sized and shaped for mating with the spherical body 234 which is a portion of the head member 208 of the screw 204. Again, the seating surface portion communicates with a lower opening (i.e. a terminal opening) 278 that communicates with both the cavity and a receiver lower exterior or bottom of the base 258 of the receiver 210. The terminal opening 278 is substantially coaxially aligned with respect to the rotational axis B of the receiver 210. The opening 278 has a generally circular shape that is partially occluded by a keyed feature 263, and is configured to pass the screw head member 208 into and out of the contoured volume of the cavity only when the shaft keyed portion 238 is aligned with the receiver keyed feature 263. In this embodiment, the keyed feature 263 further includes a relief 277 which forms a portion of a circle coaxial with the long axis of the receiver and to accommodate the screw neck 230, but in other embodiments this relief may not be present. The bottom edge of the opening 278 includes chamfers 275 that allow increased angulation of the screw shaft 206 in preferred directions when assembled into receiver 210. Chamfers 275 do not encroach on the keyed feature 263.

The seating surface portion further communicates with an entry opening 273 that communicates with the contoured volume of the cavity, as well as the terminal opening 278 and a receiver side exterior. In the illustrated embodiment, the entry opening 273 is located opposite the receiver keyed feature 263 and is shaped to allow the screw neck 230 to reside therein to allow the screw 204 to assume the entry position in the assembly/disassembly orientation where the screw long axis is generally perpendicular to the receiver long axis and the screw shaft keyed portion 238 and the receiver keyed feature 263 are aligned (and engaged with the other) allowing the screw head member 208 to pass into and out of the contoured volume of the cavity.

Figure 10:
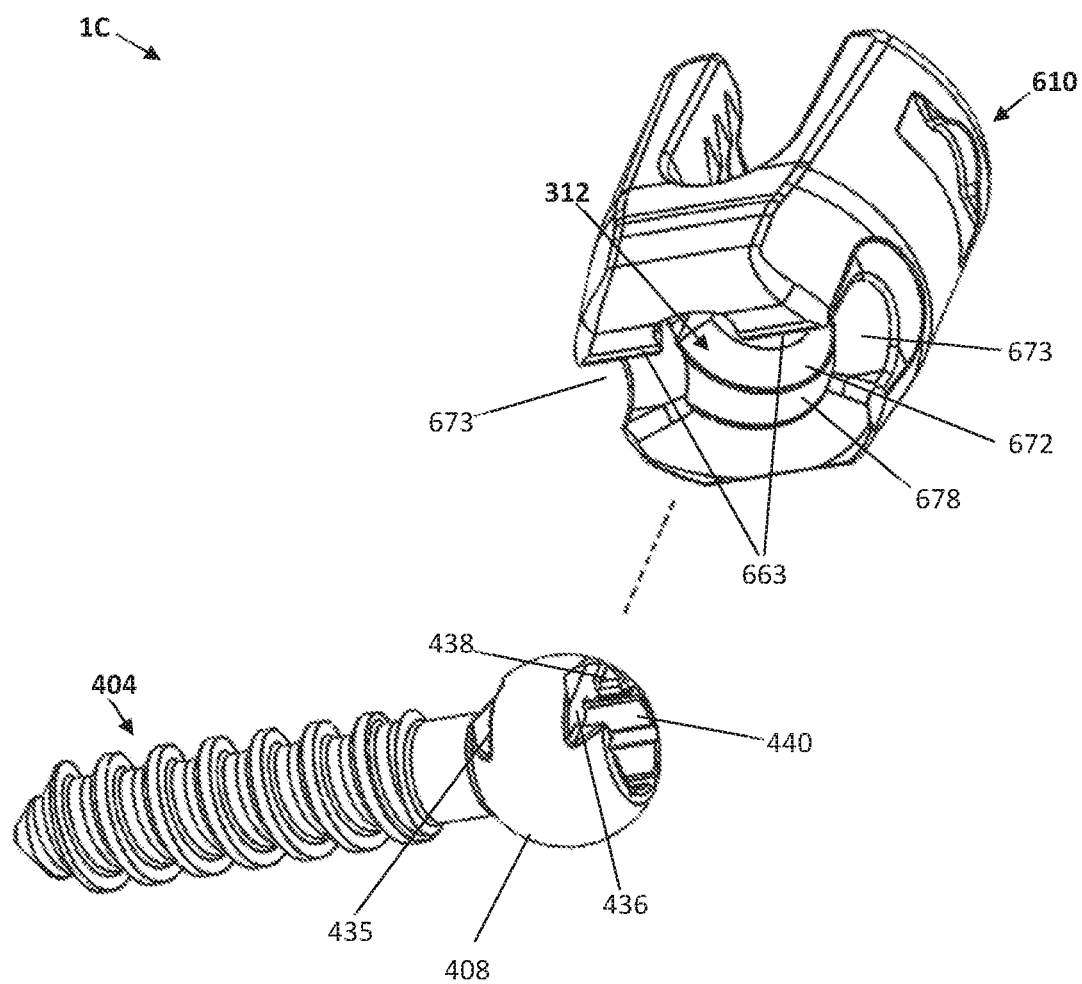
FIG. 10 shows a third embodiment of an exemplary anchor assembly and screw wherein the receiver comprises two entry openings.
Figure 11A:
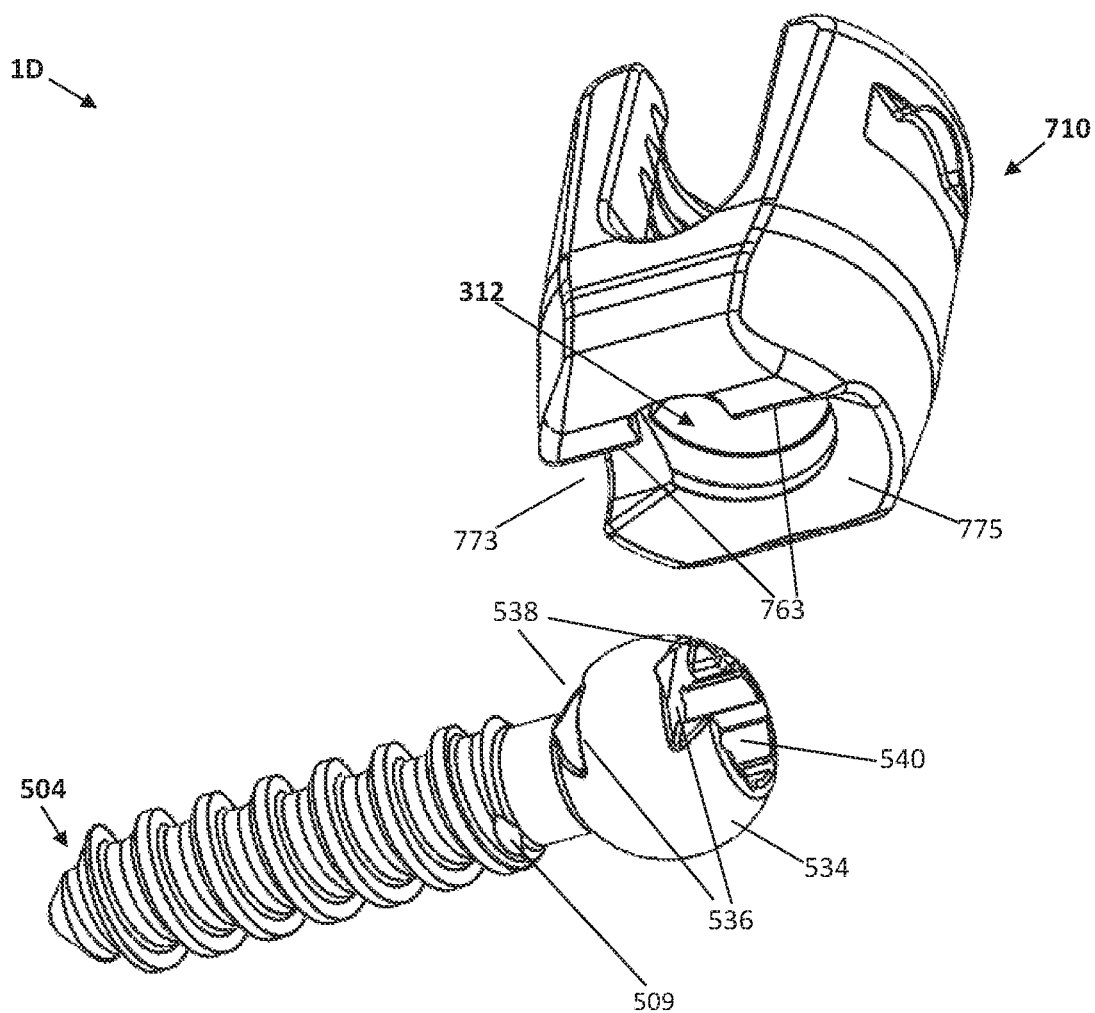
FIG. 11A shows an alternative embodiment of an exemplary anchor assembly and screw of FIG. 1.
Figure 11B:
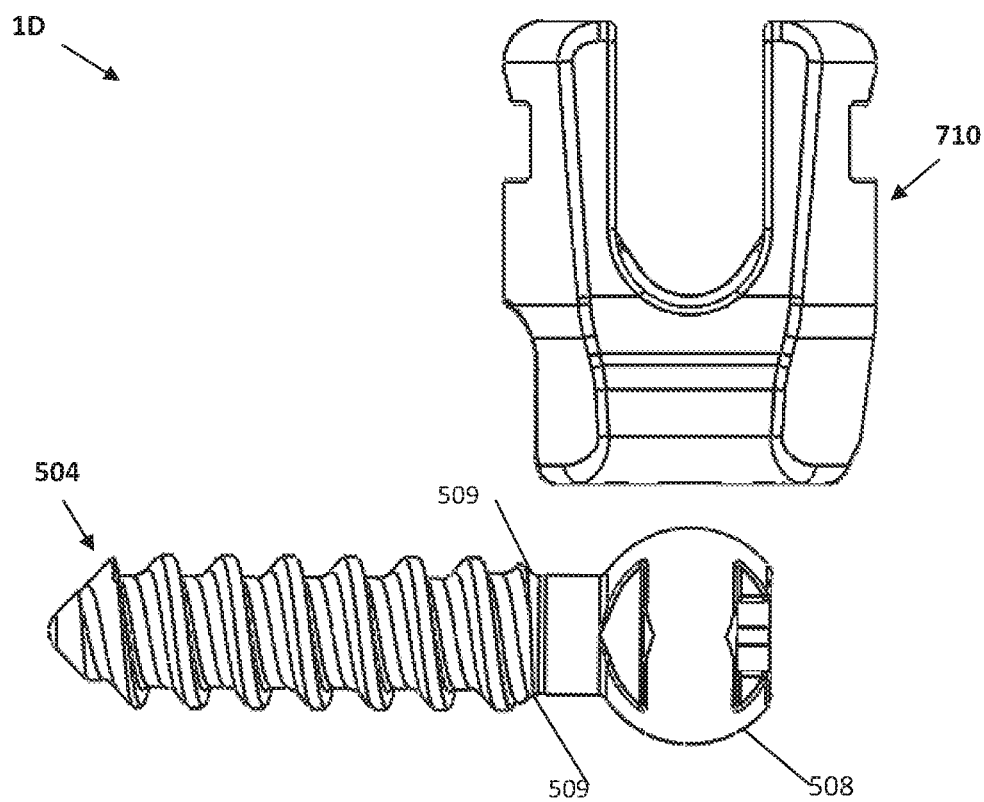
FIG. 11B illustrates a detail of the embodiment of the exemplary anchor assembly of FIG. 11A with the screw outside of the receiver.
Figure 11C:
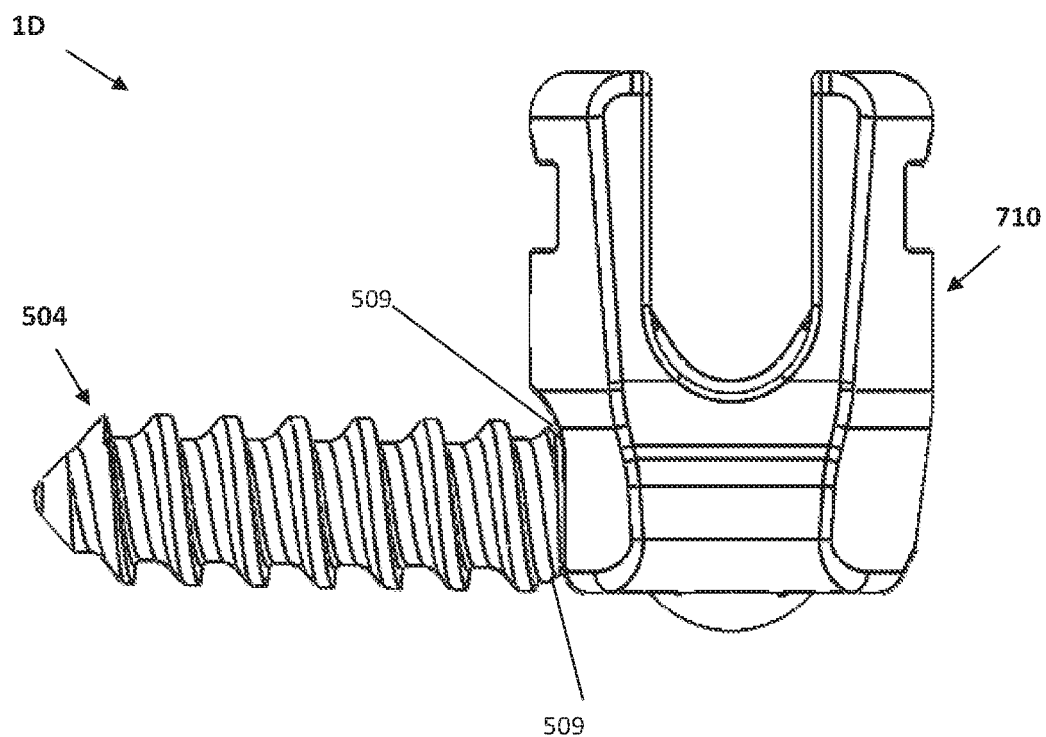
FIG. 11C shows detail of the embodiment of the exemplary anchor assembly of FIG. 11B with the screw in the entry position in the receiver.
Figure 11D:
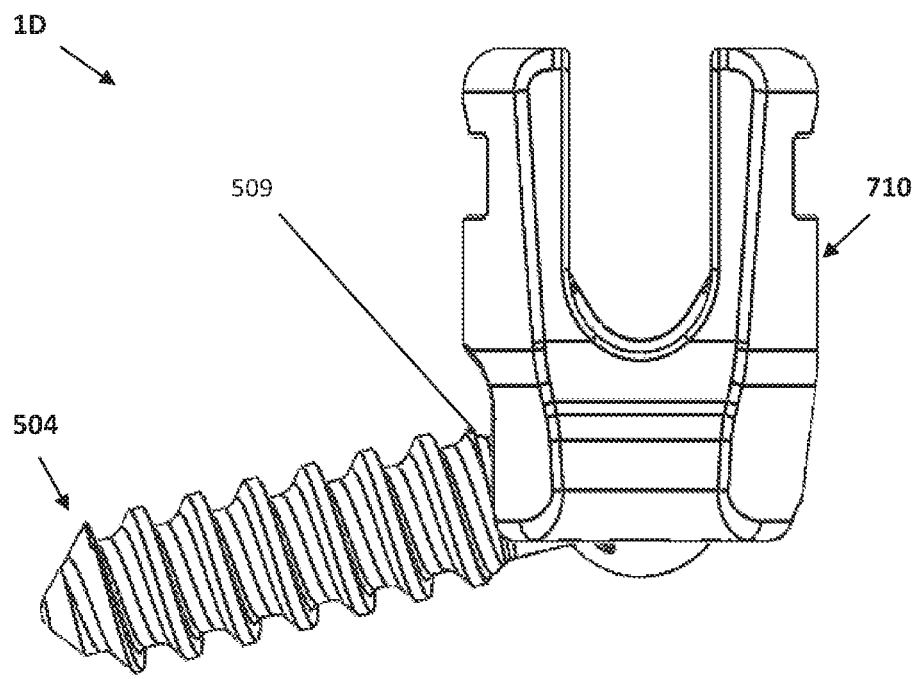
FIG. 11D shows detail of the embodiment of the exemplary anchor assembly of FIG. 11B illustrating a relief feature in the thread run out of the screw.
Figure 12:
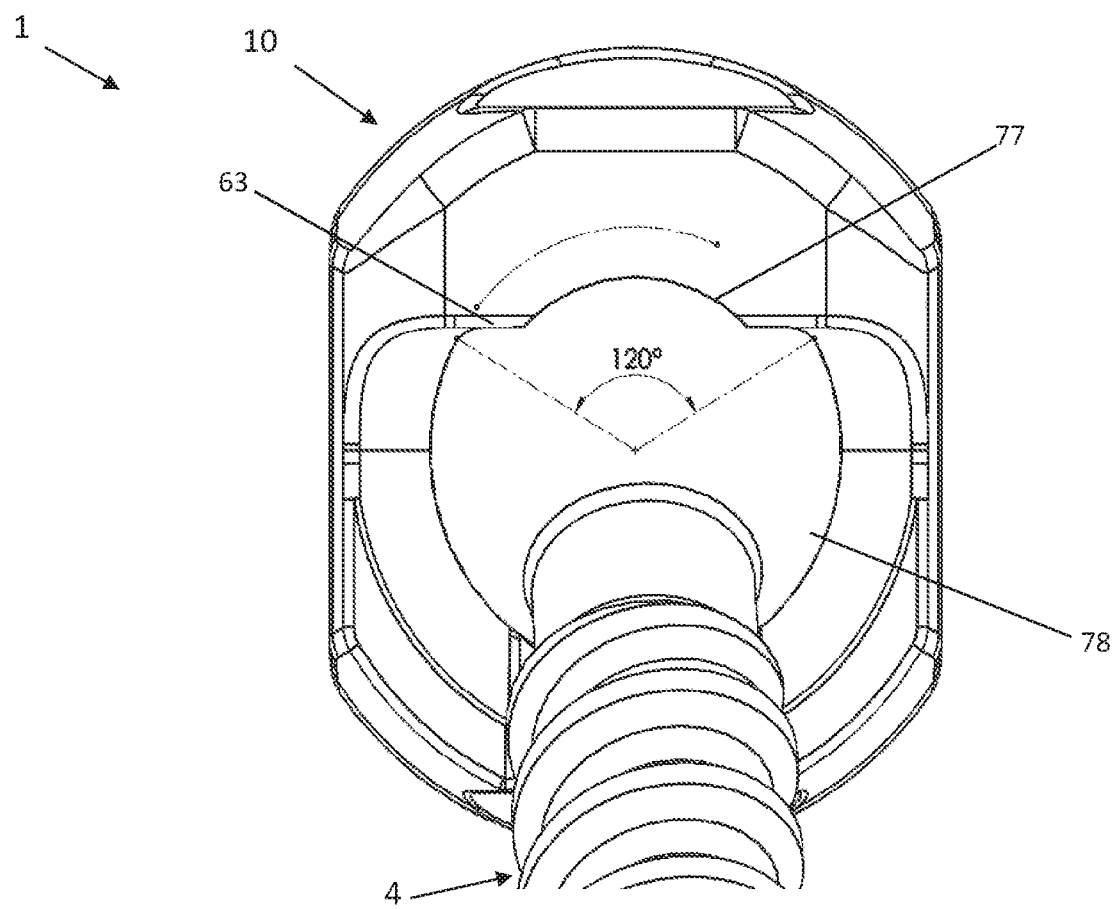
FIG. 12 shows a bottom view of an exemplary restraining member holding the screw in the rod receiver.

In FIG. 10, an embodiment of the receiver is shown in which the receiver 610 has two entry openings 673 spaced radially opposite for the insertion of the screw 404 in one of two first positions and in this instance the keyed portions of the screw head are a top 436 and a bottom 435 flat transverse to the direction of the longitudinal axis which mate with keyed features 663 in the interference shoulder at a corresponding location in the terminal opening 678 opening or screw head volume. A similar relationship is shown between the similar keyed portion of the screw 504 and the keyed feature 763 of the receiver 710 (shown in FIGS. 11A-11D), and the function is the same, except that the receiver 710 has a single entry opening 773. The opening in all cases is slightly larger than the circumference of the screw head, but the shoulder or keyed area closes the opening to retain the screw head in the spherical volume when it is in the operable position. The keyed feature 763 is further configured to prohibit the screw from pivoting down from its entry position into operable position when the keyed features of screw and receiver are oriented for entry. This is accomplished by the lower corner of the receiver proximal to the entry opening 773 interfering with the screw 504 threads proximate to the screw neck when the screw is pivoted down from its entry position. The screw is only allowed to pivot into operable position if, after entering the receiver inner volume in entry position, it is then rotated 90 degrees around the screw long axis in order to align the reliefs 509 with the interference points of the receiver 710.

The ability to simply, quickly, and securely assemble screw fixators with the receivers allows for this step to be carried out intraoperatively, This has a number of important advantages both for intraoperative flexibility and convenience and for inventory and budgetary considerations as it allows a screw supplier to offer a much broader offering of screw shafts, receivers and rod offerings at a fraction of the cost of supplying each screw fully and permanently assembled. It is contemplated that a supplier may, for example, offer multiple types of receivers configured to accept various rod sizes (e.g. 3.0 mm, 3.5 mm, 4.0 mm, 4.5 mm, 5.0 mm, 5.5 mm, 6.0 mm, 6.5 mm), multiple types of screws (e.g. fully threaded, partially threaded, solid, cannulated, single lead, dual-lead, triple lead, quadruple lead, fenestrated for cement delivery, ceramic-coated, self-drilling, self-tapping, etc.) offered in multiple diameters (e.g. 3.5 mm, 4.0 mm, 4.5 mm, 5.0 mm, 5.5 mm, 6 mm, 6.5 mm, 7.0 mm, 7.5 mm, etc.) and length (e.g. 10 mm-120 mm). Furthermore, some or all of the types and sizes of receivers and screws may be offered in multiple material options (e.g. Commercially Pure Titanium, Titanium alloys, CoCrMo, Stainless Steel, etc.). One of the many possible combinations that is deemed useful is providing CoCrMo partially threaded screws used with Titanium allow receiver assembly for use in Occiput-C1, Occiput-C2 or C1-C2 fusions. Those skilled in the art should also realize that such equivalent constructions do not depart from the spirit and scope of the present disclosure, and that they may make various changes, substitutions, and alterations herein without departing from the spirit and scope of the present disclosure.

Provided herein, per FIGS. 14-23B is a polyaxial spinal anchor assembly 1400 comprising a bone anchor 1410 and a receiver 1420.

As seen in FIGS. 15A-E, an exemplary first receiver 1420A may comprise a first receiver end 1510, and second receiver end 1520, and a receiver axis 1550 from the first receiver end 1510 to the second receiver end 1520. The first receiver end 1510 may comprise a socket cavity 1530. The socket cavity 1530 may comprise a socket aperture 1531 and a socket cavity slot 1540.

In some embodiments, the receiver 1420A further comprises a compression element between the first receiver end 1510 and the second receiver end 1520. In some embodiments, the compression element is configured to transfer a force between the rod and the head. In some embodiments, the assembly 1400 further comprises a set screw. In some embodiments, the receiver 1420A further comprises a threaded bore 1570 configured to threadably receive the set screw. In some embodiments, the threaded bore 1570 is generally parallel to the receiver axis 1550. In some embodiments, the receiver 1420A further comprises a clearance channel 1580 within the socket aperture 1531. In some embodiments the clearance channel 1580 is configured to accept a mating feature in the head of the bone anchor 1410.

In some embodiments, the assembly 1400 further comprises a rod. In some embodiments, the receiver 1420A further comprises a rod slot 1560. In some embodiments, the rod slot 1560 is configured to accept the rod. In some embodiments, the rod slot 1560 is generally perpendicular to the receiver axis 1550.

As seen in FIGS. 16A-G, an exemplary second receiver 1420B may comprise a first receiver end 1510, and second receiver end 1520, and a receiver axis 1550 from the first receiver end 1510 to the second receiver end 1520. The first receiver end 1510 may comprise a socket cavity 1530. The socket cavity 1530 may comprise a socket aperture 1531 and a socket cavity slot 1540. In some embodiments, the receiver 1420B further comprises a compression element between the first receiver end 1510 and the second receiver end 1520. In some embodiments, the compression element is configured to transfer a force between the rod and the head. In some embodiments, the assembly 1400 further comprises a set screw. In some embodiments, the receiver 1420B further comprises a threaded bore 1570 configured to threadably receive the set screw. In some embodiments, the threaded bore 1570 is generally parallel to the receiver axis 1550. Per FIGS. 16B and 16D, the outline 1590 of the socket cavity 1530 and the interference areas 1595 can be seen. The interference areas 1595 may define a keyed contour of the cavity aperture.

In some embodiments, the assembly 1400 further comprises a rod. In some embodiments, the receiver 1420B further comprises a rod slot 1560. In some embodiments, the rod slot 1560 is configured to accept the rod. In some embodiments, the rod slot 1560 is generally perpendicular to the receiver axis 1550.

As seen in FIGS. 17A-I, an exemplary first bone anchor 1410A may have a first end 1710, a second end 1720, a longitudinal axis 1750, and a neck 1760. The longitudinal axis 1750 may be defined as spanning from the first end 1710 to the second end 1720. The neck 1760 may be positioned between the first end 1710 and the second end 1720. The neck 1760 may be configured to fit within the socket cavity slot. The neck 1760 may be configured to fit within the socket cavity slot when the receiver axis and the longitudinal axis 1750 are generally coplanar. The neck 1760 may have a diameter of less than a diameter of the head 1730. In some embodiments, the exemplary first bone anchor 1410A may be configured for use with the exemplary first receiver 1420A.

Figure 17A:
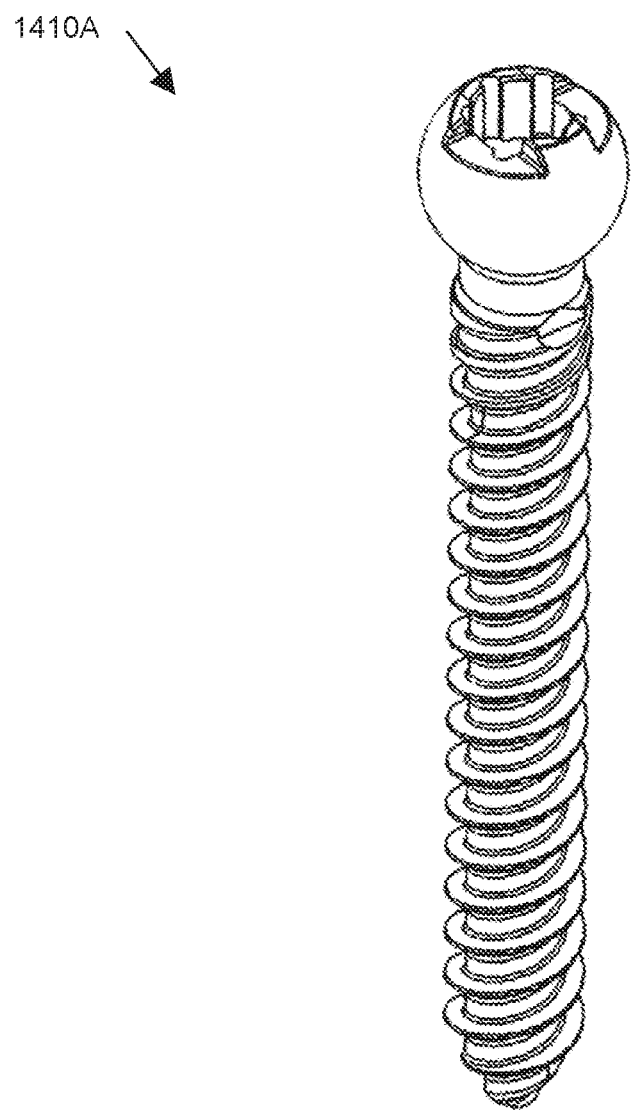
FIG. 17A shows a perspective view of an exemplary first bone anchor, per embodiments herein.
Figures 17B, 17C:
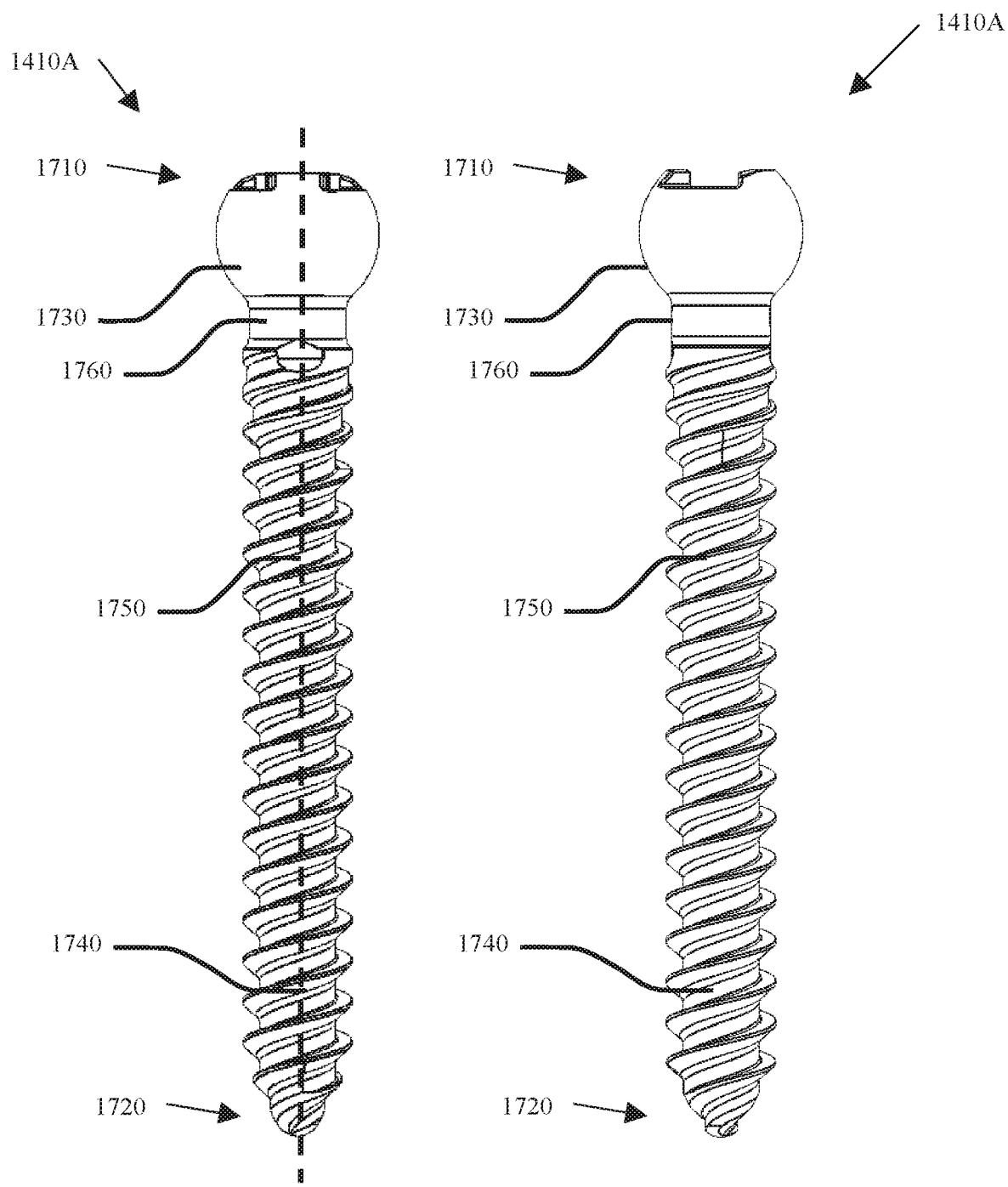
FIG. 17B shows a first side view of an exemplary first bone anchor, per embodiments herein.
FIG. 17C shows a second side view of an exemplary first bone anchor, per embodiments herein.
Figure 17D:
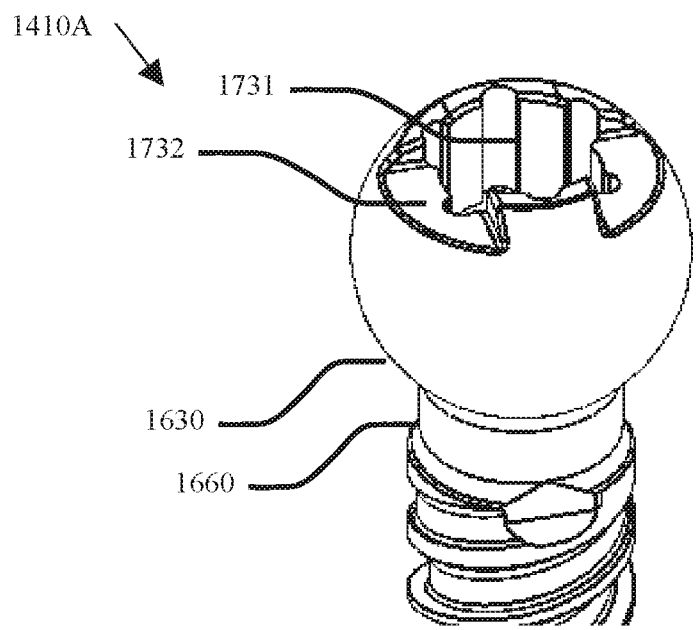
FIG. 17D shows a detailed top perspective view of an exemplary first bone anchor, per embodiments herein.
Figure 17E:
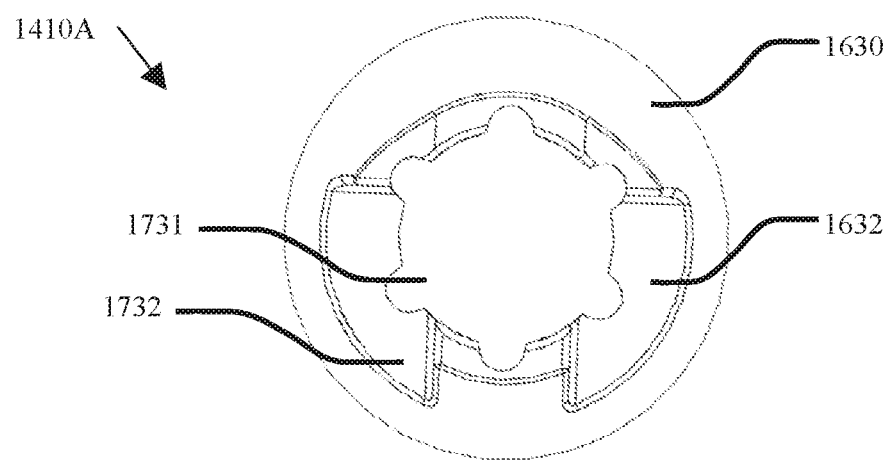
FIG. 17E shows a top view of an exemplary first bone anchor, per embodiments herein.
Figure 17F:
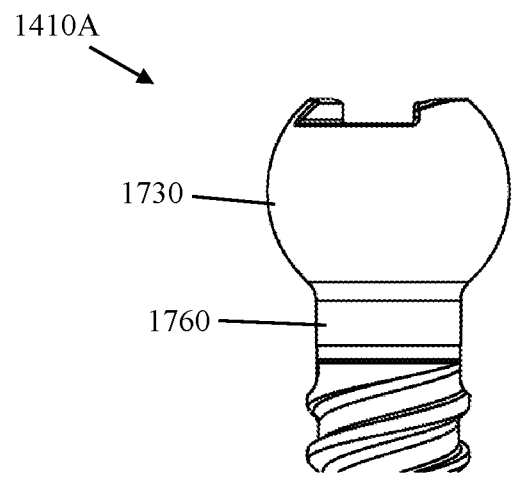
FIG. 17F shows a first detailed side view of an exemplary first bone anchor, per embodiments herein.
Figure 17G:
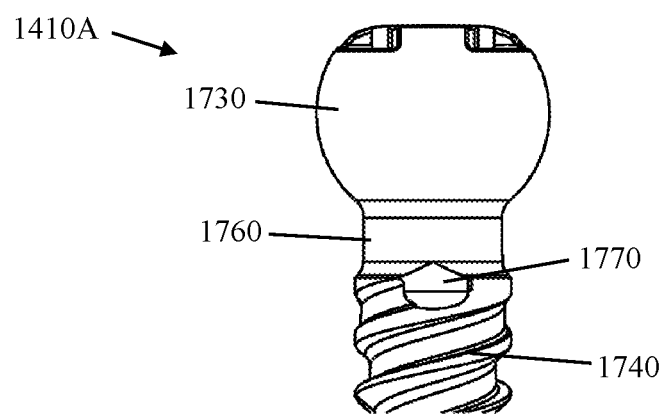
FIG. 17G shows a second detailed side view of an exemplary first bone anchor, per embodiments herein.
Figure 17H:
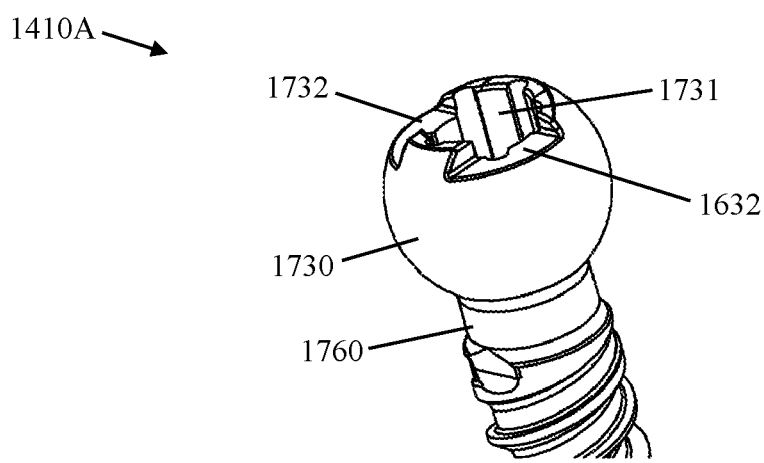
FIG. 17H shows a detailed perspective view of an exemplary first bone anchor, per embodiments herein.
Figure 17I:
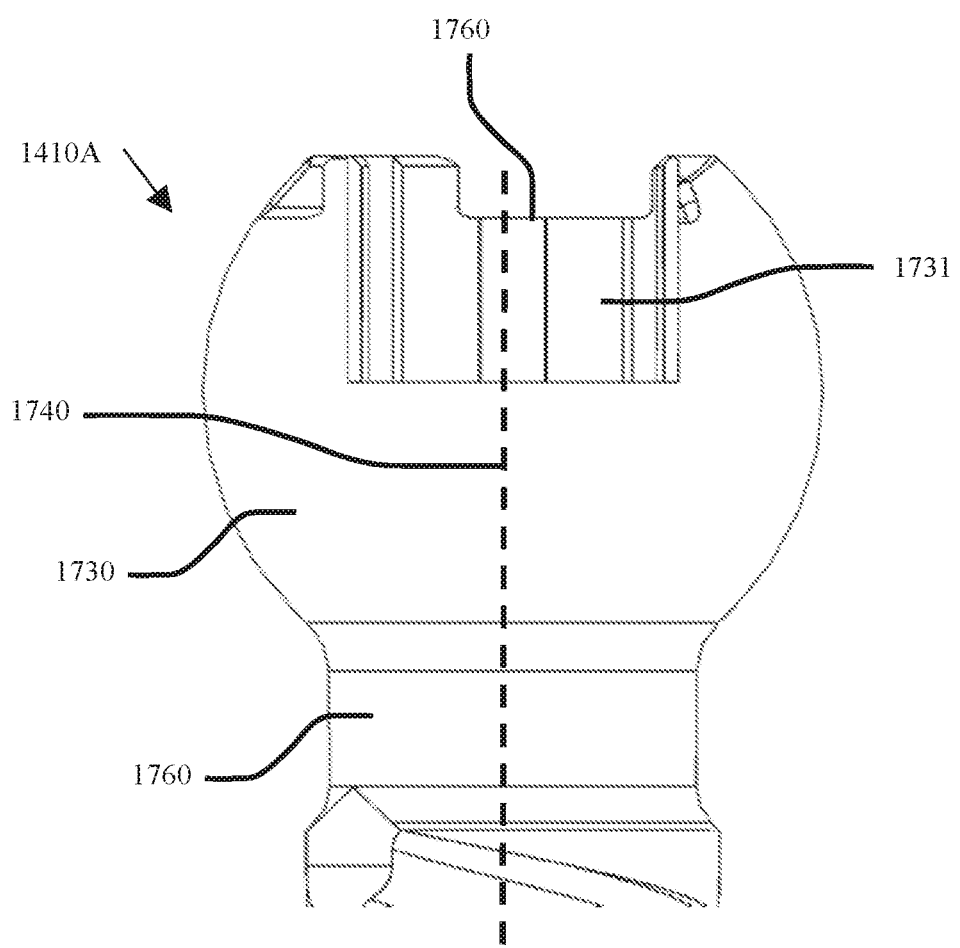
FIG. 17I shows a detailed cross sectional side view of an exemplary first bone anchor, per embodiments herein.

As seen in FIG. 17G, the bone anchor 1410 may further comprise a relief 1770. The bone anchor 1410 may comprise two or more reliefs 1770. The two or more reliefs 1770 may be on opposing sides of the bone anchor 1410. The relief 1770 may be within the neck 1760, the bone engagement 1740, or both. The relief 1770 may increase the span at which the bone anchor 1410 can rotate with respect to the receiver. The neck 1760 may be configured to fit within the socket cavity slot when the receiver axis and the longitudinal axis 1750 are generally coplanar and wherein the relief 1770 is generally parallel to the socket cavity slot.

An exemplary second bone anchor 1410B is seen in FIGS. 18A-G. The bone anchor 1410B may have a first end 1810, a second end 1820, a longitudinal axis 1850, and a neck 1860. The longitudinal axis 1850 may be defined as spanning from the first end 1810 to the second end 1820. The neck 1860 may be positioned between the first end 1810 and the second end 1820. The neck 1860 may be configured to fit within the socket cavity slot 1540. The neck 1860 may be configured to fit within the socket cavity slot 1540 when the receiver axis 1550 and the longitudinal axis 1850 are generally coplanar. The neck 1860 may have a diameter of less than a diameter of the head 1830.

The first end 1810 may comprise a head 1830. The head 1830 may comprise a spherically shaped head 1830. An outer surface of the head 1830 may comprise a drive feature 1831 and at least one head recess 1832. In some embodiments the at least one head recess 1832 comprises 2 head recesses 1832, 4 head recess 1832, or more. In some embodiments, the head 1830 comprises 2 distal head recesses 1832 and 2 proximal head recesses 1832. In some embodiments, the 2 distal head recesses 1832 and the 2 proximal head recesses 1832 are generally aligned about the head 1830. In some embodiments, the head 1830 comprises 2 distal recesses 1832 and 2 proximal recesses 1832 form a keyed contour of the bone anchor 1410B which interact with the interference areas 1595 and the keyed contour of the cavity aperture they define of the receiver 1420B. In some embodiments, the interaction facilitates a reversible engagement between the head 1830 of the bone anchor 1410B and the socket cavity of the receiver 1420B. In some embodiments, the interaction comprises an interaction in one or more planes. In some embodiments, the interaction comprises an interaction in two or more planes. In some embodiments, the interaction comprises an interaction in as many as three, four, or more planes. In an embodiment, a narrow range of angular orientations between the longitudinal axis of the second bone anchor 1410A and the receiver axis of the second receiver 1420A enables the head to enter or exit the socket cavity by translation only. In an embodiment, no angular orientation between the longitudinal axis of the second bone anchor 1410B and the receiver axis of the second receiver 1420B enables the head to enter or exit the socket cavity by translation only. The keyed contour of the bone anchor 1410B in at least one plane may then be configured to cooperate with the keyed contour of the cavity aperture to allow the head 1830 to reversibly enter the cavity by means of rotating, translating or rotating and translating of the keyed contour of the head relative 1830 to the keyed contour of the cavity aperture.

In some embodiments, the head recess 1832 comprises a channel. In some embodiments, the channel is generally perpendicular to the longitudinal axis 1850. At least a portion of the second end 1820 may comprise a bone engagement 1840. At least a portion of the second end 1820 may comprise a feature to affix to a separate component having the bone engagement 1840.

Figure 18A:
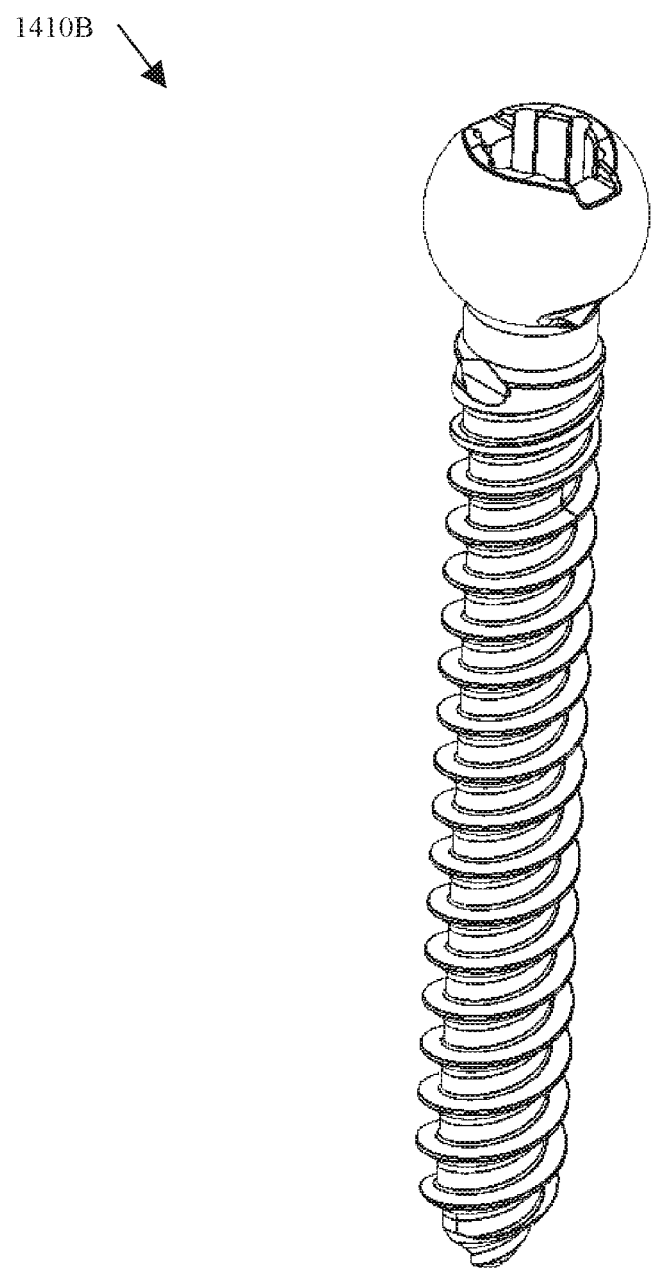
FIG. 18A shows a perspective view of an exemplary second bone anchor, per embodiments herein.
Figures 18B, 18C:
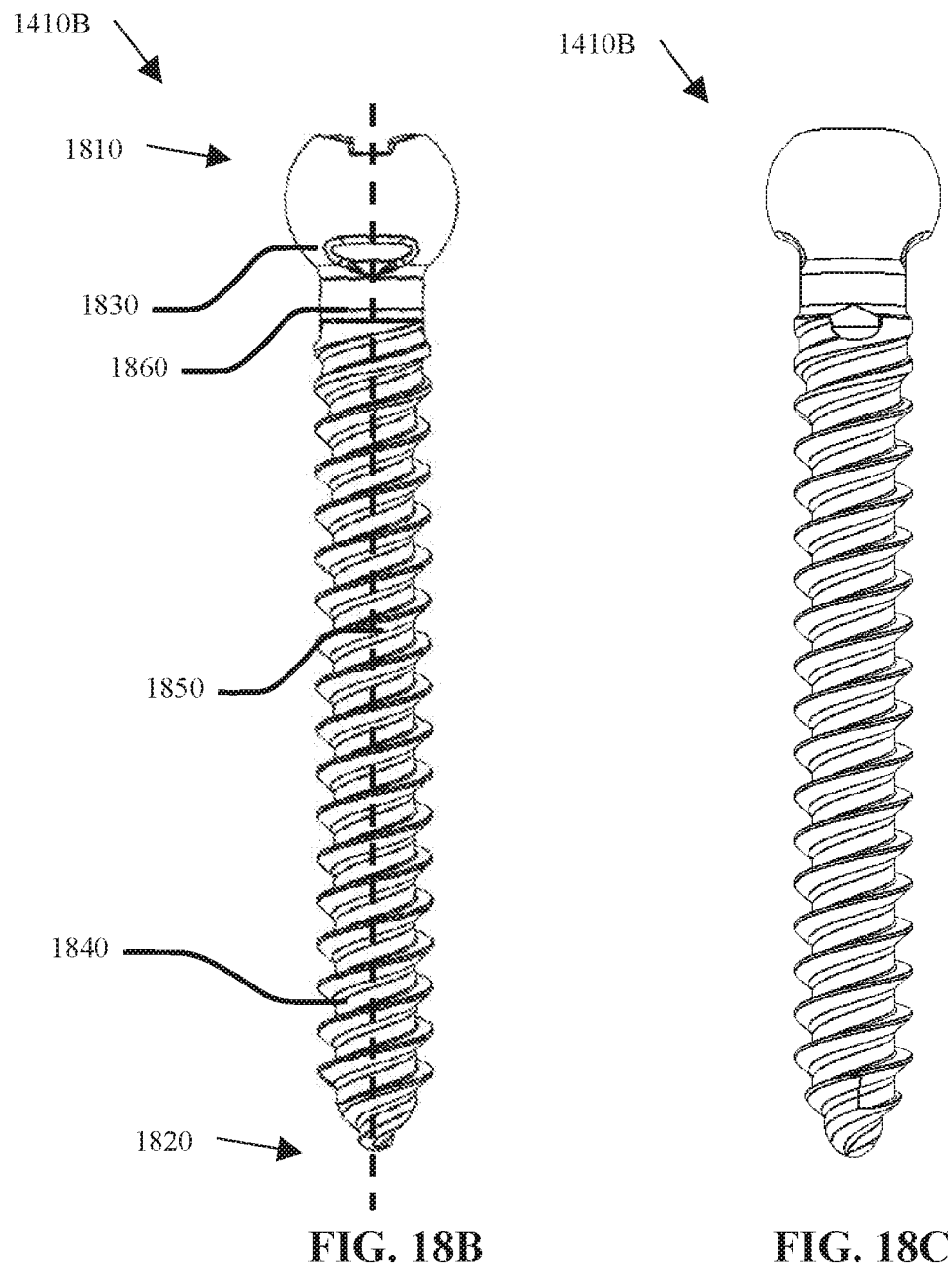
FIG. 18B shows a first side view of an exemplary second bone anchor, per embodiments herein.
FIG. 18C shows a second side view of an exemplary second bone anchor, per embodiments herein.
Figure 18D:
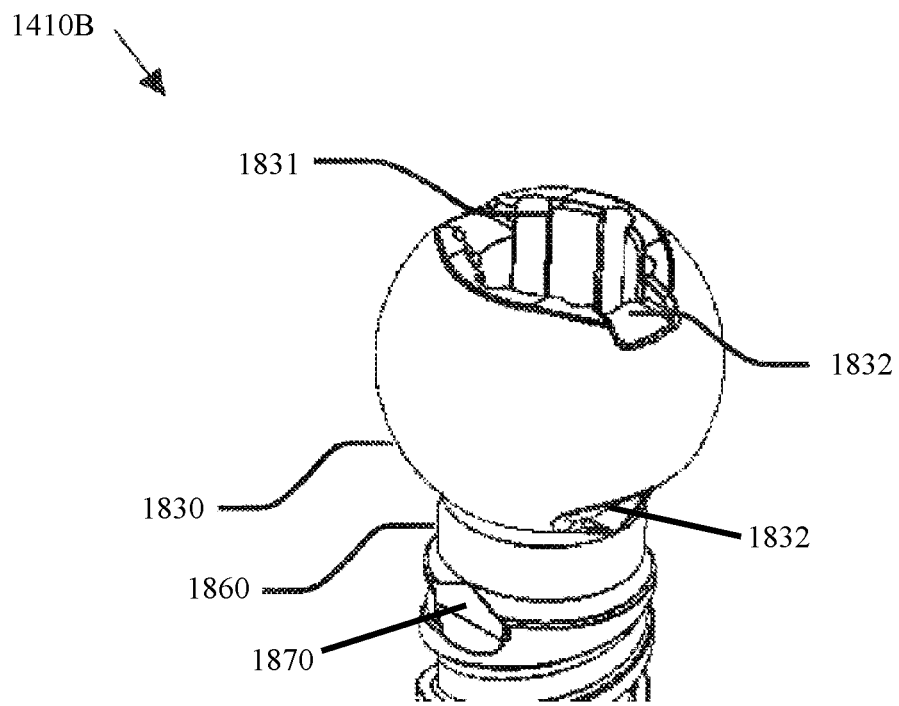
FIG. 18D shows a detailed top perspective view of an exemplary second bone anchor, per embodiments herein.
Figure 18E:
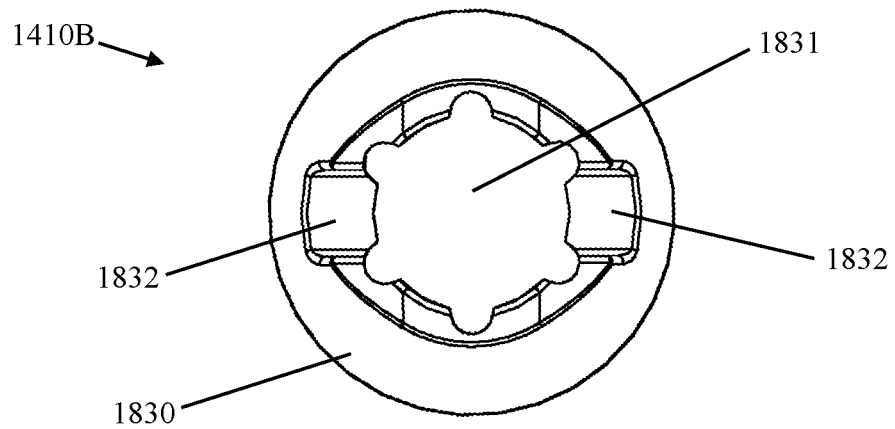
FIG. 18E shows a top view of an exemplary second bone anchor, per embodiments herein.
Figure 18F:
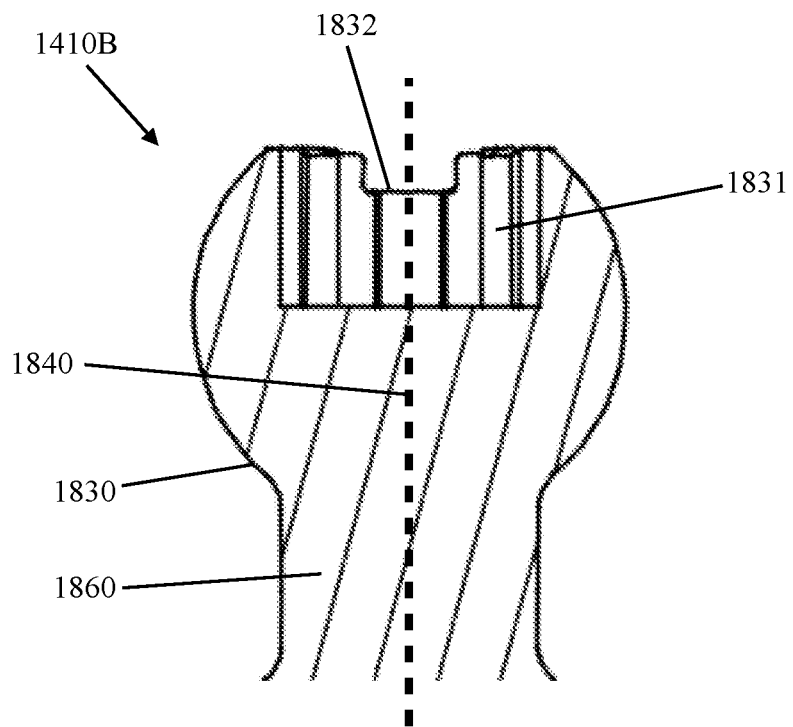
FIG. 18F shows a first detailed side cross sectional view of an exemplary second bone anchor, per embodiments herein.
Figure 18G:
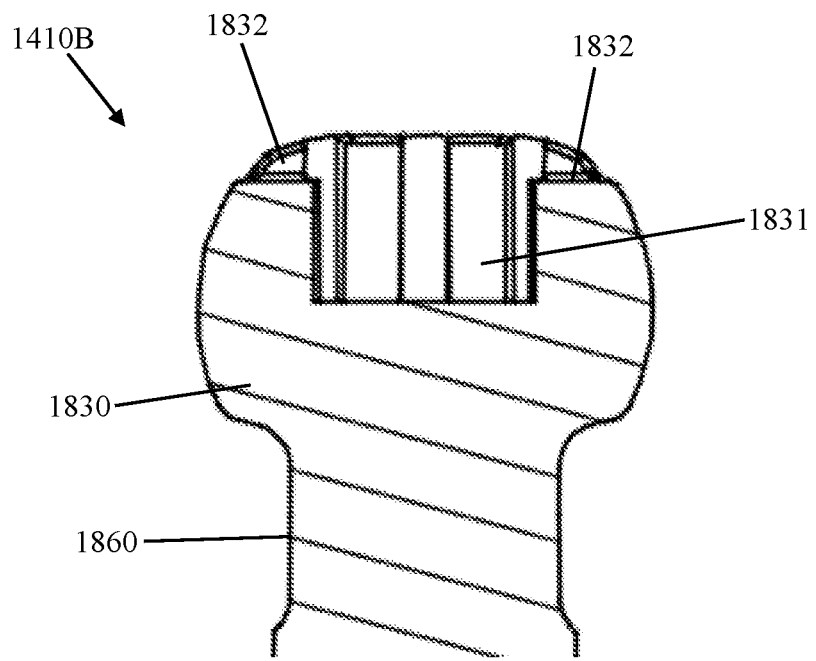
FIG. 18G shows a second detailed side cross sectional view of an exemplary second bone anchor, per embodiments herein.

As seen in FIG. 18D, the bone anchor 1410 may further comprise a relief 1870. The bone anchor 1410 may comprise two or more reliefs 1870. The two or more reliefs 1870 may be on opposing sides of the bone anchor 1410. The relief 1870 may be within the neck 1860, the bone engagement 1840, or both. The relief 1870 may increase the span at which the bone anchor 1410 can rotate with respect to the receiver. The neck 1860 may be configured to fit within the socket cavity slot when the receiver axis and the longitudinal axis 1850 are generally coplanar and wherein the relief 1870 is generally parallel to the socket cavity slot. In some embodiments, the second bone anchor 1410B may be configured for use with the second receiver 1420B.

The socket aperture 1531 may be configured to releasably receive the head 1730, 1830. The socket aperture 1531 may comprise a straight segment, a curved segment, or both. The socket aperture 1531 may comprise two or more straight segments, two or more curved segments, or both. The curved segments may have the same diameter. The curved segments may have different diameters. The socket aperture 1531 may comprise a series of segments comprising at least one straight segment and at least one curved segment. The socket aperture 1531 may comprise 1, 2, 3, 4, 5, 6, 7, 8, 9, 10, or more straight segments. The socket aperture 1531 may further comprise 1, 2, 3, 4, 5, 6, 7, 8, 9, 10, or more curved segments. The socket cavity slot 1540 may extend from the socket cavity 1530. The socket cavity slot 1540 may be configured to receive the neck 1860. The socket aperture 1531 and the socket cavity slot 1540 may be configured to releasably engage with the bone anchor 1410. The socket aperture 1531 and the socket cavity slot 1540 may be configured to releasably engage with the bone anchor 1410 upon rotation of the bone anchor 1410 with respect to the socket cavity 1530, translation of the bone anchor 1410 with respect to the socket cavity 1530, or both. In some embodiments, the socket cavity 1530 releasably constrains the head to rotate about the longitudinal axis 1750, 1850, a rotational axis perpendicular to the longitudinal axis 1750, 1850, or both. In some embodiments, the socket cavity 1530 releasably constrains the head to rotate 360 degrees about the longitudinal axis 1750, 1850. In some embodiments, the socket cavity 1530 releasably constrains the head to rotate within a range of about 5 degrees to about 90 degrees from the rotational axis.

Figure 22A:
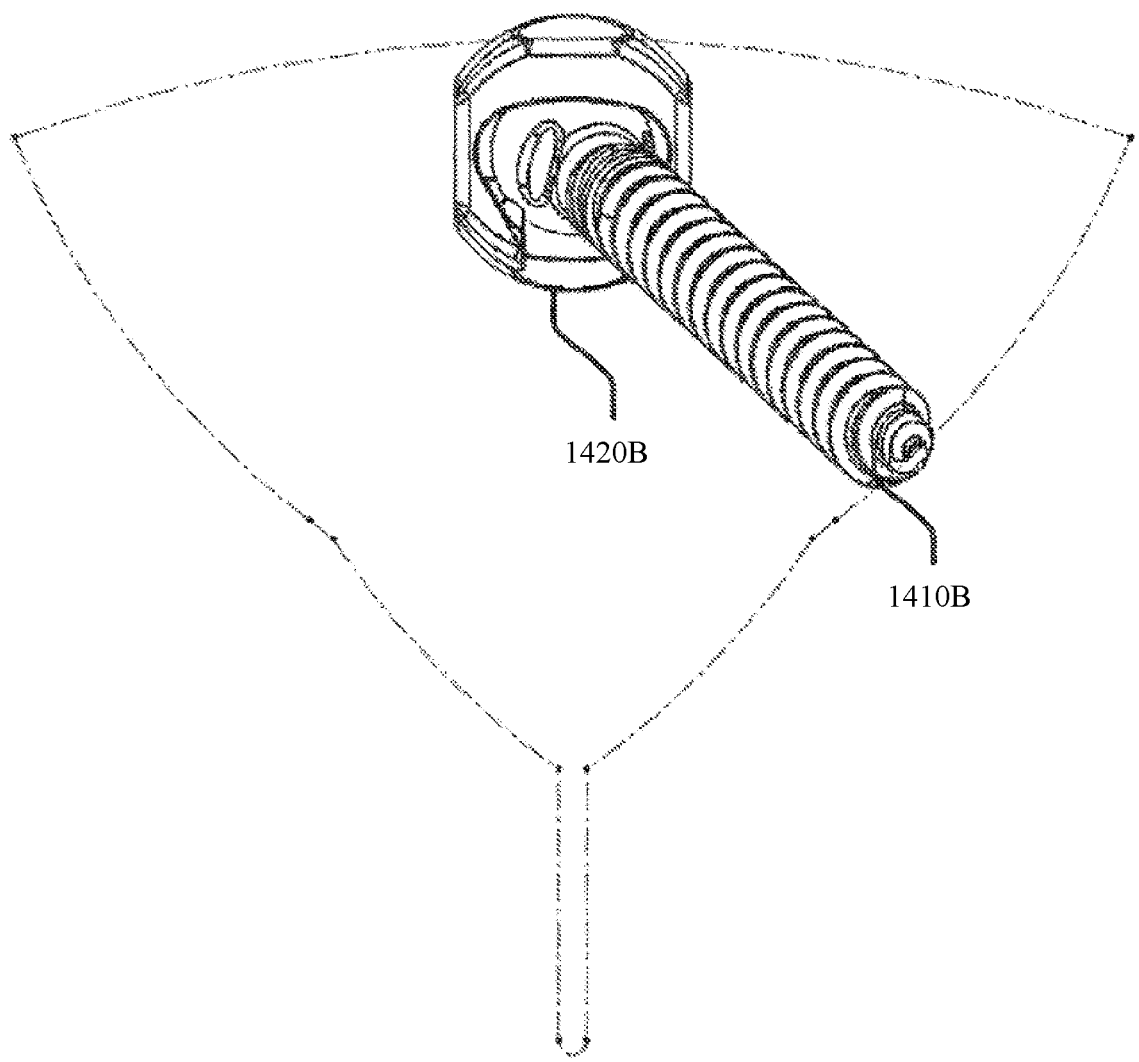
FIG. 22A shows the trace of an exemplary screw angulation path for a spinal anchor assembly comprising the first receiver described herein.
Figure 22B:
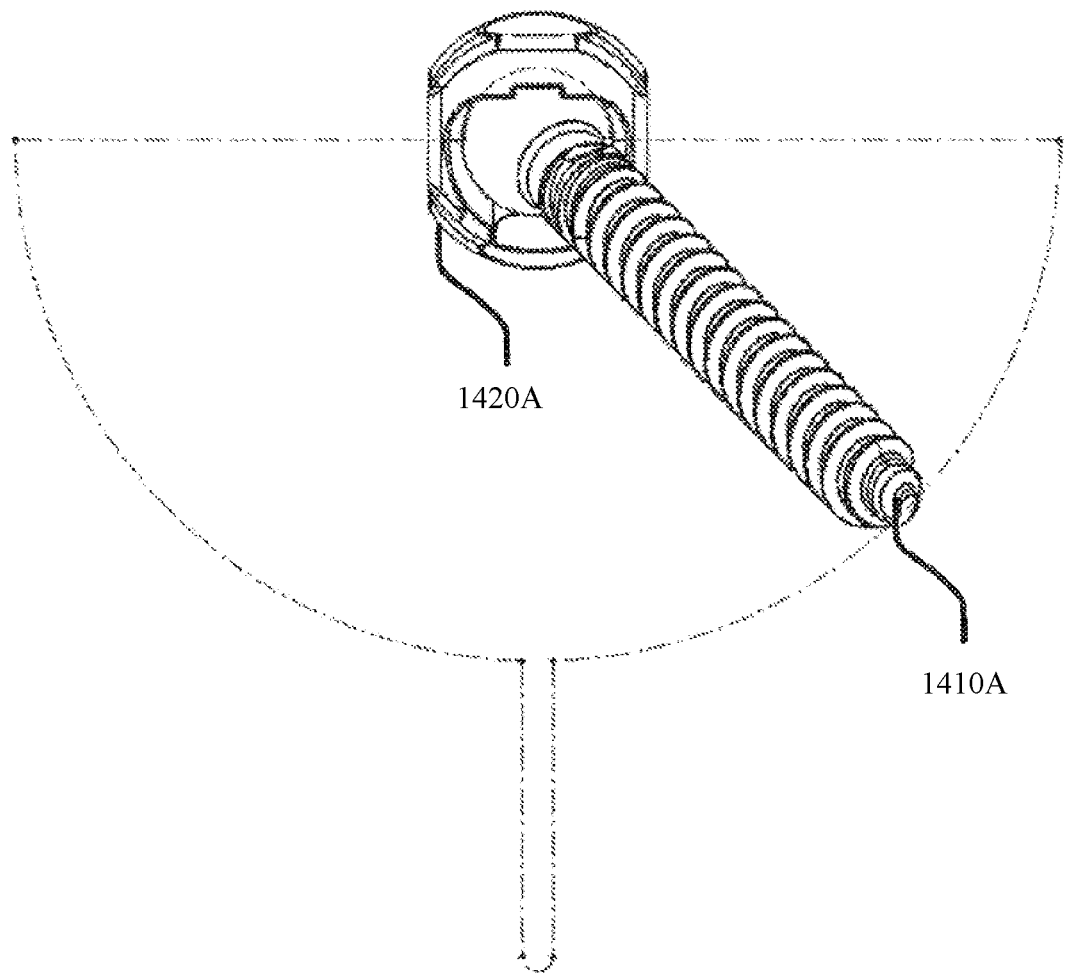
FIG. 22B shows the trace of an exemplary screw angulation path for a spinal anchor assembly comprising the second receiver described herein.
Figure 23A:
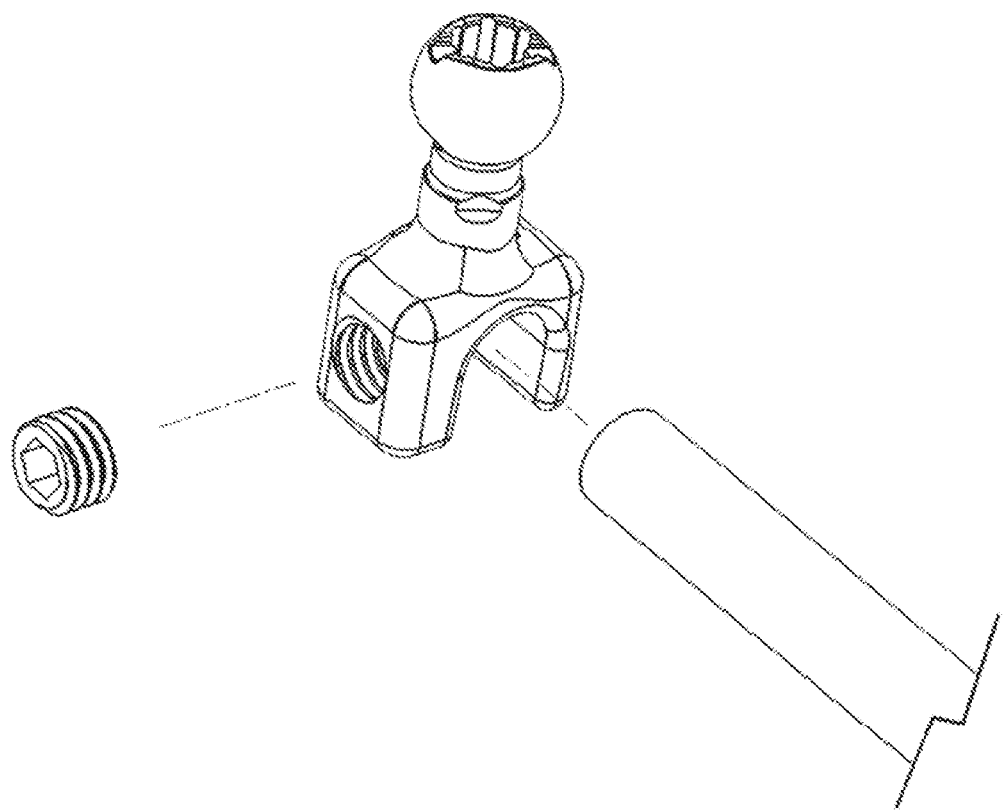
FIG. 23A shows a perspective view of an exemplary first spinal anchor assembly without a bone fastener.
Figure 23B:
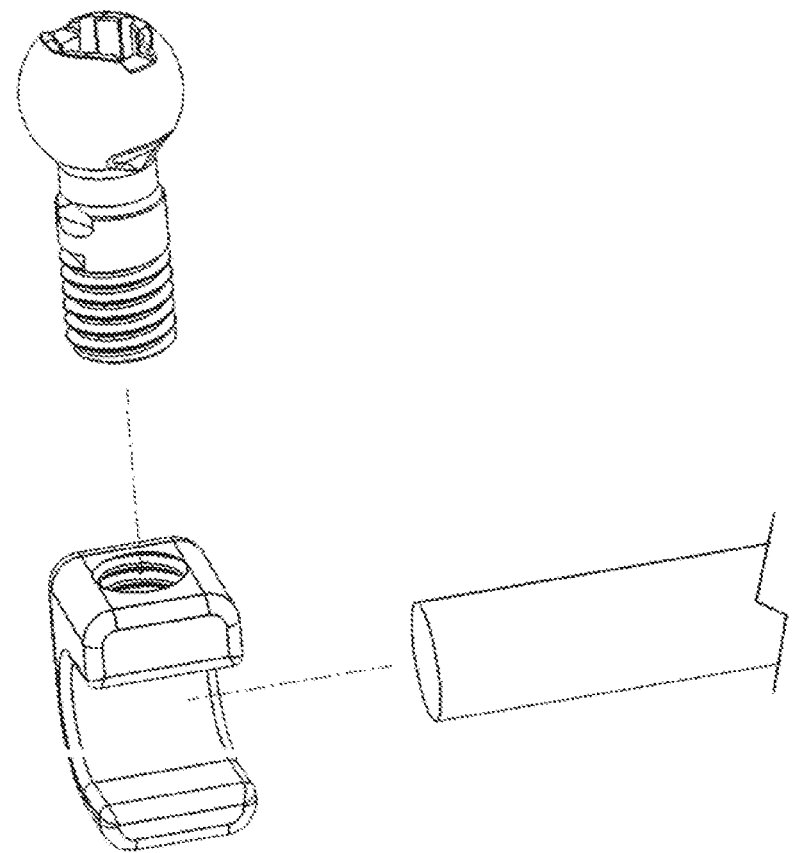
FIG. 23B shows a perspective view of an exemplary second spinal anchor assembly without a bone fastener.

FIG. 22A shows the trace of an exemplary screw angulation path for a spinal anchor assembly comprising the second receiver 1420B described herein. FIG. 22B shows the trace of an exemplary screw angulation path for a spinal anchor assembly comprising the first receiver 1420A described herein.

In some embodiments the socket aperture 1531 comprises the first opening. In some embodiments the socket cavity 1530 comprises the volume. In some embodiments the socket cavity slot 1540 comprises the second opening. In some embodiments, the neck 1760, 1860 comprises the keyed portion. In some embodiments, the neck 1760, 1860 is located on the anchor adjacent to the neck.

Method of Engaging a Screw with a Receiver

Also provided herein is a method of engaging a screw with a receiver 1420 comprising: providing a polyaxial anchor assembly 1400, advancing the receiver 1420 toward the screw, inserting the head 1630 into the socket cavity 1530, and releasably engaging the head with the socket cavity 1530

The polyaxial anchor assembly 1400 may comprise a bone anchor 1410 and a receiver 1420. The bone anchor 1410 may comprise a first end 1610 and a second end 1620. The first end 1610 may comprise a head 1630. An outer surface of the head 1630 may comprise at least one head recess head recess 1632. At least a portion of the second end 1620 may comprises a bone engagement and a neck. The neck may be between the first end 1610 and the second end 1620.

The receiver 1420 may have first receiver end and a second receiver end. The first receiver end may comprise a socket cavity 1530. The socket cavity 1530 may comprise a socket aperture 1540 and a socket cavity 1530. The socket aperture 1540 may be configured to releasably receive the head 1630. The socket cavity slot may extend from the socket cavity 1530. The socket cavity slot may be configured to receive the neck.

The head 1630 may releasably engage with the socket cavity 1530 by rotating the bone anchor 1410 with respect to the socket cavity, translating the bone anchor 1410 with respect to the socket cavity 1530, or both.

In some embodiments, rotating the bone anchor 1410 with respect to the socket cavity 1530 comprises rotating the bone anchor 1410 with respect to the socket cavity 1530 in a first rotational direction, rotating the bone anchor 1410 with respect to the socket cavity 1530 in a second rotational direction different than the first rotational direction, translating the bone anchor 1410 with respect to the socket cavity 1530 in a first translational direction, translating the bone anchor 1410 with respect to the socket cavity 1530 in a second translational direction different than the first translational direction, or any combination thereof. In some embodiments, rotating the bone anchor 1410 with respect to the socket cavity 1530 comprises rotating the bone anchor 1410 with respect to the socket cavity 1530 in one or more rotational direction, translating the bone anchor 1410 with respect to the socket cavity 1530 in a one or more translational directions, or any combination thereof.

In some embodiments, the method further comprises inserting the neck into the socket cavity 1530. In some embodiments, the method further comprises employing a driver feature surface of the head 1630 to attach the bone anchor 1410 to a target work surface. In some embodiments, the method further comprises providing a rod. In some embodiments, the method further comprises inserting the rod into a rod slot 1560 within the receiver 1420. In some embodiments, the method further comprises providing a set screw.

Figure 19A:
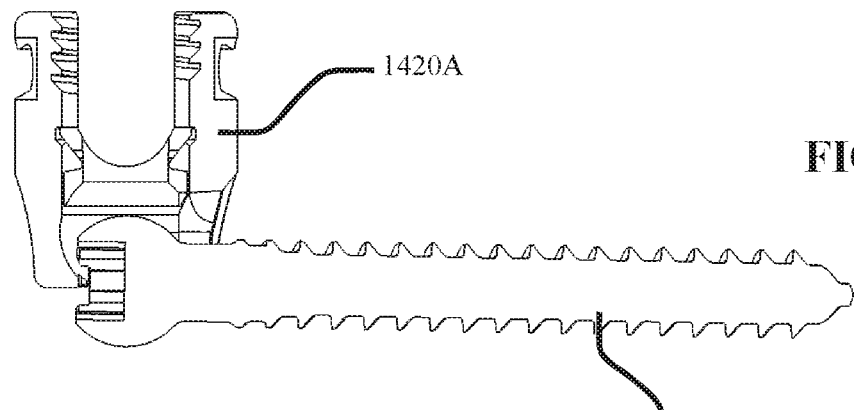
FIG. 19A shows a cross sectioned view of a first step of coupling an exemplary first receiver and an exemplary first bone anchor, per embodiments herein.
Figure 19B:
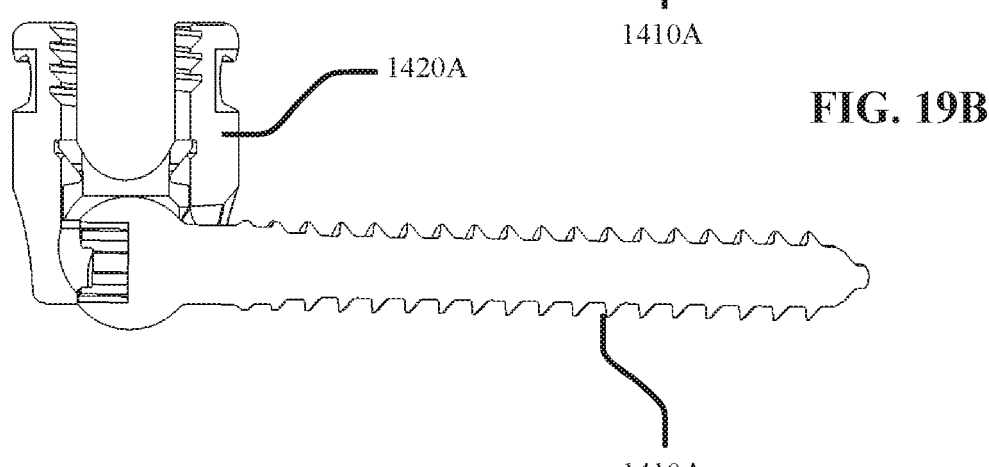
FIG. 19B shows a cross sectioned view of a second step of coupling an exemplary first receiver and an exemplary first bone anchor, per embodiments herein.
Figure 19C:
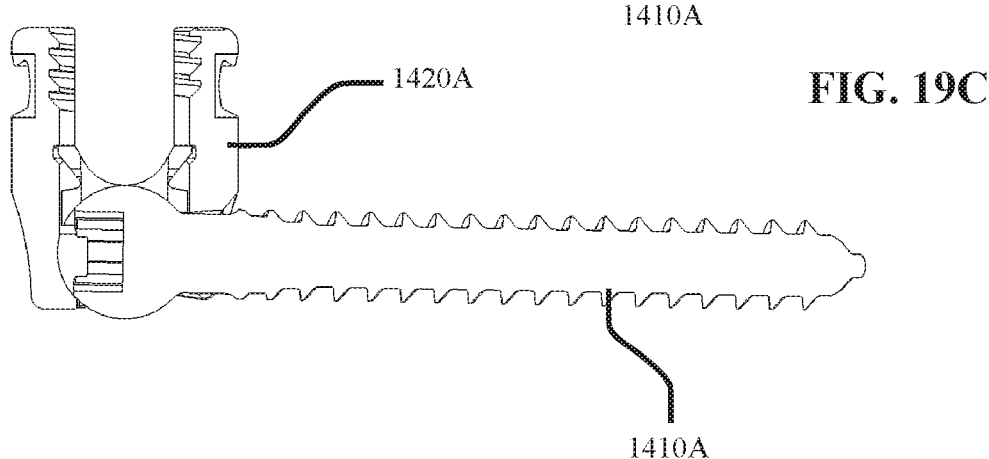
FIG. 19C shows a cross sectioned view of a third step of coupling an exemplary first receiver and an exemplary first bone anchor, per embodiments herein.
Figure 19D:
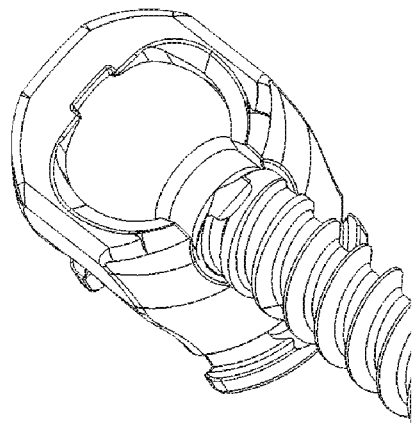
FIG. 19D shows a perspective view of a third step of coupling an exemplary first receiver and an exemplary first bone anchor, per embodiments herein.
Figure 19E:
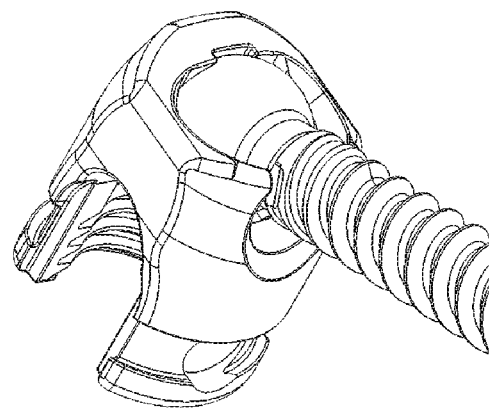
FIG. 19E shows a perspective view of a fourth step of coupling an exemplary first receiver and an exemplary first bone anchor, per embodiments herein.
Figure 19F:
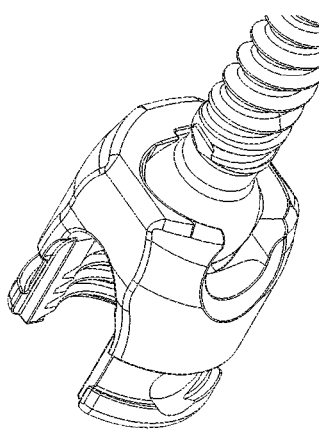
FIG. 19F shows a perspective view of a fifth step of coupling an exemplary first receiver and an exemplary first bone anchor, per embodiments herein.

An exemplary method for coupling an exemplary first receiver 1420A and an exemplary first bone anchor 1410A is shown in FIGS. 19A-F. FIG. 19A shows a cross sectioned view of a first step of coupling an exemplary first receiver 1420A and an exemplary first bone anchor 1410A. FIG. 19B shows a cross sectioned view of a second step of coupling an exemplary first receiver 1420A and an exemplary first bone anchor 1410A. The second step may comprise translating the bone anchor 1410A. FIG. 19C shows a cross sectioned view of a third step of coupling an exemplary first receiver 1420A and an exemplary first bone anchor 1410A. The second step may comprise additional translation of the bone anchor 1410A FIG. 19D shows a perspective view of a third step of coupling an exemplary first receiver 1420A and an exemplary first bone anchor 1410A. FIG. 19E shows a perspective view of a fourth step of coupling an exemplary first receiver 1420A and an exemplary first bone anchor 1410A. The fourth step may comprise rotating the bone anchor 1410A about the longitudinal axis such to align the reliefs with the margins on the receiver 1420A to allow the bone anchor 1410A to rotate upwards. FIG. 19F shows a perspective view of a fifth step of coupling an exemplary first receiver 1420A and an exemplary first bone anchor 1410A.

An exemplary method for coupling an exemplary second receiver 1420B and an exemplary second bone anchor 1410B is shown in FIGS. 20A-I.

Figure 20A:
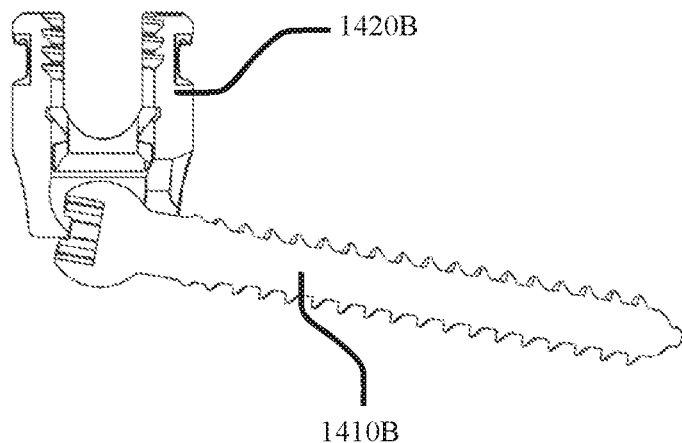
FIG. 20A shows a cross sectioned view of a first step of coupling an exemplary second receiver and an exemplary second bone anchor, per embodiments herein.
Figure 20B:
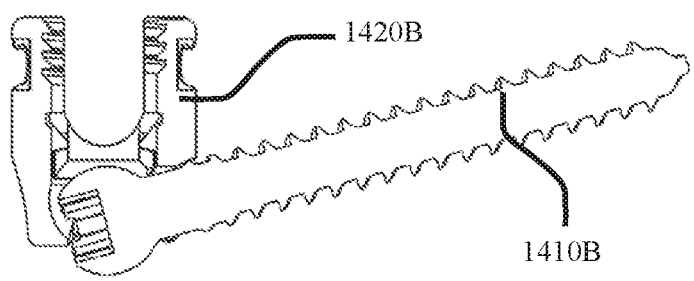
FIG. 20B shows a cross sectioned view of a second step of coupling an exemplary second receiver and an exemplary second bone anchor, per embodiments herein.
Figure 20C:
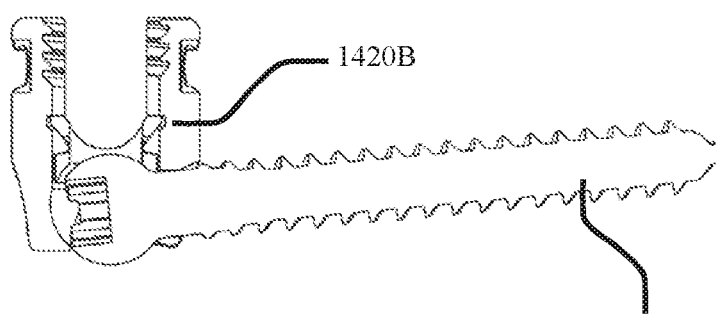
FIG. 20C shows a cross sectioned view of a third step of coupling an exemplary second receiver and an exemplary second bone anchor, per embodiments herein.
Figure 20D:
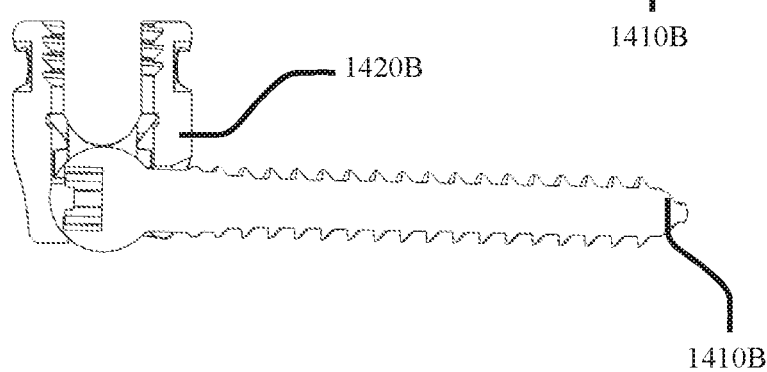
FIG. 20D shows a cross sectioned view of a fourth step of coupling an exemplary second receiver and an exemplary second bone anchor, per embodiments herein.
Figure 20E:
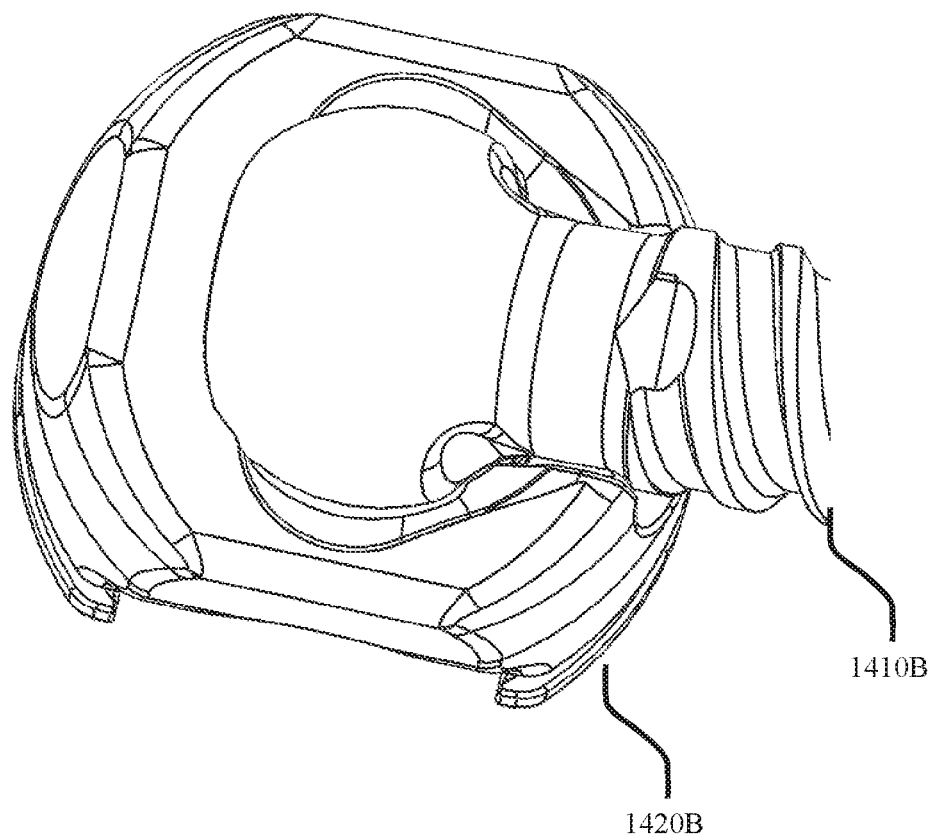
FIG. 20E shows a perspective view of a first step of coupling an exemplary second receiver and an exemplary second bone anchor, per embodiments herein.
Figure 20F:
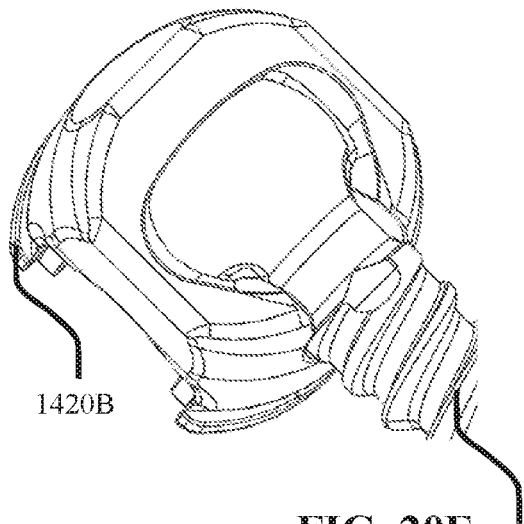
FIG. 20F shows a perspective view of a fourth step of coupling an exemplary second receiver and an exemplary second bone anchor, per embodiments herein.
Figure 20G:
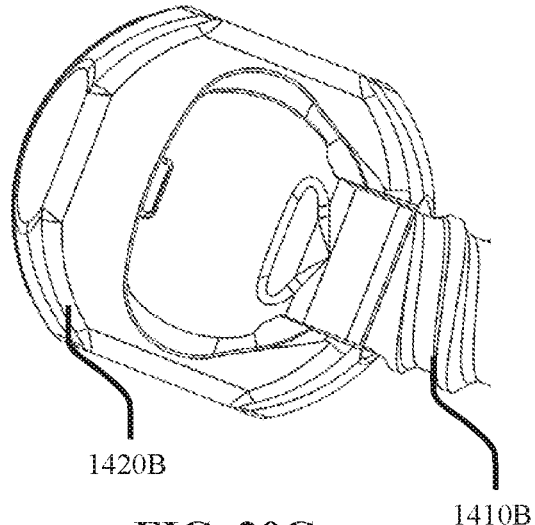
FIG. 20G shows a perspective view of a fifth step of coupling an exemplary second receiver and an exemplary second bone anchor, per embodiments herein.
Figure 20H:
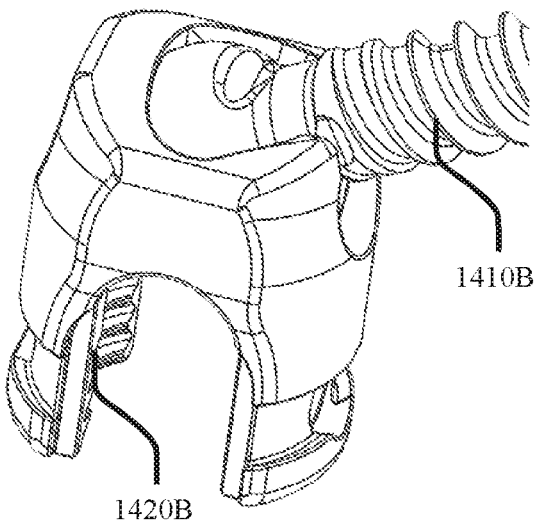
FIG. 20H shows a perspective view of a sixth step of coupling an exemplary second receiver and an exemplary second bone anchor, per embodiments herein.
Figure 20I:
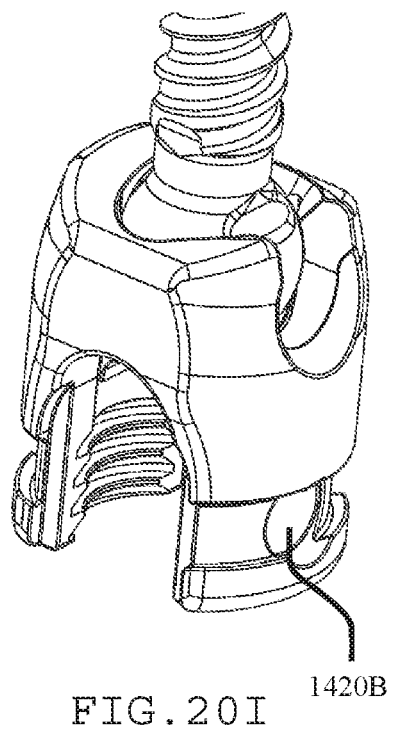
FIG. 20I shows a perspective view of a seventh step of coupling an exemplary second receiver and an exemplary second bone anchor, per embodiments herein.

FIG. 20A shows a cross sectioned view of a first step of coupling an exemplary second receiver and an exemplary second bone anchor. FIG. 20E shows a perspective view of a first step of coupling an exemplary second receiver and an exemplary second bone anchor. In this step a designed clearance is employed to allow the bone anchor to rotate past 90 degrees. FIG. 20B shows a cross sectioned view of a second step of coupling an exemplary second receiver and an exemplary second bone anchor. The second step may comprise rotating the bone anchor about the head. FIG. 20C shows a cross sectioned view of a third step of coupling an exemplary second receiver and an exemplary second bone anchor. The third step may comprise rotating the bone anchor about the head and translating the bone anchor. FIG. 20F shows a perspective view of a fourth step of coupling an exemplary second receiver and an exemplary second bone anchor. FIG. 20D shows a cross sectioned view of a fourth step of coupling an exemplary second receiver and an exemplary second bone anchor. The fourth step may comprise rotating the bone anchor about the head and translating the bone anchor, whereas the interference between the bone anchor and the socket cavity slot substantially prevent rotation of the bone anchor about an axis perpendicular to the longitudinal axis to the extent that the neck is inhibited from completely exiting the cavity slot. The interference between the bone anchor and the socket cavity slot may further prevent the longitudinal axis from becoming collinear with the receiver axis. FIG. 20G shows a perspective view of a fifth step of coupling an exemplary second receiver and an exemplary second bone anchor. The fifth step may comprise rotating the bone anchor about the longitudinal axis. The fifth step may comprise rotating the bone anchor about the longitudinal axis by about 90 degrees or by less than 45 degrees or by 180 degrees. The fifth step may comprise rotating the bone anchor about the longitudinal axis to bypass the interference between the bone anchor and the socket cavity slot by substantially aligning relief or reliefs with the cavity slot and allow the neck to fully exit the cavity slot and allow the bone anchor to rotate about 90 degrees to be generally coaxial with the receiver. In this state the driving feature may be visible and employable. FIG. 20H shows a perspective view of a sixth step of coupling an exemplary second receiver and an exemplary second bone anchor. In this step, the bone anchor clears the slot as the relief are aligned and bypassed. FIG. 20I shows a perspective view of a seventh step of coupling an exemplary second receiver and an exemplary second bone anchor.

An exemplary method for engaging the exemplary first receiver 1420A and the bone anchor 1410 is shown in FIGS. 19A-20I. An exemplary method for engaging the exemplary second receiver 1420B and the bone anchor 1410 is shown in FIGS. 20A-B. In some embodiments, the method comprises translating the bone anchor 1410 towards the receiver 1420 in a first translational direction, per FIGS. 19A-C, towards and into the receiver 1420, such that the socket cavity of the receiver 1420 surrounds the head.

Another exemplary method for engaging the receiver 1420 and the bone anchor 1410 is shown in FIGS. 20A-D. In some embodiments, the method comprises translating the bone anchor 1410 towards the receiver 1420 in a first translational direction towards and into the receiver 1420, per FIG. 20A, such that the head recess surrounds at least a portion of the socket aperture and a socket cavity rotating the bone anchor 1410 into the socket cavity, per FIG. 20B, in a first rotational direction such that the neck of the bone anchor 1410 into the cavity slot of the receiver 1420, and rotating the bone anchor 1410 away from the receiver 1420 in a rotational direction opposite the first rotational direction, and optionally also translating the bone anchor toward receiver, per FIGS. 20C and 20D.

Figure 21:
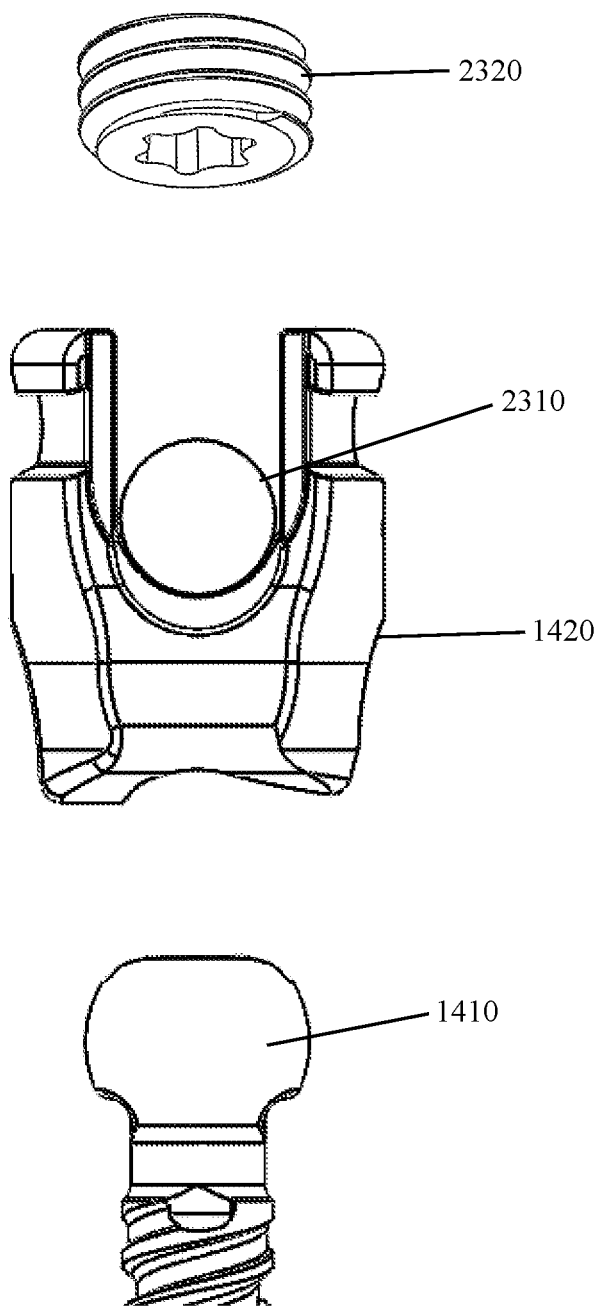
FIG. 21 shows a side view of an exemplary expanded polyaxial spinal anchor assembly described herein.

In some embodiments, per FIG. 21, the method further comprises providing a set screw 2120 inserting the set screw 2120 over the rod 2110 and into a threaded bore within the receiver 1420. In some embodiments, the method further comprises tightening the set screw 2120 within the threaded bore to compress a compression element between the rod 2110 and the head of the bone anchor 1410.

Terms and Definitions

Unless otherwise defined, all technical terms used herein have the same meaning as commonly understood by one of ordinary skill in the art to which this disclosure belongs.

As used herein, the singular forms "a," "an," and "the" include plural references unless the context clearly dictates otherwise. Any reference to "or" herein is intended to encompass "and/or" unless otherwise stated.

As used herein, the term "about" refers to an amount that is near the stated amount by 10%, 5%, or 1%, including increments therein.

As used herein, the term "generally perpendicular" refers to within 1 degree, within 2 degrees, within 3 degrees, within 4 degrees, within 5 degrees, or more of perpendicular.

As used herein, the term "generally parallel" refers to within 1 degree, within 2 degrees, within 3 degrees, within 4 degrees, within 5 degrees, or more of parallel.

As used herein, the term "percent head coverage" a central angle of the sector occupied by the keyed portion of the terminal opening and expressed as a percentage of 360 degrees.

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure.

What is claimed is:

1. A polyaxial anchor assembly comprising:
  a bone anchor including a first end comprising a head having a spherical outer surface and a recess formed within the head, a second end, a longitudinal axis extending through the first and second ends, and a neck positioned along the longitudinal axis between the head and the second end;
  a receiver having a first receiver end, a second receiver end, and a receiver axis extending through the first receiver end and the second receiver end, the first receiver end comprising a socket cavity configured to receive at least a portion of the head, a socket aperture, a socket cavity slot extending from the socket cavity and configured to receive at least a portion of the neck, and an interference element extending over a portion of the socket aperture opposite the socket cavity slot;
  wherein the interference element is configured to prevent translation-only insertion of the head into the socket cavity; and
  wherein the head is configured to be inserted into the socket cavity upon engagement of the recess with the interference element, rotation of the bone anchor in a first rotation direction such that a first portion of the spherical outer surface enters the socket cavity, and subsequent rotation of the bone anchor in a second rotation direction different from the first rotation direction such that a second portion of the spherical outer surface of the head clears the interference element and enters the socket cavity.

2. The assembly of claim 1, wherein the recess comprises a channel.

3. The assembly of claim 2, wherein the channel is generally perpendicular to the longitudinal axis.

4. The assembly of claim 1, wherein the second end of the bone anchor comprises a bone engagement element.

5. The assembly of claim 1, further comprising a rod.

6. The assembly of claim 5, wherein the receiver further comprises a rod slot configured to accept the rod.

7. The assembly of claim 6, wherein the rod slot is generally perpendicular to the receiver axis.

8. The assembly of claim 5, wherein the receiver further comprises a compression element positioned between the first receiver end and the second receiver end, the compression element configured to transfer a force from the rod to the head.

9. The assembly of claim 1, wherein the head comprises a truncated sphere with a flat surface, and the recess is formed by at least one projection extending from the flat surface.

10. The assembly of claim 1, wherein the receiver further comprises a threaded bore configured to threadably receive a set screw.

11. The assembly of claim 10, wherein the threaded bore is generally parallel to the receiver axis.

12. The assembly of claim 1, wherein the socket cavity releasably constrains the head to rotate about the longitudinal axis, a rotational axis perpendicular to the longitudinal axis, or both.

13. The assembly of claim 12, wherein the socket cavity releasably constrains the head to rotate 360 degrees about the longitudinal axis.

14. The assembly of claim 12, wherein the socket cavity releasably constrains the head to rotate within a range of about 5 degrees to about 90 degrees from the rotational axis.

15. The assembly of claim 1, wherein the receiver further comprises one or more secondary interference elements extending into the cavity aperture.

16. The assembly of claim 1, wherein the bone anchor further comprises one or more reliefs positioned on at least one of the neck and second end.

17. The assembly of claim 16, wherein the socket cavity slot is configured to permit pivoting of the neck out of the socket cavity slot and towards coaxial alignment with the receiver axis only upon rotation of the bone anchor by a first number of degrees about the longitudinal axis when the head is fully inserted into the socket cavity.

18. A method of assembling a polyaxial anchor assembly, comprising:
  a. providing a bone anchor having a first end, a second end, a longitudinal axis extending through the first and second ends, and a neck positioned on the longitudinal axis between the first end and the second end, the first end comprising a spherical shaped head and a recess formed within the head;
  b. providing a receiver having a first receiver end, a second receiver end, and a receiver axis extending through the first and second receiver ends, the first receiver end comprising a socket cavity, a socket aperture, a socket cavity slot extending from the socket cavity in a transverse direction relative to the receiver axis, and an interference element extending over a portion of the socket aperture opposite the socket cavity slot;
  c. inserting a first portion of the head into the socket cavity while the bone anchor is oriented at a first angular orientation relative to the receiver axis such that the recess is engaged with the interference element and the neck is at least partially inserted within the socket cavity slot;
  d. advancing the first portion of the head further into the socket cavity by at least rotating the bone anchor to a second angular orientation relative to the receiver axis in a first rotation direction while the recess is engaged with the interference element, wherein the angle between the longitudinal axis and the receiver axis in the second angular orientation is greater than the angle between the longitudinal axis and the receiver axis in the first angular orientation;
  e. advancing a second portion of the head into the socket cavity by at least rotating the bone anchor in a second rotation direction different from the first rotation direction such that the second portion of the head clears the interference element and enters the socket cavity, fully capturing the head within the socket cavity; and
  f. rotating the bone anchor with respect to the socket cavity about the head in the second rotation direction such that the neck disengages from the socket cavity slot.

19. The method of claim 18, further comprising providing a rod and inserting the rod into a rod slot within the receiver.

20. The method of claim 19, further comprising providing a set screw and inserting the set screw over the rod and into a threaded bore within the receiver.

21. The method of claim 20, further comprising tightening the set screw within the threaded bore to force the head against the interference element.

22. The method of claim 18, wherein the bone anchor further comprises one or more reliefs positioned on at least one of the neck and the second end.

23. The method of claim 22, wherein the socket cavity slot is configured to permit pivoting of the neck out of the socket cavity slot and towards coaxial alignment with the receiver axis only upon rotation of the bone anchor by a first number of degrees about the longitudinal axis when the head is fully captured within the socket cavity.

24. A polyaxial spinal anchor assembly comprising:
  a. a bone anchor having:
    i. a first end and a second end, the first end comprising a head comprising a first keyed contour in at least one plane; and
    ii. a neck extending from the head toward the second end, the neck having a diameter less than a diameter of the head; and
  b. a receiver having:
    i. a base having a first end, a second end, an outer surface, and an inner surface defining a volume configured to receive and articulate the head;
    ii. a first opening having a second keyed contour configured to engage and disengage with the head of the bone anchor; and
    iii. a second opening extending from the first opening and the volume, wherein the second opening is generally perpendicular to the first opening and configured to engage and disengage with the neck of the bone anchor, and wherein the first and second openings permit insertion of the head into the volume upon at least rotation of the first keyed contour with respect to the second keyed contour in a first rotation direction and subsequent rotation of the first keyed contour with respect to the second keyed contour in a second rotation direction different from the first rotation direction before the head is fully captured and pivotable within the volume.

25. The assembly of claim 24, further comprising a rod.

26. The assembly of claim 25, wherein the receiver further comprises a rod slot configured to accept the rod.

27. The assembly of claim 25, wherein the receiver further comprises a compression element positioned between the first receiver end and the second receiver end, the compression element configured to transfer a force from the rod to the head.

28. The assembly of claim 25, wherein the receiver further comprises a threaded bore configured to threadably receive a set screw.

29. The assembly of claim 24, wherein the first keyed contour comprises a proximal recess formed in the head.

30. The assembly of claim 24, wherein the second keyed contour comprises an interference element extending at least partially over the first opening.

31. The assembly of claim 24, wherein the bone anchor further comprises one or more reliefs positioned on at least one of the neck and second end.

32. The assembly of claim 31, wherein the bone anchor has a longitudinal axis extending through the first and second ends, the receiver has a receiver axis extending through the first and second receiver ends, and the second opening is configured to permit pivoting of the neck out of the second opening and towards coaxial alignment with the receiver axis only upon rotation of the bone anchor by a first number of degrees about the longitudinal axis when the head is fully received within the volume.

\* \* \* \* \*